US011236338B2

(12) United States Patent
Wilton et al.

(10) Patent No.: US 11,236,338 B2
(45) Date of Patent: Feb. 1, 2022

(54) ANTISENSE-INDUCED EXON2 INCLUSION IN ACID ALPHA-GLUCOSIDASE

(71) Applicants: Sarepta Therapeutics, Inc., Cambridge, MA (US); Murdoch University, Murdoch (AU)

(72) Inventors: Stephen Donald Wilton, Applecross (AU); Sue Fletcher, Bayswater (AU); Gunnar James Hanson, Cambridge, MA (US); Richard Keith Bestwick, Corvallis, OR (US)

(73) Assignees: SAREPTA THERAPEUTICS, INC., Cambridge, MA (US); MURDOCH UNIVERSITY, Murdoch (AU)

( * ) Notice: Subject to any disclaimer, the term of this patent is extended or adjusted under 35 U.S.C. 154(b) by 0 days.

(21) Appl. No.: 14/917,173

(22) PCT Filed: Sep. 5, 2014

(86) PCT No.: PCT/US2014/054384
§ 371 (c)(1),
(2) Date: Mar. 7, 2016

(87) PCT Pub. No.: WO2015/035231
PCT Pub. Date: Mar. 12, 2015

(65) Prior Publication Data
US 2016/0208264 A1  Jul. 21, 2016

Related U.S. Application Data

(60) Provisional application No. 61/932,195, filed on Jan. 27, 2014, provisional application No. 61/874,261, filed on Sep. 5, 2013.

(51) Int. Cl.
*C12N 15/11* (2006.01)
*C12N 15/113* (2010.01)
*C07F 9/6533* (2006.01)

(52) U.S. Cl.
CPC ........ *C12N 15/1137* (2013.01); *C07F 9/6533* (2013.01); *C12N 2310/11* (2013.01); *C12N 2310/315* (2013.01); *C12N 2310/3145* (2013.01); *C12N 2310/3181* (2013.01); *C12N 2310/321* (2013.01); *C12N 2310/3231* (2013.01); *C12N 2310/3233* (2013.01); *C12N 2310/3513* (2013.01); *C12N 2320/33* (2013.01); *C12Y 302/0102* (2013.01)

(58) Field of Classification Search
CPC . C12N 15/113; C12N 15/111; C12N 2310/11; C12N 2320/33
See application file for complete search history.

(56) References Cited

U.S. PATENT DOCUMENTS

| 7,422,874 B2 | 9/2008 | Kim | |
|---|---|---|---|
| 8,084,598 B1 | 12/2011 | Bentwich | |
| 2003/0166588 A1* | 9/2003 | Iversen | C07F 9/65583 514/44 A |
| 2004/0049022 A1 | 3/2004 | Nyce et al. | |
| 2005/0255487 A1* | 11/2005 | Khvorova | A61K 31/713 435/6.11 |
| 2006/0003322 A1* | 1/2006 | Bentwich | G06F 19/18 435/6.16 |
| 2012/0065169 A1 | 3/2012 | Hanson et al. | |
| 2014/0017212 A1 | 1/2014 | Rebar | |
| 2014/0330006 A1 | 11/2014 | Hanson et al. | |
| 2015/0133529 A1* | 5/2015 | Krieg | A61K 48/00 514/44 R |
| 2015/0141320 A1 | 5/2015 | Krieg | |
| 2015/0197534 A1 | 7/2015 | Wilton | |
| 2018/0216111 A1 | 8/2018 | Wilton | |

FOREIGN PATENT DOCUMENTS

| WO | 2011028941 | 3/2011 |
|---|---|---|
| WO | 2011107611 | 9/2011 |
| WO | 2012150960 | 11/2012 |
| WO | 2013074834 | 5/2014 |
| WO | 2015190921 | 12/2015 |

OTHER PUBLICATIONS

*Homo sapiens* PC4 and SFRS1 interacting protein 1 (PSIP1), transcript variant 1, mRNA, NCBI Reference Sequence: NM_021144. 3, retrieved from www.ncbi.nlm.nih.gov on Oct. 26, 2017.*
*Homo sapiens* BRCA1/BRCA2-containing complex subunit 3 (BRCC3), transcript variant 1, mRNA, NCBI Reference Sequence: NM _024332.3, retrieved from www.ncbi.nlm.nih.gov on Oct. 26, 2017.*
Predicted: Fukomys damarensis uncharacterized LOC104866798 (LOC104866798), transcript variant X3, ncRNA, NCBI Reference Sequence: XR_781573.1, retrieved from www.ncbi.nlm.nih.gov on Oct. 26, 2017.*
Predicted: Pyrus x bretschneideri FACT complex subunit SPT16-like (LOC103955324), transcript variant X2, mRNA, NCBI Reference Sequence: XM_009367198.2, retrieved from www.ncbi.nlm.nih.gov on Oct. 26, 2017.*

(Continued)

*Primary Examiner* — Dana H Shin
(74) *Attorney, Agent, or Firm* — Lathrop GPM LLP; Brian C. Trinque

(57) ABSTRACT

The present disclosure relates to antisense oligomers and related compositions and methods for inducing exon inclusion as a treatment for glycogen storage disease type II (GSD-II) (also known as Pompe disease, glycogenosis II, acid maltase deficiency (AMD), acid alpha-glucosidase deficiency, and lysosomal alpha-glucosidase deficiency), and more specifically relates to inducing inclusion of exon 2 and thereby restoring levels of enzymatically active acid alpha-glucosidase (GAA) protein encoded by the GAA gene.

8 Claims, 8 Drawing Sheets
Specification includes a Sequence Listing.

(56) References Cited

OTHER PUBLICATIONS

Van der Wal, Antisense oligonucleotides promote exon inclusion and correct the common c.-32-13T>G GAA splicing variant in Pompe disease, Molecular Therapy: Nucleic Acids, vol. 7, pp. 90-100. (Year: 2017).*
Yan et al., Transcriptional regulatio of the human acid alpha-glucosidase gene, The Journal of Biological Chemistry, vol. 276, pp. 1789-1793.. (Year: 2001).*
Yan et al., Identification and characterization of a tissue-specific silencer element in the first intron of the human acid maltase gene, Human Genetics, vol. 109, pp. 186-190. (Year: 2001).*
Bruno et al., Correction of aberrant FGFR1 alternative RNA splicing through targeting of intronic regulatory elements, Human Molecular Genetics, vol. 13, pp. 2409-2420. (Year: 2004).*
Hammond et al., Genetic therapies for RNA mis-splicing diseases, Trends in Genetics, vol. 27, pp. 196-205. (Year: 2011).*
Boerkoel et al., Leaky splicing mutation in the acid maltase gene is associated with delayed onset of glycogenosis type II, American Journal of Human Genetics, vol. 56, pp. 887-897. (Year: 1995).*
Martiniuk et al., Isolation and partial characterization of the structural gene for human acid alpha glucosidase, DNA and Cell Biology, vol. 10, pp. 283-292. (Year: 1991).*
USPTO; Restriction Requirement dated Sep. 18, 2015 in U.S. Appl. No. 14/479,029.
USPTO; Non-Final Office Action dated Apr. 18, 2016 in U.S. Appl. No. 14/479,029.
Accession No. MIMAT0021051, mature sequence gma-miR1523b, accessed and retrived from www.mirbase.org on Apr. 12, 2016.
Accession No. MIMAT0029917, mature sequence cbr-miR-2231, accessed and retrived from www.mirbase.org on Apr. 12, 2016.
Accession Number MIMAT0025174, mature sequence mmu-miR-6418-3p, accessed and retrived from www.mitbase.org on Apr. 12, 2016.
Levin et al., Position-dependent effects of locked nucleic acid (LNA) on DNA sequencing and PCR primers, Nucleic Acids Research, vol. 34, e 142, pp. 1-11. Oct. 28, 2006.
International Search Report and Written Opinion dated Sep. 12, 2014 in PCT/ US2014/054384.
Byrne, B.J. et al., "Pompe disease gene therapy." Human Molecular Genetics, vol. 20, No. RI 1, pp. R61-R68. Apr. 25, 2011.
Database Accession No. AZX50184, "Human GM-CSF AUG (−118-99) Anti Sense Oligonucleotide, SEQ ID No. 10 from WO2012092645," XP002733113, Aug. 16, 2012.
Database Accession No. BAJ91176, "RPM-2 gene targeting antisense oligonucleotide, OL (14) TRPM2, SEQ 106 from WO2013009979," XP002733114, Feb. 28, 2013.
Database Accession No. AEL86146, "Human TGF-beta2 mRNA hybridizable oligonucleotide, SEQ ID No. 8 from WO2006117400," XP002733115, Jan. 11, 2007.
Database Accession No. AEC47053, "Antisense oligonucleotide targeting human TGF-beta-1 #615 from WO2005084712," XP002733116, Nov. 17, 2005.
Database Accession No. ABD32089, "Human PDE4C-derived oligonucleotide SEQ ID 14300 from WO200285309," XP002733117, Jul. 29, 2004.
Database Accession No. AZQ33391, "Human TGFB1/TGFB2/TGFB3 gene targeted antisense oligonucleotide SEQ: 1640 from WO2011154542," XP 002733118, Feb. 2, 2012.
Huie, M.L. et al., "Aberrant splicing in adult onset glycogen storage disease type II (GSDII): molecular identification of an IVS1 (−13-G) mutation in a majority of patients and a novel IVS10 (+1GT-CT) mutation.", Human Molecular Genetics, vol. 3, No. 12, pp. 2231-2236, Dec. 4, 1994.
Mitrpant Chalermchai et al., "Improved Antisense Oligonucleotide Design to Suppress Aberrant SMN2 Gene Transcript Processing: Towards a Treatment for Spinal Muscular Atrophy." PLOS One, vol. 8, No. 4, E62114, pp. 1-10. (Apr. 2013).
PCT; Written Opinion dated Nov. 17, 2016 in PCT/US2016/020127.
PCT; International Search Report dated Nov. 17, 2016 in PCT/US2016/020127.
PCT; International Search Report dated Sep. 21, 2017 in Application No. PCT/US2017/028002.
PCT; Written Opinion dated Sep. 21, 2017 in Application No. PCT/US2017/028002.
Accession No. AC009890, genomic sequence for *Homo sapiens* clone H-NH0262L04 from chromosome 18, deposited on (Apr. 29, 2000).
Accession number JR118655, TSA: Capra hircus cuffB11 Gene ID 65169 mRNA sequence, deposited on (Oct. 29, 2012).
CN; First Office Action dated Feb. 24, 2018 in CN Application No. 201480060730.9.
EP; Examination report dated Nov. 8, 2017 in EP Application No. 14766370.2.
Bergsma Atze, "Identification and Characterization of Aberrant GAA Pre-mRNA Splicing in Pompe Disease Using a Generic Approach," Human Mutation, pp. 1-12, (2014).
Mengmeng et al., "The Application of Phosphorodiamidate Morpholino Oligomers in the Research of Gene Function," Journal of Biology, vol. 29(6), pp. 77-80, (Dec. 31, 2013).
SG; Search Report dated Jan. 24, 2020 in the Application No. 11201808964P.
SG; Written Opinion dated Jan. 24, 2020 in the Application No. 11201808964P.
USPTO; Non-Final Office Action dated Mar. 17, 2020 in the U.S. Appl. No. 16/094,858.
JP; Office Action dated Mar. 26, 2020 in the JP Application No. 2017545273.

* cited by examiner

ANTISENSE-INDUCED EXON2 INCLUSION IN ACID ALPHA-GLUCOSIDASE

CROSS-REFERENCE TO RELATED APPLICATIONS

This application claims priority under 35 U.S.C. § 119(e) to U.S. Application No. 61/874,261, filed Sep. 5, 2013; and U.S. Application No. 61/932,195, filed Jan. 27, 2014; each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SATH_001_02WO_ST25.txt. The text file is about 62 KB, was created on Sep. 5, 2014, and is being submitted electronically via EFS-Web.

BACKGROUND

Field of the Disclosure

The present disclosure relates to antisense oligomers and related compositions and methods for inducing exon inclusion as a treatment for glycogen storage disease type II (GSD-II) (also known as Pompe disease, glycogenosis II, acid maltase deficiency (AMD), acid alpha-glucosidase deficiency, and lysosomal alpha-glucosidase deficiency), and more specifically relates to inducing inclusion of exon 2 and thereby restoring levels of enzymatically active acid alpha-glucosidase (GAA) protein encoded by the GAA gene.

Description of the Related Art

Alternative splicing increases the coding potential of the human genome by producing multiple proteins from a single gene. Inappropriate alternative splicing is also associated with a growing number of human diseases.

GSD-II is an inherited autosomal recessive lysosomal storage disorder caused by deficiency of an enzyme called acid alpha-glucosidase (GAA). The role of GAA within the body is to break down glycogen. Reduced or absent levels of GAA activity leads to the accumulation of glycogen in the affected tissues, including the heart, skeletal muscles (including those involved with breathing), liver, and nervous system. This accumulation of glycogen is believed to cause progressive muscle weakness and respiratory insufficiency in individuals with GSD-II. GSD-II can occur in infants, toddlers, or adults, and the prognosis varies according to the time of onset and severity of symptoms. Clinically, GSD-II may manifest with a broad and continuous spectrum of severity ranging from severe (infantile) to milder late onset adult form. The patients eventually die due to respiratory insufficiency. There is a good correlation between the severity of the disease and the residual acid alpha-glucosidase activity, the activity being 10-20% of normal in late onset and less than 2% in early onset forms of the disease. It is estimated that GSD-II affects approximately 5,000 to 10,000 people worldwide.

The most common mutation associated with the adult onset form of disease is IVS1-13T>G. Found in over two thirds of adult onset GSD-II patients, this mutation may confer a selective advantage in heterozygous individuals or is a very old mutation. The wide ethnic variation of adult onset GSD-II individuals with this mutation argues against a common founder.

The GAA gene consists of 20 exons spanning some 20 kb. The 3.4 kb mRNA encodes a protein with a molecular weight of approximately 105 kD. The IVS1-13T>G mutation leads to the loss of exon 2 (577 bases) which contains the initiation AUG codon.

Treatment for GSD-II has involved drug treatment strategies, dietary manipulations, and bone marrow transplantation without significant success. In recent years, enzyme replacement therapy (ERT) has provided new hope for GSD-II patients. For example, Myozyme®, a recombinant GAA protein drug, received approval for use in patients with GSD-II disease in 2006 in both the U.S. and Europe. Myozyme® depends on mannose-6-phosphates (M6P) on the surface of the GAA protein for delivery to lysosomes.

Antisense technology, used mostly for RNA down regulation, recently has been adapted to alter the splicing process. Processing the primary gene transcripts (pre-mRNA) of many genes involves the removal of introns and the precise splicing of exons where a donor splice site is joined to an acceptor splice site. Splicing is a precise process, involving the coordinated recognition of donor and acceptor splice sites, and the branch point (upstream of the acceptor splice site) with a balance of positive exon splice enhancers (predominantly located within the exon) and negative splice motifs (splice silencers are located predominantly in the introns).

Effective agents that can alter splicing of GAA pre-mRNAs are likely to be useful therapeutically for improved treatment of GSD-II.

SUMMARY

Embodiments of present disclosure relate to antisense oligomers and related compositions and methods for increasing the levels of exon 2-containing GAA-coding mRNA in a cell, comprising contacting the cell with an antisense oligomer of sufficient length and complementarity to specifically hybridize to a region within the pre-mRNA of the GAA gene, wherein binding of the antisense oligomer to the region increases the levels of exon 2-containing GAA-coding mRNA in the cell.

Accordingly, in some embodiments, the instant disclosure relates to an antisense oligomer of 10 to 40 nucleotides or nucleotide analogs, comprising a targeting sequence of sufficient length and complementarity to specifically hybridize to a region within intron 1 (SEQ ID NO:1), exon 2 (SEQ ID NO:2), or intron 2 (SEQ ID NO:3) of the pre-mRNA of the human acid alpha-glucosidase (GAA) gene.

In certain embodiments, the instant disclosure relates to an antisense oligomer compound, comprising:

a non-natural chemical backbone selected from a phosphoramidate or phosphorodiamidate morpholino oligomer (PMO), a peptide nucleic acid (PNA), a locked nucleic acid (LNA), a phosphorothioate oligomer, a tricyclo-DNA oligomer, a tricyclo-phosphorothioate oligomer, a 2'O-Me-modified oligomer, or any combination of the foregoing; and a targeting sequence complementary to a region within intron 1 (SEQ ID. NO. 1), intron 2 (SEQ ID. NO. 2), or exon 2 (SEQ ID. NO. 3) of a pre-mRNA of the human acid alpha-glucosidase (GAA) gene.

In some embodiments, the antisense oligomer specifically hybridizes to a region within the intron 1, exon 2, and/or intron 2 GAA sequence(s) set forth in Table 1. In some embodiments, the antisense oligomer specifically hybridizes to an intronic splice silencer element or an exonic splice silencer element. In certain embodiments, the antisense oligomer comprises a targeting sequence set forth in Table 2, a fragment of at least 10 contiguous nucleotides of a targeting sequence in Table 2, or variant having at least 80% sequence identity to a targeting sequence in Table 2. In specific embodiments, the antisense oligomer consists or consists essentially of a targeting sequence set forth in Table 2.

In certain embodiments, the antisense oligomer is a phosphoramidate or phosphorodiamidate morpholino oligomer (PMO), a PMO-X, a PPMO, a peptide nucleic acid (PNA), a locked nucleic acid (LNA), a phosphorothioate oligomer, a tricyclo-DNA oligomer, a tricyclo-phosphorothioate oligomer, a 2'O-Me-modified oligomer, or any combination of the foregoing.

In some embodiments, the antisense oligomer contains about, at least about, or no more than about 1, 2, 3, 4, 5, 6, 7, 8, 9, or 10 cationic internucleoside linkages. In certain embodiments, the antisense oligomer contains about or at least about 10%, 15%, 20%, 25%, 30%, 35%, 40%, 45%, 50%, 55%, 60%, 65%, 70%, 75%, 80%, 85%, 90%, 95%, or 100% cationic internucleoside linkages. In certain embodiments, the antisense oligomer contains about, at least about, or no more than about 1, 2, 3, 4, 5, 6, 7, 8, 9, or 10 internucleoside linkages that exhibits a pKa between about 4.5 and about 12. In some embodiments, the antisense oligomer contains about or at least about 10%, 15%, 20%, 25%, 30%, 35%, 40%, 45%, 50%, 55%, 60%, 65%, 70%, 75%, 80%, 85%, 90%, 95%, or 100% internucleoside linkages that exhibit a pKa between about 4.5 and about 12. In some embodiments, the antisense oligomer has an internucleoside linkage containing both a basic nitrogen and an alkyl, aryl, or aralkyl group. In some embodiments, the antisense oligomer comprises a morpholino.

In certain embodiments, the antisense oligomer of the disclosure is a compound of formula (I):

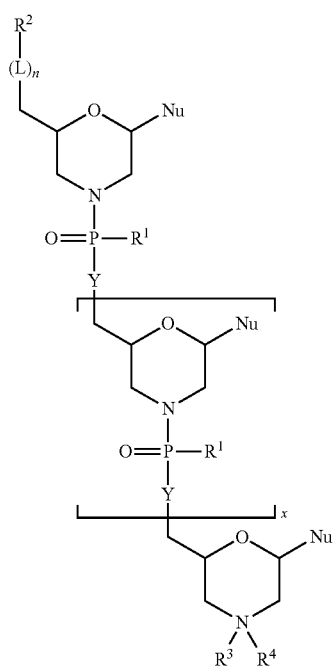

(I)

or a pharmaceutically acceptable salt thereof, wherein:
each Nu is a nucleobase which taken together forms a targeting sequence;
x is an integer from 8 to 38;
each Y is independently selected from O or —NR$^a$, wherein R$^a$ is selected from the group consisting of hydrogen, -T$^1$-NR$^c$R$^d$R$^e$, and —[(C(O)CHR'NH)$_m$]R", wherein:
R' is a side chain of a naturally occurring amino acid or a one- or two-carbon homolog thereof, R" is selected from Hydrogen or acyl, m is an integer from 1 to 60, R$^c$ is selected from the group consisting of hydrogen, C$_1$-C$_6$ alkyl, aralkyl, and —C(=NH)NH$_2$, R$^d$ is selected from the group consisting of hydrogen, aralkyl, and C$_1$-C$_6$ alkyl, or RC and R$^d$ taken together with the nitrogen atom to which they are attached form a 5-7 membered ring when R$^C$ and R$^d$ are each independently C$_1$-C$_6$ alkyl or aralkyl, where the ring is optionally substituted with a substituent selected from the group consisting of C$_1$-C$_6$ alkyl, phenyl, halogen, and aralkyl, and RC is selected from the group consisting of an electron pair, hydrogen, C$_1$-C$_6$ alkyl, and aralkyl;
each L is independently selected from the group consisting of —P(O)$_2$OH—, —P(O)$_2$R$^1$—, a piperazinyl group, a carbonyl group, H(O(CH$_2$)$_s$O)$_w$—, —(OCH$_2$CH$_2$O)$_w$, and —[(C(O)CHR'NH)$_m$]R", wherein w is an integer selected from 3-20, S is an integer selected from 1 to 8;
n is an integer from 0 to 3;
each R' is independently selected from the group consisting of —N(CH$_3$)$_2$, —NR$^5$R$^6$, —OR$^7$, a moiety of formula (II):

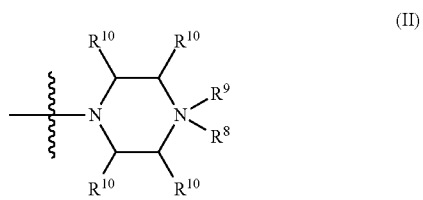

(II)

wherein R$^8$ is selected from the group consisting of hydrogen, methyl. —C(=NH)NH$_2$, —Z-T$^2$-NHC(=NH)NH$_2$, and —[(C(O)CHR'NH)$_m$]R", where Z is carbonyl or a direct bond, R$^9$ is selected from the group consisting of an electron pair, hydrogen, a C$_1$-C$_6$ alkyl, and aralkyl, and each R$^{10}$ is independently selected from hydrogen or methyl; and
a moiety of formula (III):

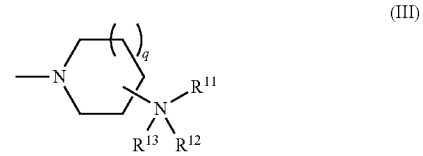

(III)

wherein q is an integer from 0 to 2, R$^{11}$ is selected from the group consisting of hydrogen, C$_1$-C$_6$ alkyl, aralkyl, and —C(=NH)NH$_2$, R$^{12}$ is selected from the group consisting of hydrogen, aralkyl, and C$_1$-C$_6$ alkyl, or R$^{11}$ and R$^{12}$ taken together with the nitrogen atom to which they are attached form a 5-7 membered ring where the ring is optionally substituted with a substituent selected from the group consisting of C$_1$-C$_6$ alkyl, phenyl, halogen, and aralkyl, and R$^{13}$ is selected from the group consisting of an electron pair, hydrogen, C$_1$-C$_6$ alkyl, and aralkyl;
R$^2$ is selected from the group consisting of hydrogen, OH, a nucleotide, —(CH$_2$)$_m$C(O)NR$^f$R$^g$ wherein R$^f$ and R$^g$ are independently selected from H, acyl, $C_1$-$C_6$ alkyl, and —[(C(O)CHR'NH)$_m$]R", —[(C(O)CHR'NH)$_m$]R", H(O(CH$_2$)$_s$O)$_w$—, H(OCH$_2$CH$_2$O)$_w$—, trityl, —C(=O)OR$^f$, and acyl, wherein R$^f$ is $C_1$-$C_{30}$ alkyl comprising one or more oxygen or hydroxyl moieties or combinations thereof, or R$^2$ is absent;

R$^3$ is selected from the group consisting of hydrogen, a $C_1$-$C_6$ alkyl, a nucleotide, —[(C(O)CHR'NH)$_m$]R", —C(=NH)NH$_2$, trityl, —C(=O)OR$^g$, acyl, —C(O)(CH$_2$)$_m$C(O), and T$^4$-(4,6-(NR$_2$)-1,3,5-triazin-2-yl)piperazin-1-yl, wherein R$^g$ is $C_1$-$C_{30}$ alkyl comprising one or more oxygen or hydroxyl moieties or combinations thereof, T$^4$ is selected from —C(O)(CH$_2$)$_6$C(O)— or —C(O)(CH$_2$)$_2$S$_2$(CH$_2$)$_2$C(O)—, and R is —(CH$_2$)OC(O)NH(CH$_2$)$_6$NHC(NH)NH$_2$;

R$^4$ is selected from the group consisting of an electron pair, hydrogen, a $C_1$-$C_6$ alkyl, and acyl, and each R$^5$ is independently selected from hydrogen or methyl;

each R$^6$ and each R$^7$ is independently selected from hydrogen or -T3-NR$^c$R$^d$R$^e$; and each of T$^1$, T$^2$, and T$^3$ is independently an optional linker of up to 18 atoms in length comprising alkyl, alkoxy, or alkylamino groups, or combinations thereof, wherein the targeting sequence is complementary to a region within intron 1 (SEQ ID. NO. 1), intron 2 (SEQ ID. NO. 2), or exon 2 (SEQ ID. NO. 3) of a pre-mRNA of the human acid alpha-glucosidase (GAA) gene.

In certain embodiments, the antisense oligomer of the disclosure is a compound of formula (IV):

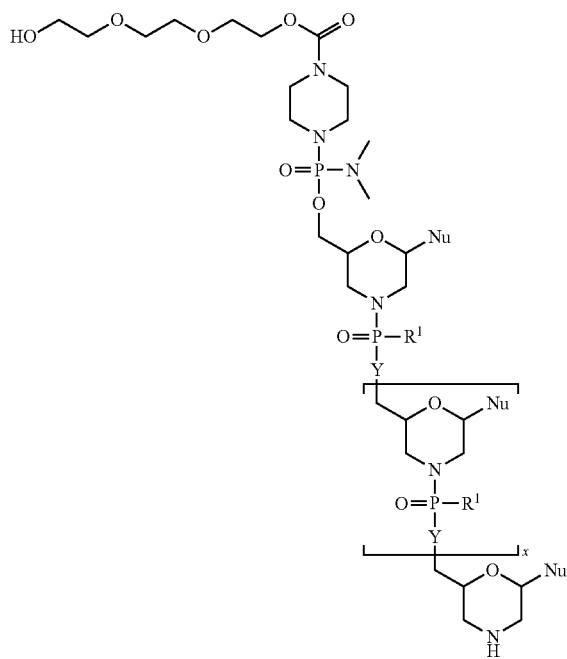

(IV)

or a pharmaceutically acceptable salt thereof, wherein:
each Nu is a nucleobase which taken together form a targeting sequence;
x is an integer from 15 to 25;
each Y is O;
each R$^1$ is independently selected from the group consisting of:

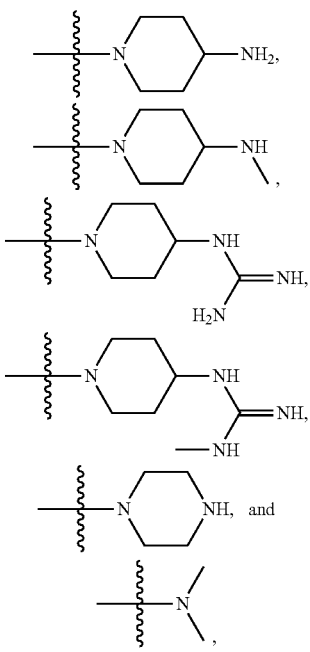

wherein at least one R$^1$ is —N(CH$_3$)$_2$, and wherein the targeting sequence is selected from SEQ ID NOS: 4-12, 14-103, 105-108, 110-113, and 115-118, wherein X is selected from uracil (U) or thymine (T).

In certain embodiments, the antisense oligomer further comprises a peptide moiety which enhances cellular uptake.

Also included within the scope of the disclosure are antisense oligomer, comprising a targeting sequence of sufficient length and complementarity to specifically hybridize to a region within intron 1 (SEQ ID NO:1), exon 2 (SEQ ID NO:2), or intron 2 (SEQ ID NO:3) of the pre-mRNA of the human acid alpha-glucosidase (GAA) gene, as set forth in Table 2. In some embodiments, the targeting sequence comprises at least 10 contiguous nucleotides of a targeting sequence selected from SEQ ID. NOS: 4-12, 14-103, 105-108, 110-113, and 115-118, wherein X is selected from uracil (U) or thymine (T). In certain embodiments, the targeting sequence comprises 80% sequence identity to a targeting sequence selected from SEQ Ill. NOS: 4-12, 14-103, 105-108, 110-113, and 115-118, wherein X is selected from uracil (U) or thymine (T).

In particular embodiments, the antisense oligomer is a phosphoramidate or phosphorodiamidate morpholino oligomer (PMO), a PMO-X, a PPMO, a peptide nucleic acid (PNA), a locked nucleic acid (LNA), a phosphorothioate oligomer, a tricyclo-DNA oligomer, a tricyclo-phosphorothioate oligomer, a 2'O-Me-modified oligomer, or any combination of the foregoing.

Also included are pharmaceutical compositions, comprising a physiologically-acceptable carrier and an antisense oligomer described herein.

Certain embodiments also include methods of increasing the level of exon 2-containing acid alpha-glucosidase (GAA) mRNA in a cell, comprising contacting the cell with an antisense oligomer of sufficient length and complementarity to specifically hybridize to a region within the pre-mRNA of the GAA gene, wherein binding of the antisense oligomer to the region increases the level of exon 2-containing GAA mRNA in the cell.

In some embodiments, the level of exon 2-containing GAA mRNA in the cell is increased by at least about 10% relative to a control. In certain embodiments, the level of functional GAA protein in the cell is increased by at least about 10% relative to a control. In certain embodiments, the cell has an IVS1-13T>G mutation in one or more alleles of its genome which (in the absence of antisense treatment) causes reduced expression of exon 2-containing GAA mRNA.

In some embodiments, the cell is in a subject in need thereof, and the method comprises administering the antisense oligomer to the subject. In some embodiments, the subject has or is at risk for having glycogen storage disease type II (GSD-II). Some embodiments of the disclosure relate to methods of treating glycogen storage disease type II (GSD-II; Pompe disease) in a subject in need thereof, comprising administering to the subject an effective amount of an antisense oligomer of the disclosure. While certain embodiments relate to antisense oligomers for use in the preparation of a medicament for the treatment of glycogen storage disease type II (GSD-II; Pompe disease).

In certain embodiments, the subject has or is at risk for having infantile GSD-II. In particular embodiments, the subject has or is at risk for having late onset GSD-II. In certain embodiments, the method comprises reducing the glycogen levels in one or more tissues of the subject by at least about 10% relative to a control.

In addition, the instant disclosure also includes a method of detecting exon 2 inclusion in a human acid alpha-glucosidase (GAA) gene mRNA, the method comprising:

amplifying the GAA mRNA with at least one polymerase chain reaction primer comprising a base sequence selected from the group consisting of SEQ ID NOS: 121, 122, or 123.

These and other aspects of the present disclosure will become apparent upon reference to the following detailed description and attached drawings. All references disclosed herein are hereby incorporated by reference in their entirety as if each was incorporated individually.

BRIEF DESCRIPTION OF THE DRAWINGS

FIG. 3A shows that oligomers 9 (GAA-IVS1 (−74-55)) and 12 GAA-IVS1 (−158-140)) induced exon 2-inclusion in human cells carrying the IVS1-13G>T mutation, as evidenced by reduced amplification of the ~600 base amplicon (relative to the full-length ~1177 base amplicon). FIG. 3B shows that oligomer 14 (GAA-IVS2 (−53-72)) induced exon-2 inclusion, and FIG. 3C shows that oligomers 20 (GAA-IVS2 (−173-192)) and 22 (GAA-IVS2 (−338-364)) likewise induced a degree of exon-2 inclusion.

DETAILED DESCRIPTION

I. Definitions

Figure 1:
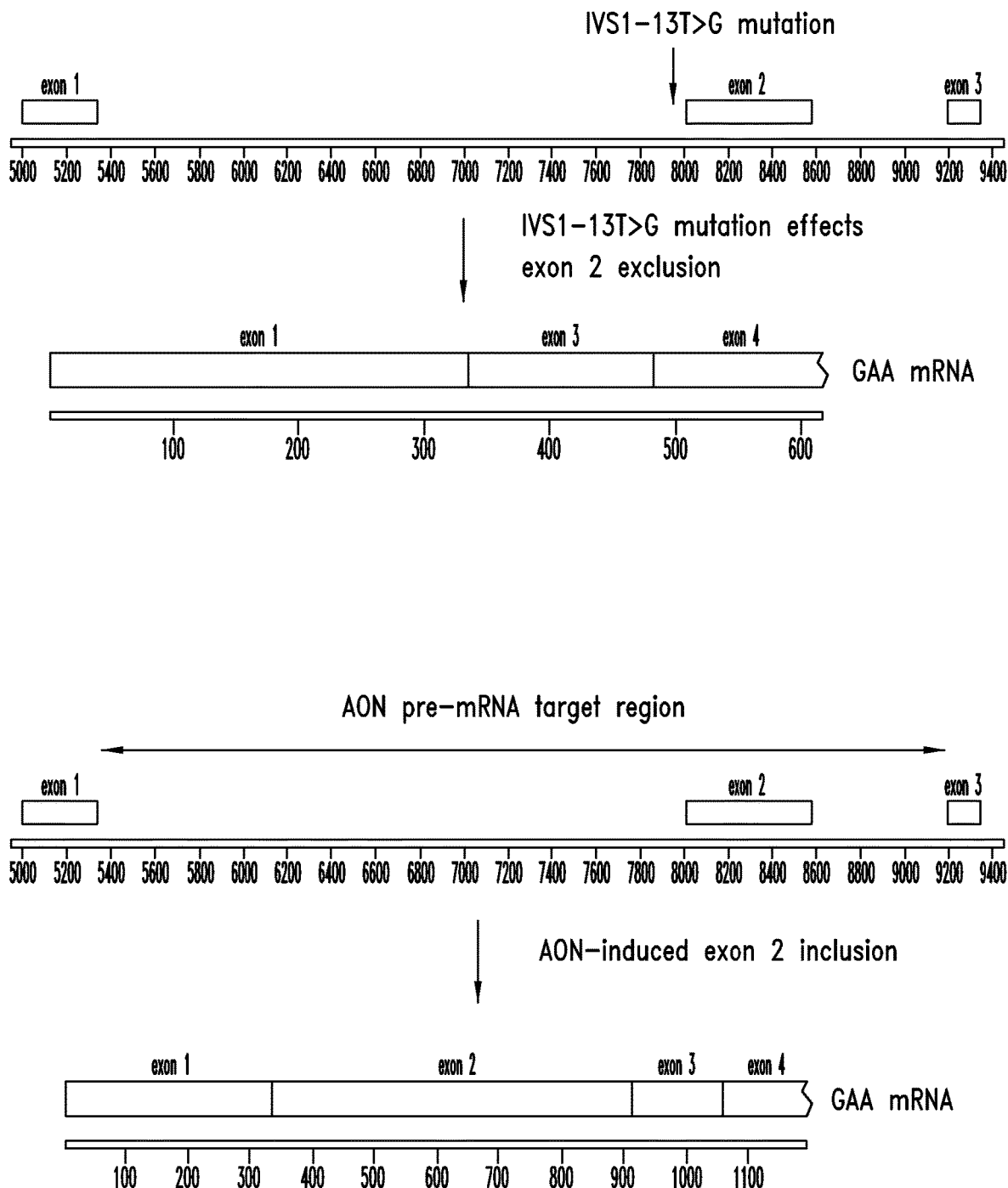
FIG. 1 illustrates one mechanism by which steric-blocking antisense oligomers can enhance the level of exon 2-containing GAA mRNA relative to exon-deleted GAA mRNA.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the subject matter of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "contacting a cell", "introducing" or "delivering" include delivery of the oligomers of the disclosure into a cell by methods routine in the art, e.g., transfection (e.g., liposome, calcium-phosphate, polyethyleneimine), electroporation (e.g., nucleofection), microinjection).

As used herein, the term "alkyl" is intended to include linear (i.e., unbranched or acyclic), branched, cyclic, or polycyclic non aromatic hydrocarbon groups, which are optionally substituted with one or more functional groups. Unless otherwise specified, "alkyl" groups contain one to eight, and preferably one to six carbon atoms. $C_1$-$C_6$ alkyl, is intended to include $C_1$, $C_2$, $C_3$, $C_4$, $C_5$, and $C_6$ alkyl groups. Lower alkyl refers to alkyl groups containing 1 to 6 carbon atoms. Examples of Alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

As used herein, the term "Alkoxy" means a subset of alkyl in which an alkyl group as defined above with the indicated number of carbons attached through an oxygen bridge. For example, "alkoxy" refers to groups —O-alkyl, wherein the alkyl group contains 1 to 3 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

As used herein, the term "aryl" used alone or as part of a larger moiety as in "aralkyl", "aralkoxy", or "aryloxyalkyl", refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "acyl" means a C(O)R group (in which R signifies H, alkyl or aryl as defined above). Examples of acyl groups include formyl, acetyl, benzoyl, phenylacetyl and similar groups.

The term "homolog" as used herein means compounds differing regularly by the successive addition of the same chemical group. For example, a homolog of a compound may differ by the addition of one or more —$CH_2$— groups, amino acid residues, nucleotides, or nucleotide analogs.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. In some embodiments, the CPPs are of the formula —$[(C(O)CHR'NH)_m]R''$ wherein R' is a side chain of a naturally occurring amino acid or a one- or two-carbon homolog thereof, R'' is selected from Hydrogen or acyl, and m is an integer up to 50. Additional CPPs are well-known in the art and are disclosed, for example, in U.S. Application No. 2010/0016215, which is incorporated by reference in its entirety. In other embodiments, m is an integer selected from 1 to 50 where, when m is 1, the moiety is a single amino acid or derivative thereof.

As used herein, "amino acid" refers to a compound consisting of a carbon atom to which are attached a primary amino group, a carboxylic acid group, a side chain, and a hydrogen atom. For example, the term "amino acid" includes, but is not limited to, Glycine, Alanine, Valine, Leucine, Isoleucine, Asparagine, Glutamine, Lysine and Arginine. Additionally, as used herein, "amino acid" also includes derivatives of amino acids such as esters, and amides, and salts, as well as other derivatives, including derivatives having pharmacoproperties upon metabolism to an active form. Accordingly, the term "amino acid" is understood to include naturally occurring and non-naturally occurring amino acids.

"An electron pair" refers to a valence pair of electrons that are not bonded or shared with other atoms.

"Homology" refers to the percentage number of amino acids that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated polynucleotide," "isolated oligonucleotide," or "isolated oligomer" as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The terms "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more antisense compounds or compositions to produce or cause a greater physiological response (i.e., downstream effects) in a cell or a subject relative to the response caused by either no antisense compound or a control compound. Relevant physiological or cellular responses (in vivo or in vitro) will be apparent to persons skilled in the art, and may include increases in the inclusion of exon 2 in a GAA-coding pre-mRNA, or increases in the expression of functional GAA enzyme in a cell, tissue, or subject in need thereof. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times), including all integers and decimal points in between and above 1 (e.g., 1.5, 1.6, 1.7. 1.8), the amount produced by no antisense compound (the absence of an agent) or a control compound. The term "reduce" or "inhibit" may relate generally to the ability of one or more antisense compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of a glycogen storage disease such as Pompe disease, for example, a decrease in the accumulation of glycogen in one or more tissues. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

As used herein, an "antisense oligonucleotide," "antisense oligomer" or "oligonucleotide" refers to a linear sequence of nucleotides, or nucleotide analogs, which allows the nucleobase to hybridize to a target sequence in an RNA by Watson-Crick base pairing, to form an oligomer:RNA heteroduplex within the target sequence. The terms "antisense oligonucleotide", "antisense oligomer", "oligomer" and "compound" may be used interchangeably to refer to an oligomer. The cyclic subunits may be based on ribose or another pentose sugar or, in certain embodiments, a morpholino group (see description of morpholino oligomers below). Also contemplated are peptide nucleic acids (PNAs), locked nucleic acids (LNAs), tricyclo-DNA oligomers, tricyclo-phosphorothioate oligomers, and 2'-O-Methyl oligomers, among other antisense agents known in the art.

Included are non-naturally-occurring oligomers, or "oligonucleotide analogs," including oligomers having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligomer analogs support bases capable of hydrogen bonding by Watson-Crick base pairing to standard polynucleotide bases, where the analog backbone presents the bases in a manner to permit such hydrogen bonding in a sequence-specific fashion between the oligomer analog molecule and bases in a standard polynucleotide (e.g., single-stranded RNA or single-stranded DNA). Preferred analogs are those having a substantially uncharged, phosphorus containing backbone.

A "nuclease-resistant" oligomer refers to one whose backbone is substantially resistant to nuclease cleavage, in non-hybridized or hybridized form; by common extracellular and intracellular nucleases in the body (for example, by exonucleases such as 3'-exonucleases, endonucleases, RNase H); that is, the oligomer shows little or no nuclease cleavage under normal nuclease conditions in the body to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligomer. Exemplary analogs include hypoxanthine (the base component of the nucleoside inosine); 2, 6-diaminopurine; 5-methyl cytosine; $C_5$-propynyl-modified pyrimidines; 9-(aminoethoxy)phenoxazine (G-clamp) and the like.

Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated.

Further examples of base pairing moieties include, but are not limited to, expanded-size nucleobases in which one or more benzene rings has been added. Nucleic base replacements described in the Glen Research catalog (www.glenresearch.com); Krueger A T et al, Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the oligomers described herein. Examples of expanded-size nucleobases are shown below:

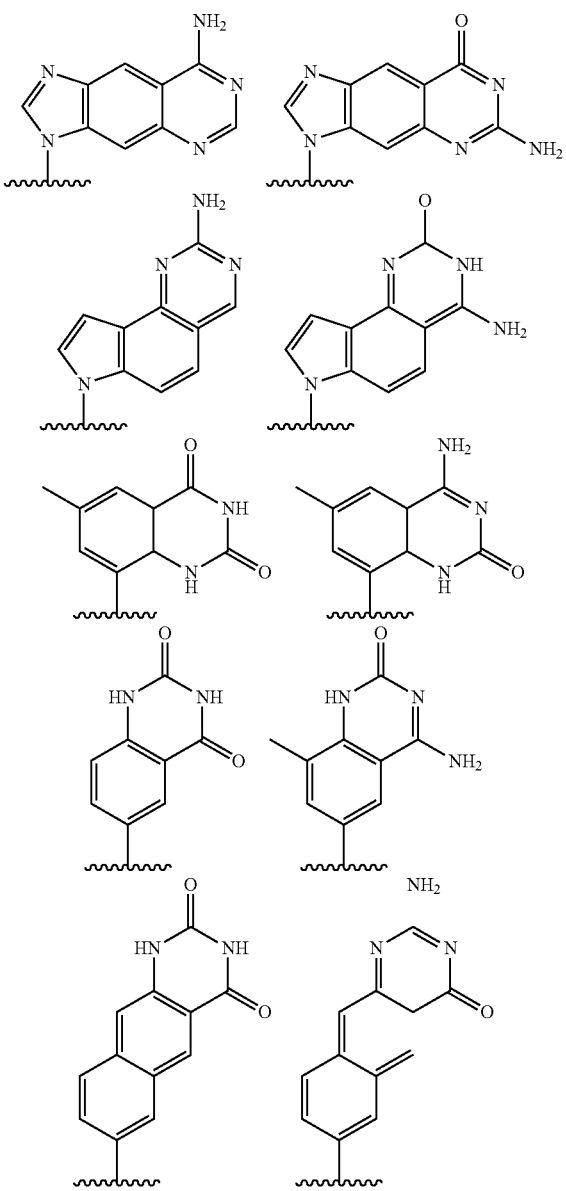

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligomer.

An oligomer "specifically hybridizes" to a target polynucleotide if the oligomer hybridizes to the target under physiological conditions, with a Tm substantially greater than 40° C. or 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

As used herein, "sufficient length" refers to an antisense oligomer that is complementary to at least 8, more typically 8-40, contiguous nucleobases in a region of GAA intron 1, exon 2, or intron 2, or a region spanning any of the foregoing. An antisense oligomer of sufficient length has at least a minimal number of nucleotides to be capable of specifically hybridizing to a region of the GAA pre-mRNA repeat in the mutant RNA. Preferably an oligomer of sufficient length is from 8 to 30 nucleotides in length. More preferably, an oligomer of sufficient length is from 9 to 27 nucleotides in length.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

A "subject" or a "subject in need thereof" includes a mammalian subject such as a human subject. Exemplary mammalian subjects have or are at risk for having GSD-II (or Pompe disease). As used herein, the term "GSD-II" refers to glycogen storage disease type II (GSD-II or Pompe disease), a human autosomal recessive disease that is often characterized by under expression of GAA protein in affected individuals. In certain embodiments, a subject has reduced expression and/or activity of GAA protein in one or more tissues, for example, heart, skeletal muscle, liver, and nervous system tissues. In some embodiments, the subject has increased accumulation of glycogen in one or more tissues, for example, heart, skeletal muscle, liver, and nervous system tissues. In specific embodiments, the subject has a IVS1-13T>G mutation or other mutation that leads to reduced expression of functional GAA protein (see, e.g., Zampieri et al., European J. Human Genetics. 19:422-431, 2011).

As used herein, the term "target" refers to a RNA region, and specifically, to a region identified by the GAA gene. In a particular embodiment the target is a region within intron 1 or intron 2 of the GAA-coding pre-mRNA, which is responsible for suppression of a signal that promotes exon 2 inclusion. In another embodiment the target region is a region of the mRNA of GAA exon 2.

The term "target sequence" refers to a portion of the target RNA against which the oligomer analog is directed, that is, the sequence to which the oligomer analog will hybridize by Watson-Crick base pairing of a complementary sequence.

The term "targeting sequence" is the sequence in the oligomer or oligomer analog that is complementary (meaning, in addition, substantially complementary) to the "target sequence" in the RNA genome. The entire sequence, or only a portion, of the antisense oligomer may be complementary to the target sequence. For example, in an oligomer having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases in the oligomer, but may alternatively be formed of non-contiguous sequences that when placed together, e.g., from opposite ends of the oligomer, constitute sequence that spans the target sequence.

A "targeting sequence" may have "near" or "substantial" complementarity to the target sequence and still function for the purpose of the present disclosure, that is, still be "complementary." Preferably, the oligomer analog compounds employed in the present disclosure have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

As used herein, the term "quantifying", "quantification" or other related words refer to determining the quantity, mass, or concentration in a unit volume, of a nucleic acid, polynucleotide, oligomer, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

II. Sequences for Splice Modulation of GAA

Certain embodiments relate to methods for enhancing the level of exon 2-containing GAA-coding mRNA relative to exon-2 deleted GAA mRNA in a cell, comprising contacting the cell with an antisense oligomer of sufficient length and complementarity to specifically hybridize to a region within the GAA gene, such that the level of exon 2-containing GAA mRNA relative to exon-2 deleted GAA mRNA in the cell is enhanced. In some embodiments, the cell is in a subject, and the method comprises administering to the antisense oligomer to the subject.

An antisense oligomer can be designed to block or inhibit or modulate translation of mRNA or to inhibit or modulate pre-mRNA splice processing, or induce degradation of targeted mRNAs, and may be said to be "directed to" or "targeted against" a target sequence with which it hybridizes. In certain embodiments, the target sequence includes a region including a 3' or 5' splice site of a pre-processed mRNA, a branch point, or other sequence involved in the regulation of splicing. The target sequence may be within an exon or within an intron or spanning an intron/exon junction.

In certain embodiments, the antisense oligomer has sufficient sequence complementarity to a target RNA (i.e., the RNA for which splice site selection is modulated) to block a region of a target RNA (e.g., pre-mRNA) in an effective manner. In exemplary embodiments, such blocking of GAA pre-mRNA serves to modulate splicing, either by masking a binding site for a native protein that would otherwise modulate splicing and/or by altering the structure of the targeted RNA. In some embodiments, the target RNA is target pre-mRNA (e.g., GAA gene pre-mRNA).

An antisense oligomer having a sufficient sequence complementarity to a target RNA sequence to modulate splicing of the target RNA means that the antisense agent has a sequence sufficient to trigger the masking of a binding site for a native protein that would otherwise modulate splicing and/or alters the three-dimensional structure of the targeted RNA. Likewise, an oligomer reagent having a sufficient sequence complementary to a target RNA sequence to modulate splicing of the target RNA means that the oligomer reagent has a sequence sufficient to trigger the masking of a binding site for a native protein that would otherwise modulate splicing and/or alters the three-dimensional structure of the targeted RNA.

In certain embodiments, the antisense oligomer has sufficient length and complementarity to a sequence in intron 1 of the human GAA pre-mRNA, exon 2 of the human GAA pre-mRNA, or intron 2 of the human GAA pre-mRNA. Also included are antisense oligomers which are complementary to a region that spans intron 1/exon 2 of the human GAA pre-mRNA, or a region that spans exon 2/intron 2 of the human GAA pre-mRNA. The intron 1 (SEQ ID NO:1), exon 2 (SEQ ID NO:2), and intron 2 (SEQ ID NO:3) sequences for human the GAA gene are shown in Table 1 below (The highlighted T/G near the 3' end of SEQ ID NO:1 is the IVS1-13T>G mutation described above; the nucleotide at this position is either T or G).

TABLE 1

Target sequences for GAA-targeted oligomers (from NG_009822)

| Name | Sequence (5'-3') | SEQ ID NO |
|---|---|---|
| GAA-IVS1 | GTGAGACACCTGACGTCTGCCCCGCGCTGCCGGCGGTAACATCCCAGAAGCGGGTTT<br>GAACGTGCCTAGCCGTGCCCCCAGCCTCTTCCCCTGAGCGGAGCTTGAGCCCCAGAC<br>CTCTAGTCCTCCCGGTCTTTATCTGAGTTCAGCTTAGAGATGAACGGGGAGCCGCCC<br>TCCTGTGCTGGGCTTGGGGCTGGAGGCTGCATCTTCCCGTTTCTAGGGTTTCCTTTC<br>CCCTTTTGATCGACGCAGTGCTCAGTCCTGGCCGGGACCCGAGCCACCTCTCCTGCT<br>CCTGCAGGACGCACATGGCTGGGTCTGAATCCCTGGGGTGAGGAGCACCGTGGCCTG<br>AGAGGGGCCCCTGGGCCAGCTCTGAAATCTGAATGTCTCAATCACAAAGACCCCCT<br>TAGGCCAGGCCAGGGGTGACTGTCTCTGGTCTTTGTCCCTGGTTGCTGGCACATAGC<br>ACCCGAAACCCTTGGAAACCGAGTGATGAGAGAGCCTTTTGCTCATGAGGTGACTGA<br>TGACCGGGGACACCAGGTGGCTTCAGGATGGAAGCAGATGGCCAGAAAGACCAAGGC<br>CTGATGACGGGTTGGGATGGAAAAGGGGTGAGGGGCTGGAGATTGAGTGAATCACCA<br>GTGGCTTAGTCAACCATGCCTGCACAATGGAACCCCGTAAGAAACCACAGGGATCAG<br>AGGGCTTCCCGCCGGGTTGTGGAACACACCAAGGCACTGGAGGGTGGTGCGAGCAGA<br>GAGCACAGCATCACTGCCCCCACCTCACACCAGGCCCTACGCATCTCTTCCATACGG<br>CTGTCTGAGTTTTATCCTTTGTAATAAACCAGCAACTGTAAGAAACGCACTTTCCTG<br>AGTTCTGTGACCCTGAAGAGGGAGTCCTGGGAACCTCTGAATTTATAACTAGTTGAT<br>CGAAAGTACAAGTGACAACCTGGGATTTGCCATTGGCCTCTGAAGTGAAGGCAGTGT<br>TGTGGGACTGAGCCCTTAACCTGTGGAGTCTGTGCTGACTCCAGGTAGTGTCAAGAT<br>TGAATTGAATTGTAGGACACCCAGCCGTGTCCAGAAAGTTGCAGAATTGATGGGTGT<br>GAGAAAAACCCTACACATTTAATGTCAGAAGTGTGGGTAAAATGTTTCACCCTCCAG<br>CCCAGAGAGCCCTAATTTACCAGTGGCCCACGGTGGAACACCACGTCCGGCCGGGGG<br>CAGAGCGTTCCCAGCCAAGCCTTCTGTAACATGACATGACAGGTCAGACTCCCTCGG<br>GCCCTGAGTTCACTTCTTCCTGGTATGTGACCAGCTCCCAGTACCAGAGAAGGTTGC<br>ACAGTCCTCTGCTCCAAGGAGCTTCACTGGCCAGGGGCTGCTTTCTGAAATCCTTGC<br>CTGCCTCTGCTCCAAGGCCCGTTCCTCAGAGACGCAGACCCCTCTGATGGCTGACTT<br>TGGTTTGAGGACCTCTCTGCATCCCTCCCCCATGGCCTTGCTCCTAGGACACCTTCT<br>TCCTCCTTTCCCTGGGGTCAGACTTGCCTAGGTGCGGTGGCTCTCCCAGCCTTCCCC<br>ACGCCCTCCCCATGGTGTATTACACACACCAAAGGGACTCCCCTATTGAAATCCATG<br>CATATTGAATCGCATGTGGGTTCCGGCTGCTCCTGGGAGGAGCCAGGCTAATAGAAT<br>GTTTGCCATAAAATATTAATGTACAGAGAAGCGAAACAAAGGTCGTTGGTACTTGTT<br>AACCTTACCAGCAGAATAATGAAAGCGAACCCCCATATCTCATCTGCACGCGACATC<br>CTTGTTGTGTCTGTACCCGAGGCTCCAGGTGCAGCCACTGTTACAGAGACTGTGTTT<br>CTTCCCCATGTACCTCGGGGGCCGGGAGGGGTTCTGATCTGCAAAGTCGCCAGAGGT<br>TAAGTCCTTTCTCTCTTGTGGCTTTGCCACCCCTGGAGTGTCACCCTCAGCTGCGGT<br>GCCCAGGATTCCCCACTGTGGTATGTCCGTGCACCAGTCAATAGGAAAGGGAGCAAG<br>GAAAGGTACTGGGTCCCCCTAAGGACATACGAGTTGCCAGAATCACTTCCGCTGACA<br>CCCAGTGGACCAAGCCGCACCTTTATGCAGAAGTGGGGCTCCCAGCCAGGCGTGGTC<br>ACTCCTGAAATCCCAGCACTTCGGAAGGCCAAGGGGGGTGGATCACTTGAGCTCAGG<br>AGTTCGAGACCAGCCTGGGTAACATGGCAAAATCCCGTCTCTACAAAAATACAGAAA<br>ATTAGCTGGGTGCGGTGGTGTGTGCCTACAGTCCCAGCTACTCAGGAGGCTGAAGTG<br>GGAGGATTGCTTGAGTCTGGGAGGTGGAGGTTGCAGTGAGCCAGGATCTCACCACAG<br>CACTCTGGCCCAGGCGACAGCTGTTTGGCCTGTTTCAAGTGTCTACCTGCCTTGCTG<br>GTCTTCCTGGGGACATTCTAAGCGTGTTTGATTTGTAACATTTTAGCAGACTGTGCA | 1 |

TABLE 1-continued

Target sequences for GAA-targeted oligomers (from NG_009822)

| Name | Sequence (5'-3') | SEQ ID NO |
|---|---|---|
|  | AGTGCTCTGCACTCCCCTGCTGGAGCTTTTCTCGCCCTTCCTTCTGGCCCTCTCCCC<br>AGTCTAGACAGCAGGGCAACACCCACCCTGGCCACCTTACCCCACCTGCCTGGGTGC<br>TGCAGTGCCAGCCGCGGTTGATGTCTCAGAGCTGCTTTGAGAGCCCCGTGAGTGCCG<br>CCCCTCCCGCCTCCCTGCTGAGCCCGCTTT/GCTTCTCCCGCAG |  |
| GAA-exon2 | GCCTGTAGGAGCTGTCCAGGCCATCTCCAACCATGGGAGTGAGGCACCCGCCCTGCT<br>CCCACCGGCTCCTGGCCGTCTGCGCCCTCGTGTCCTTGGCAACCGCTGCACTCCTGG<br>GGCACATCCTACTCCATGATTTCCTGCTGGTTCCCCGAGAGCTGAGTGGCTCCTCCC<br>CAGTCCTGGAGGAGACTCACCCAGCTCACCAGCAGGGAGCCAGCAGACCAGGGCCCC<br>GGGATGCCCAGGCACACCCCGGCCGTCCCAGAGCAGTGCCCACACAGTGCGACGTCC<br>CCCCCAACAGCCGCTTCGATTGCGCCCCTGACAAGGCCATCACCCAGGAACAGTGCG<br>AGGCCCGCGGCTGTTGCTACATCCCTGCAAAGCAGGGGCTGCAGGGAGCCCAGATGG<br>GGCAGCCCTGGTGCTTCTTCCCACCCAGCTACCCCAGCTACAAGCTGGAGAACCTGA<br>GCTCCTCTGAAATGGGCTACACGGCCACCCTGACCCGTACCACCCCCACCTTCTTCC<br>CCAAGGACATCCTGACCCTGCGGCTGGACGTGATGATGGAGACTGAGAACCGCCTCC<br>ACTTCACG | 2 |
| GAA-IVS2 | GTGGGCAGGGCAGGGGCGGGGCGGCGGCCAGGGCAGAGGGTGCGCGTGGACATCGA<br>CACCCACGCACCTCACAAGGGTGGGGTGCATGTTGCACCACTGTGTGCTGGGCCCTT<br>GCTGGGAGCGGAGGTGTGAGCAGACAATGGCAGCGCCCCTCGGGGAGCAGTGGGGAC<br>ACCACGGTGACAGGTACTCCAGAAGGCAGGGCTCGGGGCTCATTCATCTTTATGAAA<br>AGGTGGGTCAGGTAGAGTAGGGCTGCCAGAGGTTGCGAATGAAAACAGGATGCCCAG<br>TAAACCCGAATTGCAGATACCCCAGGCATGACTTTGTTTTTTTGTGTAAGGATGCAA<br>AATTTGGGATGTATTTATACTAGAAAAGCTGCTTGTTGTTTATCTGAAATTCAGAGT<br>TATCAGGTGTTCTGTATTTTACCTCCATCCTGGGGGAGGCGTCCTCCTCCTGGCTCT<br>GCAGATGAGGGAGCCGAGGCTCAGAGAGGCTGAATGTGCTGCCCATGGTCCCACATC<br>CATGTGTGGCTGCACCAGGACCTGACCTGTCCTTGGCGTGCGGGTTGTTCTCTGGAG<br>AGTAAGGTGGCTGTGGGAACATCAATAAACCCCCATCTCTTCTAG | 3 |

In certain embodiments, antisense targeting sequences are designed to hybridize to a region of one or more of the target sequences listed in Table 1. Selected antisense targeting sequences can be made shorter, e.g., about 12 bases, or longer, e.g., about 40 bases, and include a small number of mismatches, as long as the sequence is sufficiently complementary to effect splice modulation upon hybridization to the target sequence, and optionally forms with the RNA a heteroduplex having a Tm of 45° C. or greater.

In certain embodiments, the degree of complementarity between the target sequence and antisense targeting sequence is sufficient to form a stable duplex. The region of complementarity of the antisense oligomers with the target RNA sequence may be as short as 8-11 bases, but can be 12-15 bases or more, e.g., 10-40 bases, 12-30 bases, 12-25 bases, 15-25 bases, 12-20 bases, or 15-20 bases, including all integers in between these ranges. An antisense oligomer of about 14-15 bases is generally long enough to have a unique complementary sequence. In certain embodiments, a minimum length of complementary bases may be required to achieve the requisite binding Tm, as discussed herein.

In certain embodiments, oligomers as long as 40 bases may be suitable, where at least a minimum number of bases, e.g., 10-12 bases, are complementary to the target sequence. In some embodiments, facilitated or active uptake in cells is optimized at oligomer lengths of less than about 30 bases. For PMO oligomers, described further herein, an optimum balance of binding stability and uptake generally occurs at lengths of 18-25 bases. Included in the disclosure are antisense oligomers (e.g., PMOs, PMO-X, PNAs, LNAs, 2'-OMe) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to the target sequences of Table 1 (e.g., SEQ ID NOS:1-3, a sequence that spans SEQ ID NOS:1/2 or SEQ ID NOS:2/3).

The antisense oligomers typically comprises a base sequence which is sufficiently complementary to a sequence or region within or adjacent to intron 1, exon 2, or intron 2 of the pre-mRNA sequence of the human GAA gene. Ideally, an antisense oligomer is able to effectively modulate aberrant splicing of the GAA pre-mRNA, and thereby increase expression of active GAA protein. This requirement is optionally met when the oligomer compound has the ability to be actively taken up by mammalian cells, and once taken up, form a stable duplex (or heteroduplex) with the target mRNA, optionally with a Tm greater than about 40° C. or 45° C.

In certain embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo. Hence, certain oligomers may have substantial complementarity, meaning, about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligomer and the target sequence. Oligomer backbones that are less susceptible to cleavage by nucleases are discussed herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability.

Although such an antisense oligomer is not necessarily 100% complementary to the v target sequence, it is effective to stably and specifically bind to the target sequence, such that splicing of the target pre-RNA is modulated.

The stability of the duplex formed between an oligomer and a target sequence is a function of the binding Tm and the susceptibility of the duplex to cellular enzymatic cleavage. The Tm of an oligomer with respect to complementary-sequence RNA may be measured by conventional methods, such as those described by Hames et al., Nucleic Acid Hybridization, WI, Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80° C. or greater are also included. According to well-known principles, the Tm of an oligomer, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (45-50° C. or greater) at a length of 25 bases or less are generally preferred over those requiring greater than 25 bases for high Tm values.

Table 2 below shows exemplary targeting sequences (in a 5'-to-3' orientation) that are fully complementary to the intron 1, exon 2, or intron 2 pre-mRNA sequences of the human GAA gene.

TABLE 2

Antisense oligomer sequences for GAA-targeted oligomers

| Name | Sequence (5'-3') | SEQ ID NO |
|---|---|---|
| GAA Intron 1 Antisense Sequences | | |
| GAA-IVS1(-39-20) | GCXCAGCAGGGAGGCGGGAG | 4 |
| GAA-IVS1(-74-55) | GGCXCXCAAAGCAGCXCXGA | 5 |
| GAA-IVS1(-99-75) | GACAXCAACCGCGGCXGGCACXGCA | 6 |
| GAA-IVS1(-139-115) | GGGXAAGGXGGCCAGGGXGGGXGXX | 7 |
| GAA-IVS1(-158-140) | GCCCXGCXGXCXAGACXGG | 8 |
| GAA-IVS1(-179-160) | GAGAGGGCCAGAAGGAAGGG | 9 |
| GAA-IVS1.4.20 | GGGGCAGACGXCAGGXGXCX | 26 |
| GAA-IVS1.6.20 | GCGGGGCAGACGXCAGGXGX | 27 |
| GAA-IVS1.8.20 | GCGCGGGGCAGACGXCAGGX | 28 |
| GAA-IVS1.10.20 | CAGCGCGGGGCAGACGXCAG | 29 |
| GAA-IVS1.12.20 | GGCAGCGCGGGGCAGACGXC | 30 |
| GAA-IVS1.14.20 | CCGGCAGCGCGGGGCAGACG | 31 |
| GAA-IVS1.15.20 | GCCGGCAGCGCGGGGCAGAC | 32 |
| GAA-IVS1.17.20 | CCGCCGGCAGCGCGGGGCAG | 33 |
| GAA-IVS1.21.20 | GXXACCGCCGGCAGCGCGGG | 34 |

TABLE 2-continued

Antisense oligomer sequences for GAA-targeted oligomers

| Name | Sequence (5'-3') | SEQ ID NO |
|---|---|---|
| GAA-IVS1.24.20 | GAXGXXACCGCCGGCAGCGC | 35 |
| GAA-IVS1.26.20 | GGGAXGXXACCGCCGGCAGC | 36 |
| GAA-IVS1.28.20 | CXGGGAXGXXACCGCCGGCA | 37 |
| GAA-IVS1.30.20 | XXCXGGGAXGXXACCGCCGG | 38 |
| GAA-IVS1.32.20 | GCXXCXGGGAXGXXACCGCC | 39 |
| GAA-IVS1.2013.20 | GCAACXCGXAXGXCCXXAGG | 40 |
| GAA-IVS1.2015.20 | XGGCAACXCGXAXGXCCXXA | 41 |
| GAA-IVS1.2017.20 | XCXGGCAACXCGXAXGXCCX | 42 |
| GAA-IVS1.2019.20 | AXXCXGGCAACXCGXAXGXC | 43 |
| GAA-IVS1.2022.20 | GXGAXXCXGGCAACXCGXAX | 44 |
| GAA-IVS1.2024.20 | AAGXGAXXCXGGCAACXCGX | 45 |
| GAA-IVS1.2037.20 | XGGGXGXCAGCGGAAGXGAX | 46 |
| GAA-IVS1.2041.20 | CCACXGGGXGXCAGCGGAAG | 47 |
| GAA-IVS1.2043.20 | GXCCACXGGGXGXCAGCGGA | 48 |
| GAA-IVS1.2045.20 | XGGXCCACXGGGXGXCAGCG | 49 |
| GAA-IVS1.2048.20 | GCXXGGXCCACXGGGXGXCA | 50 |
| GAA-IVS1.2069.20 | CCACXXCXGCAXAAAGGXGC | 51 |
| GAA-IVS1.2071.20 | CCCCACXXCXGCAXAAAGGX | 52 |
| GAA-IVS1.2073.20 | AGCCCCACXXCXGCAXAAAG | 53 |
| GAA-IVS1.2075.20 | GGAGCCCCACXXCXGCAXAA | 54 |
| GAA-IVS1.2077.20 | XGGGAGCCCCACXXCXGCAX | 55 |
| GAA-IVS1.2079.20 | GCXGGGAGCCCCACXXCXGC | 56 |
| GAA-IVS1.2081.20 | XGGCXGGGAGCCCCACXXCX | 57 |
| GAA-IVS1.2088.20 | CCACGCCXGGCXGGGAGCCC | 58 |
| GAA-IVS1.2115.20 | XCCGAAGXGCXGGGAXXXCA | 59 |
| GAA-IVS1.2132.20 | XCCACCCCCCXXGGCCXXCC | 60 |
| GAA-IVS1.2135.20 | XGAXCCACCCCCCXXGGCCX | 61 |
| GAA-IVS1.2140.20 | XCAAGXGAXCCACCCCCCXX | 62 |
| GAA-IVS1.2143.20 | AGCXCAAGXGAXCCACCCCC | 63 |
| GAA-IVS1.2152.20 | GAACXCCXGAGCXCAAGXGA | 64 |
| GAA-IVS1.2156.20 | XCXCGAACXCCXGAGCXCAA | 65 |
| GAA-IVS1.2163.20 | AGGCXGGXCXCGAACXCCXG | 66 |
| GAA-IVS1.2165.20 | CCAGGCXGGXCXCGAACXCC | 67 |
| GAA-IVS1.2178.20 | XXXGCCAXGXXACCCAGGCX | 68 |
| GAA-IVS1.2183.20 | GGGAXXXXGCCAXGXXACCC | 69 |
| GAA-IVS1.2185.20 | ACGGGAXXXXGCCAXGXXAC | 70 |
| GAA-IVS1.2188.20 | GAGACGGGAXXXXGCCAXGX | 71 |

TABLE 2-continued

Antisense oligomer sequences for GAA-targeted oligomers

| Name | Sequence (5'-3') | SEQ ID NO |
|---|---|---|
| GAA-IVS1.2190.20 | XAGAGACGGGAXXXXGCCAX | 72 |
| GAA-IVS1.2195.20 | XXXXGXAGAGACGGGAXXXX | 73 |
| GAA-IVS1.2200.20 | XGXAXXXXXGXAGAGACGGG | 74 |
| GAA-IVS1.2202.20 | XCXGXAXXXXXGXAGAGACG | 75 |
| GAA-IVS1.2204.20 | XXXCXGXAXXXXXGXAGAGA | 76 |
| GAA-IVS1.2206.20 | AXXXXCXGXAXXXXXGXAGA | 77 |
| GAA-IVS1.2208.20 | XAAXXXXCXGXAXXXXXGXA | 78 |
| GAA-IVS1.2210.20 | GCXAAXXXXCXGXAXXXXXG | 79 |
| GAA-IVS1(-74-55) | GGCXCXCAAAGCAGCXCXGA | 104 |
| GAA-IVS1(-79-55) | GGCXCXCAAAGCAGCXCXGAGACAX | 105 |
| GAA-IVS1(-74-50) | CACGGGGCXCXCAAAGCAGCXCXGA | 106 |
| GAA-IVS1(-79-60) | XCAAAGCAGCXCXGAGACAX | 107 |
| GAA-IVS1(-69-55) | CACGGGGCXCXCAAAGCAGC | 108 |
| GAA-IVS1(-158-140) | GCCCXGCXGXCXAGACXGG | 109 |
| GAA-IVS1(-163-140) | GCCCXGCXGXCXAGACXGGGGAGA | 110 |
| GAA-IVS1(-158-135) | GXGXXGCCCXGCXGXCXGGACXGG | 111 |
| GAA-IVS1(-163-145) | GCXGXCXAGACXGGGGAGA | 112 |
| GAA-IVS1(-153-135) | GXGXXGCCCXGCXGXCXAG | 113 |
| GAA-IVS2(-173-192) | CXGGAGXACCXGXCACCGXG | 114 |
| GAA-IVS2(-168-192) | CXGGAGXACCXGXCACCGXGGXGXC | 115 |
| GAA-IVS2(-173-197) | GCCXXCXGGAGXACCXGXCACCGXG | 116 |
| GAA-IVS2(-168-187) | GXACCXGXCACCGXGGXGXC | 117 |
| GAA-IVS2(-178-197) | GCCXXCXGGAGXACCXGXCA | 118 |

GAA Exon 2 Antisense Sequences

| Name | Sequence (5'-3') | SEQ ID NO |
|---|---|---|
| GAAEx2A(+202+226) | GGCCCXGGXCXGCXGGCXCCCXGCX | 24 |
| GAAEx2A(+367+391) | GCXCCCXGCAGCCCCXGCXXXGCAG | 25 |

GAA Intron 2 Antisense Sequences

| Name | Sequence (5'-3') | SEQ ID NO |
|---|---|---|
| GAA-IVS2(-4-20) | CCCGCCCCXGCCCXGCC | 10 |
| GAA-IVS2(-14-30) | XGGCCGCCGCCCCCGCCC | 11 |
| GAA-IVS2(-33-52) | XGXCCACGCGCACCCXCXGC | 12 |
| GAA-IVS2(-53-72) | GXGAGGXGCGXGGGXGXCGA | 13 |
| GAA-IVS2(-73-92) | GCAACAXGCACCCCACCCXX | 14 |
| GAA-IVS2(-93-112) | AGGGCCCAGCACACAGXGGX | 15 |
| GAA-IVS2(-113-132) | XCACACCXCCGCXCCCAGCA | 16 |
| GAA-IVS2(-133-150) | GGCGCXGCCAXXGXCXGC | 17 |
| GAA-IVS2(-153-172) | GXGXCCCCACXGCXCCCCGA | 18 |

TABLE 2-continued

Antisense oligomer sequences for GAA-targeted oligomers

| Name | Sequence (5'-3') | SEQ ID NO |
|---|---|---|
| GAA-IVS2(-173-192) | CXGGAGXACCXGXCACCGXG | 19 |
| GAA-IVS2(-193-212) | XGAGCCCCGAGCCCXGCCXX | 20 |
| GAA-IVS2(-213-237) | XGACCCACCXXXXCAXAAAGAXGAA | 21 |
| GAA-IVS2(-234-258) | CXCXGGCAGCCCXACXCXACCXGAC | 22 |
| GAA-IVS2(-338-364) | CXAGXAXAAAXACAXCCCAAAXXXXGC | 23 |
| GAA-IVS2.1.20 | CCCGCCCCXGCCCXGCCCAC | 80 |
| GAA-IVS2.6.20 | CCGCCCCCGCCCCXGCCCXG | 81 |
| GAA-IVS2.9.20 | CCGCCGCCCCGCCCCXGCCC | 82 |
| GAA-IVS2.12.20 | XGGCCGCCGCCCCCGCCCCX | 83 |
| GAA-IVS2.18.20 | CXGCCCXGGCCGCCGCCCCC | 84 |
| GAA-IVS2.24.20 | CACCCXCXGCCCCXGGCCGCC | 85 |
| GAA-IVS2.27.20 | GCGCACCCXCXGCCCXGGCC | 86 |
| GAA-IVS2.40.20 | XGXCGAXGXCCACGCGCACC | 87 |
| GAA-IVS2.45.20 | GXGGGXGXCGAXGXCCACGC | 88 |
| GAA-IVS2.48.20 | XGCGXGGGXGXCGAXGXCCA | 89 |
| GAA-IVS2.54.20 | GXGAGGXGCGXGGGXGXCGA | 90 |
| GAA-IVS2.67.20 | GCACCCCACCCXXGXGAGGX | 91 |
| GAA-IVS2.72.20 | AACAXGCACCCCACCCXXGX | 92 |
| GAA-IVS2.431.20 | AGGAGGAGGACGCCXCCCCC | 93 |
| GAA-IVS2.446.20 | CXCAXCXGCAGAGCCAGGAG | 94 |
| GAA-IVS2.448.20 | CCCXCAXCXGCAGAGCCAGG | 95 |
| GAA-IVS2.450.20 | CXCCCXCAXCXGCAGAGCCA | 96 |
| GAA-IVS2.451.20 | GCXCCCXCAXCXGCAGAGCC | 97 |
| GAA-IVS2.452.20 | GGCXCCCXCAXCXGCAGAGC | 98 |
| GAA-IVS2.453.20 | CGGCXCCCXCAXCXGCAGAG | 99 |
| GAA-IVS2.454.20 | XCGGCXCCCXCAXCXGCAGA | 100 |
| GAA-IVS2.455.20 | CXCGGCXCCCXCAXCXGCAG | 101 |
| GAA-IVS2.456.20 | CCXCGGCXCCCXCAXCXGCA | 102 |
| GAA-IVS2.457.20 | GCCXCGGCXCCCXCAXCXGC | 103 |

For any of the sequences in Table 2, each X is independently selected from thymine (T) or uracil (U)

Certain antisense oligomers thus comprise, consist, or consist essentially of a sequence in Table 1 (e.g., SEQ ID NOS:4-12, 14-103, 105-108, 110-113, and 115-118) or a variant or contiguous or non-contiguous portion(s) thereof. For instance, certain antisense oligomers comprise about or at least about 6, 7, 8, 9, 10, 11, 12, 13, 14, 15, 16, 17, 18, 19, 20, 21, 22, 23, 24, 25, 26, or 27 contiguous or non-contiguous nucleotides of any of SEQ ID NOS:4-12, 14-103, 105-108, 110-113, and 115-118. For non-contiguous portions, intervening nucleotides can be deleted or substituted with a different nucleotide, or intervening nucleotides can be added. Additional examples of variants include oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of SEQ ID NOS: 4-12, 14-103, 105-108, 110-113, and 115-118.

The activity of antisense oligomers and variants thereof can be assayed according to routine techniques in the art. For example, splice forms and expression levels of surveyed RNAs and proteins may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed polynucleotide) from a cell, tissue or organism, and by hybridizing the mRNA/cDNA with a reference polynucleotide that is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

III. Antisense Oligomer Chemistries

A. General Characteristics

Certain antisense oligomers of the instant disclosure specifically hybridize to an intronic splice silencer element or an exonic splice silencer element. Some antisense oligomers comprise a targeting sequence set forth in Table 2, a fragment of at least 10 contiguous nucleotides of a targeting sequence in Table 2, or variant having at least 80% sequence identity to a targeting sequence in Table 2. Specific antisense oligomers consist or consist essentially of a targeting sequence set forth in Table 2. In some embodiments, the oligomer is nuclease-resistant.

In certain embodiments, the antisense oligomer comprises a non-natural chemical backbone selected from a phosphoramidate or phosphorodiamidate morpholino oligomer (PMO), a peptide nucleic acid (PNA), a locked nucleic acid (LNA), a phosphorothioate oligomer, a tricyclo-DNA oligomer, a tricyclo-phosphorothioate oligomer, a 2'O-Me-modified oligomer, or any combination of the foregoing, and a targeting sequence complementary to a region within intron 1 (SEQ ID. NO: 1), intron 2 (SEQ ID. NO: 2), or exon 2 (SEQ ID. NO: 3) of a pre-mRNA of the human acid alpha-glucosidase (GAA) gene. For example, in some embodiments, the targeting sequence is selected from SEQ ID NOS: 4-12, 14-103, 105-108, 110-113, and 115-118, wherein X is selected from uracil (U) or thymine (1').

Antisense oligomers of the disclosure generally comprise a plurality of nucleotide subunits each bearing a nucleobase which taken together form or comprise a targeting sequence, for example, as discussed above. Accordingly, in some embodiments, the antisense oligomers range in length from about 10 to about 40 subunits, more preferably about 10 to 30 subunits, and typically 15-25 subunits. For example, antisense compounds of the disclosure may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subunits in length, or range from 10 subunits to 40 subunits, 10 subunits to 30 subunits, 14 subunits to 25 subunits, 15 subunits to 30 subunits, 17 subunits to 30 subunits, 17 subunits to 27 subunits, 10 subunits to 27 subunits, 10 subunits to 25 subunits, and 10 subunits to 20 subunits. In certain embodiments, the antisense oligomer is about 10 to about 40 or about 5 to about 30 nucleotides in length. In some embodiments, the antisense oligomer is about 14 to about 25 or about 17 to about 27 nucleotides in length.

In some embodiments, the backbone of the antisense oligomer is substantially uncharged, and is optionally recognized as a substrate for active or facilitated transport across the cell membrane. In some embodiments, all the internucleoside linkages are uncharged. The ability of the oligomer to form a stable duplex with the target RNA may also relate to other features of the backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm. Exemplary antisense oligomer targeting sequences are listed in Table 2 (supra).

In certain embodiments, the antisense oligomer has at least one internucleoside linkage that is positively charged or cationic at physiological pH. In some embodiments, the antisense oligomer has at least one internucleoside linkage that exhibits a pKa between about 5.5 and about 12. Optionally, the antisense oligomer has at least one internucleoside linkage with both a basic nitrogen and an alkyl, aryl, or aralkyl group. In particular embodiments, the cationic internucleoside linkage or linkages comprise a 4-aminopiperdin-1-yl (APN) group, or a derivative thereof. While not being bound by any one theory, it is believed that the presence of a cationic linkage or linkages (e.g., APN group or APN derivative) in the oligomer facilitates binding to the negatively charged phosphates in the target nucleotide. Thus, the formation of a heteroduplex between mutant RNA and the cationic linkage-containing oligomer may be held together by both an ionic attractive force and Watson-Crick base pairing.

In some embodiments, the number of cationic linkages is at least 2 and no more than about half the total internucleoside linkages, e.g., about or no more than about 1, 2, 3, 4, 5, 6, 7, 8, 9, 10, 11, 12, 13, 14, 15, 16, 17, 18, 19, 20 cationic linkages. In some embodiments, however, up to all of the internucleoside linkages are cationic linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are cationic linkages. In specific embodiments, an oligomer of about 19-20 subunits may have 2-10, e.g., 4-8, cationic linkages, and the remainder uncharged linkages. In other specific embodiments, an oligomer of 14-15 subunits may have 2-7, e.g., 2, 3, 4, 5, 6, or 7 cationic linkages and the remainder uncharged linkages. The total number of cationic linkages in the oligomer can thus vary from about 1 to 10 to 15 to 20 to 30 or more (including all integers in between), and can be interspersed throughout the oligomer.

In some embodiments, an antisense oligomer may have about or up to about 1 cationic linkage per every 2-5 or 2, 3, 4, or 5 uncharged linkages, such as about 4-5 or 4 or 5 per every 10 uncharged linkages.

Certain embodiments include antisense oligomers that contain about 10%, 15%, 20%, 25%, 30%, 35%, 40%, 45%, 50%, 55%, 60%, 65%, 70%, 75%, 80%, 85%, 90%, 95%, or 100% cationic linkages. In certain embodiments, optimal improvement in antisense activity may be seen if about 25% of the backbone linkages are cationic. In certain embodiments, enhancement may be seen with a small number e.g., 10-20% cationic linkages, or where the number of cationic linkages are in the range 50-80%, such as about 60%.

In some embodiments, the cationic linkages are interspersed along the backbone. Such oligomers optionally contain at least two consecutive uncharged linkages; that is, the oligomer optionally does not have a strictly alternating pattern along its entire length. In specific instances, each one or two cationic linkage(s) is/are separated along the backbone by at least 1, 2, 3, 4, or 5 uncharged linkages.

Also included are oligomers having blocks of cationic linkages and blocks of uncharged linkages. For example, a central block of uncharged linkages may be flanked by blocks of cationic linkages, or vice versa. In some embodiments, the oligomer has approximately equal-length 5', 3' and center regions, and the percentage of cationic linkages in the center region is greater than about 50%, 60%, 70%, or 80% of the total number of cationic linkages.

In certain antisense oligomers, the bulk of the cationic linkages (e.g., 70, 75%, 80%, 90% of the cationic linkages) are distributed close to the "center-region" backbone linkages, e.g., the 6, 7, 8, 9, 10, 11, 12, 13, 14, or 15 centermost linkages. For example, a 16, 17, 18, 19, 20, 21, 22, 23, or 24-mer oligomer with may have at least 50%, 60%, 70%, or 80% of the total cationic linkages localized to the 8, 9, 10, 11, or 12 centermost linkages.

B. Backbone Chemistry Features

The antisense oligomers can employ a variety of antisense chemistries. Examples of oligomer chemistries include, without limitation, peptide nucleic acid (PNA), locked nucleic acid (LNA), phosphorothioate, 2'O-Me-modified oligomers, morpholino, PMO, PPMO, PMOplus, and PMO-X chemistries, including combinations of any of the foregoing. In general, PNA and LNA chemistries can utilize shorter targeting sequences because of their relatively high target binding strength relative to PMO and 2'O-Me oligomers. Phosphorothioate and 2'O-Me-modified chemistries are often combined to generate a 2'O-Me-phosphorothioate backbone. See, e.g., PCT Publication Nos. WO/2013/112053 and WO/2009/008725, incorporated herein by reference in their entireties.

In some instances, antisense oligomers such as PMOs can be conjugated to cell penetrating peptides (CPPs) to facilitate intracellular delivery. Peptide-conjugated PMOs are called PPMOs and certain embodiments include those described in PCT Publication No. WO/2012/150960, incorporated herein by reference in its entirety.

1. Peptide Nucleic Acids (PNAs)

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligomers obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. A non-limiting example of a PNA is depicted below:

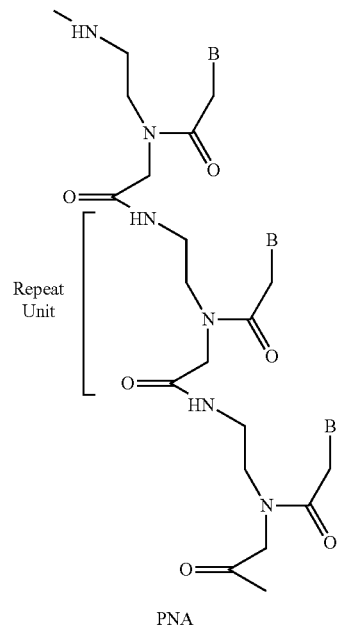

PNA

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969, 766, 7,211,668, 7,022,851, 7,125,994, 7,145,006 and 7,179, 896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

2. Locked Nucleic Acids (LNAs)

Antisense oligomer compounds may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230. A non-limiting example of an LNA is depicted below:

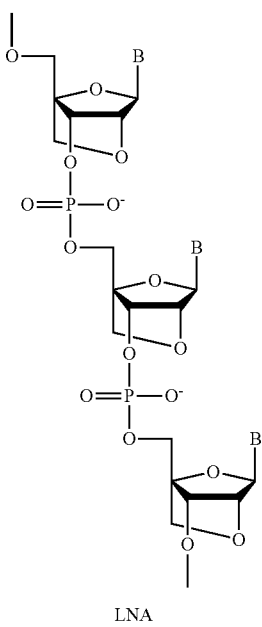

LNA

Compounds of the disclosure may incorporate one or more LNAs; in some cases, the compounds may be entirely composed of LNAs. Methods for the synthesis of individual LNA nucleoside subunits and their incorporation into oligomers are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA containing compound where each LNA subunit is separated by a DNA subunit. Certain compounds are composed of alternating LNA and DNA subunits where the intersubunit linker is phosphorothioate.

3. Phosphorothioates

"Phosphorothioates" (or S-oligos) are a variant of normal DNA in which one of the nonbridging oxygens is replaced by a sulfur. A non-limiting example of a phosphorothioate is depicted below:

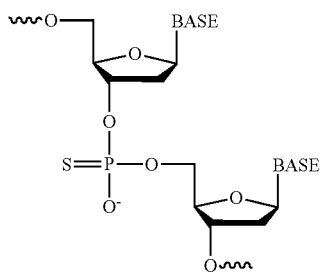

The sulfurization of the internucleotide bond reduces the action of endo- and exonucleases including 5' to 3' and 3' to 5' DNA POL 1 exonuclease, nucleases 51 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990). The latter methods avoid the problem of elemental sulfur's insolubility in most organic solvents and the toxicity of carbon disulfide. The TETD and BDTD methods also yield higher purity phosphorothioates.

4. Triclyclo-DNAs and Tricyclo-Phosphorothioate Nucleotides

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Tricyclo-DNAs and their synthesis are described in International Patent Application Publication No. WO 2010/115993. Compounds of the disclosure may incorporate one or more tricycle-DNA nucleotides; in some cases, the compounds may be entirely composed of tricycle-DNA nucleotides.

Tricyclo-phosphorothioate nucleotides are tricyclo-DNA nucleotides with phosphorothioate intersubunit linkages. Tricyclo-phosphorothioate nucleotides and their synthesis are described in International Patent Application Publication No. WO 2013/053928. Compounds of the disclosure may incorporate one or more tricycle-DNA nucleotides; in some cases, the compounds may be entirely composed of tricycle-DNA nucleotides. A non-limiting example of a tricycle-DNA/tricycle-phophothioate nucleotide is depicted below:

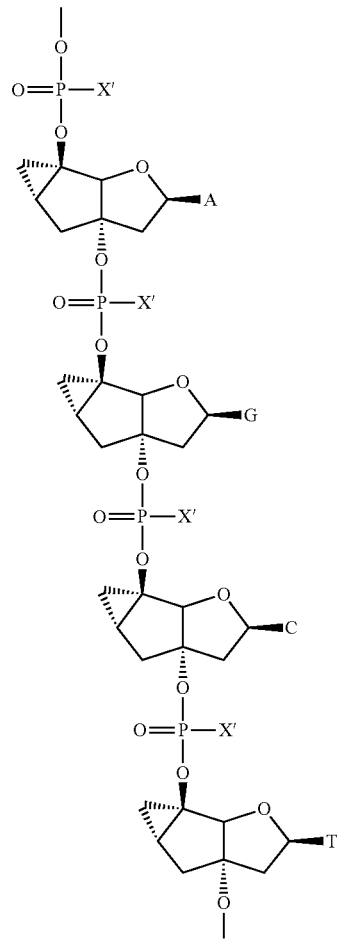

X = O, S

5. 2' O-Methyl oligomers

"2'O-Me oligomers" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphothioate oligomers (PTOs) for further stabilization. 2'O-Me oligomers (phosphodiester or phosphothioate) can be synthesized according to routine techniques in the art (see, e.g., Yoo et al., Nucleic Acids Res. 32:2008-16, 2004). A non-limiting example of a 2' O-Me Oligomer is depicted below:

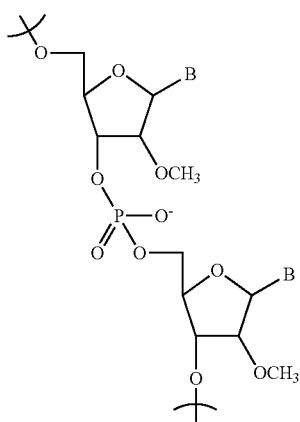

2' O-Me oligomers may also comprise a phosphorothioate linkage (2' O-Me phosphorothioate oligomers).

6. Morpholino Oligomers

A "morpholino oligomer" or "PMO" refers to an oligomer having a backbone which supports a nucleobase capable of hydrogen bonding to typical polynucleotides, wherein the polymer lacks a pentose sugar backbone moiety, but instead contains a morpholino ring. Thus, in a PMO a morpholino ring structure supports a base pairing moiety, to form a sequence of base pairing moieties which is typically designed to hybridize to a selected antisense target in a cell or in a subject being treated. An exemplary "morpholino" oligomer comprises morpholino subunit structures linked together by phosphoramidate or phosphorodiamidate linkages, joining the morpholino nitrogen of one subunit to the 4' exocyclic carbon of an adjacent subunit, each subunit comprising a purine or pyrimidine nucleobase effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication numbers WO/2009/064471 and WO/2012/043730, all of which are incorporated herein by reference in their entirety.

Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of the PMO and/or PMO-X oligomers described herein, one nitrogen is always pendant to the backbone chain. The second nitrogen, in a phosphorodiamidate linkage, is typically the ring nitrogen in a morpholino ring structure.

"PMO-X" refers to phosporodiamidate morpholino oligomers (PMOs) having a phosphorus atom with (i) a covalent bond to the nitrogen atom of a morpholino ring and (ii) a second covalent bond to the ring nitrogen of a 4-aminopiperdin-1-yl (i.e., APN) or a derivative of 4-aminopiperdin-1-yl. Exemplary PMO-X oligomers are disclosed in PCT application No. PCT/US2011/38459 and PCT Publication No. WO/2013/074834, each of which is herein incorporated by reference in its entirety. "PMO-apn" or "APN" refers to a PMO-X oligomer which comprises at least one internucleoside linkage where a phosphorus atom is linked to a morpholino group and to the ring nitrogen of a 4-aminopiperdin-1-yl (i.e., APN). In specific embodiments, an antisense oligomer comprising a targeting sequence as set forth in Table 2 comprises at least one APN-containing linkage or APN derivative-containing linkage. Specific embodiments include PMOs that have about 10%, 15%, 20%, 25%, 30%, 35%, 40%, 45%, 50%, 55%, 60%, 65%, 70%, 75%, 80%, 85%, 90%, 95%, or 100% APN/APN derivative-containing linkages, where the remaining linkages (if less than 100%) are uncharged linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are APN/APN derivative-containing linkages.

In some embodiments, the antisense oligomer is a compound of formula (I):

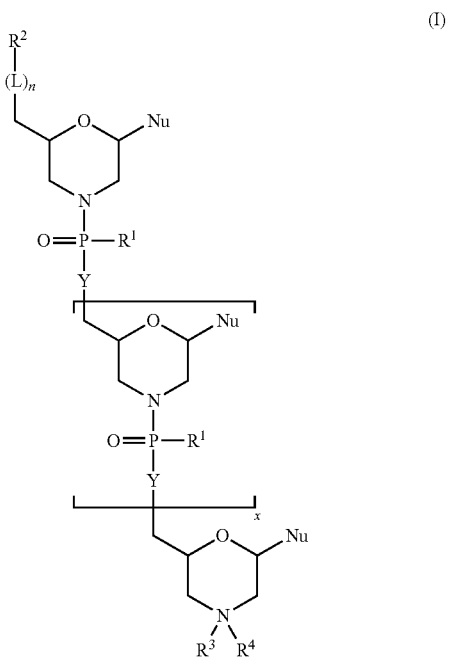

or a pharmaceutically acceptable salt thereof, wherein:

each Nu is a nucleobase which taken together forms a targeting sequence;

x is an integer from 8 to 38;

each Y is independently selected from O or —NR$^a$, wherein R$^a$ is selected from the group consisting of hydrogen, -T$^1$-NR$^c$R$^d$R$^e$, and —[(C(O)CHR'NH)$_m$]R", wherein:

R' is a side chain of a naturally occurring amino acid or a one- or two-carbon homolog thereof, R" is selected from Hydrogen or acyl, m is an integer from 1 to 60, R$^c$ is selected from the group consisting of hydrogen, C$_1$-C$_6$ alkyl, aralkyl, and —C(=NH)NH$_2$, R$^d$ is selected from the group consisting of hydrogen, aralkyl, and C$_1$-C$_6$ alkyl, or R$^c$ and R$^d$ taken together with the nitrogen atom to which they are attached form a 5-7 membered ring when R$^c$ and R$^d$ are each independently C$_1$-C$_6$ alkyl or aralkyl, where the ring is optionally substituted with a substituent selected from the group consisting of C$_1$-C$_6$ alkyl, phenyl, halogen, and aralkyl, and R$^e$ is selected from the group consisting of an electron pair, hydrogen, C$_1$-C$_6$ alkyl, and aralkyl;

each L is independently selected from the group consisting of —P(O)$_2$OH—, —P(O)$_2$R$^1$—, —P(O)$_2$(N(CH$_3$)$_3$—N(CH$_3$)CH$_2$C(O)NH$_2$, a piperazinyl group, a carbonyl group, H(O(CH$_2$)$_s$O)$_w$—, —(OCH$_2$CH$_2$O)$_w$, and —[(C(O)CHR'NH)$_m$]R", wherein w is an integer selected from 3-20, S is an integer selected from 1 to 8;

n is an integer from 0 to 3;

each R' is independently selected from the group consisting of —N(CH$_3$)$_2$, —NR$^5$R$^6$, —OR$^7$, a moiety of formula (II):

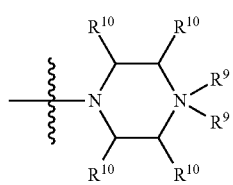

(II)

wherein R$^8$ is selected from the group consisting of hydrogen, methyl, —C(=NH)NH$_2$, —Z-T$^2$-NHC(=NH)NH$_2$, and —[(C(O)CHR'NH)$_m$]R", where Z is carbonyl or a direct bond, R$^9$ is selected from the group consisting of an electron pair, hydrogen, a C$_1$-C$_6$ alkyl, and aralkyl, and each R$^{10}$ is independently selected from hydrogen or methyl; and a moiety of formula (III):

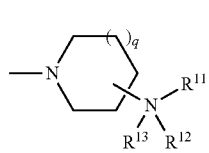

(III)

wherein q is an integer from 0 to 2, R$^{11}$ is selected from the group consisting of hydrogen, C$_1$-C$_6$alkyl, aralkyl, and —C(=NH)NH$_2$, R$^{12}$ is selected from the group consisting of hydrogen, aralkyl, and C$_1$-C$_6$ alkyl, or R$^{11}$ and R$^{12}$ taken together with the nitrogen atom to which they are attached form a 5-7 membered ring where the ring is optionally substituted with a substituent selected from the group consisting of C$_1$-C$_6$ alkyl, phenyl, halogen, and aralkyl, and R$^{13}$ is selected from the group consisting of an electron pair, hydrogen, C$_1$-C$_6$ alkyl, and aralkyl;

R$^2$ is selected from the group consisting of hydrogen, OH, a nucleotide, —(CH$_2$)$_m$C(O)NR$^f$R$^g$ wherein R$^f$ and R$^g$ are independently selected from H, acyl, C$_1$-C$_6$ alkyl, and —[(C(O)CHR'NH)$_m$]R", —[(C(O)CHR'NH)$_m$]R", H(O(CH$_2$)$_s$O)$_w$—, H(OCH$_2$CH$_2$O)$_w$—, trityl, —C(=O)OR$^f$, and acyl, wherein R$^f$ is C$_1$-C$_{30}$ alkyl comprising one or more oxygen or hydroxyl moieties or combinations thereof, or R$^2$ is absent;

R$^3$ is selected from the group consisting of hydrogen, a C$_1$-C$_6$ alkyl, a nucleotide, —[(C(O)CHR'NH)$_m$]R", —C(=NH)NH$_2$, trityl, —C(=O)OR$^g$, acyl, —C(O)(CH$_2$)$_m$C(O), and T$^4$-(4-(4,6-(NR$_2$)-1,3,5-triazin-2-yl)piperazin-1-yl, wherein R$^g$ is C$_1$-C$_{30}$ alkyl comprising one or more oxygen or hydroxyl moieties or combinations thereof, T$^4$ is selected from —C(O)(CH$_2$)$_6$C(O)— or —C(O)(CH$_2$)$_2$S$_2$(CH$_2$)$_2$C(O)—, and R is —(CH$_2$)OC(O)NH(CH$_2$)$_6$NHC(NH)NH$_2$;

R$^4$ is selected from the group consisting of an electron pair, hydrogen, a C$_1$-C$_6$ alkyl, and acyl, and each R$^5$ is independently selected from hydrogen or methyl;

each R$^6$ and each R$^7$ is independently selected from hydrogen or -T3-NR$^c$R$^d$R$^e$; and each of T$^1$, T$^2$, and T$^3$ is independently an optional linker of up to 18 atoms in length comprising alkyl, alkoxy, or alkylamino groups, or combinations thereof, wherein the targeting sequence is complementary to a region within intron 1 (SEQ ID. NO. 1), intron 2 (SEQ ID. NO. 2), or exon 2 (SEQ ID. NO. 3) of a pre-mRNA of the human acid alpha-glucosidase (GAA) gene.

In some embodiments, R$^3$ is a moiety T$^4$-(4-(4,6-(NR$_2$)-1,3,5-triazin-2-yl)piperazin-1-yl, wherein T$^4$ is selected from —C(O)(CH$_2$)$_6$C(O)— or —C(O)(CH$_2$)$_2$S$_2$(CH$_2$)$_2$C(O)—, and R is —(CH$_2$)OC(O)NH(CH$_2$)$_6$NHC(NH)NH$_2$. Such moieties are further described in U.S. Pat. No. 7,935,816 incorporated herein by reference in its entirety.

In certain embodiments, R$^3$ may comprise a moiety depicted below:

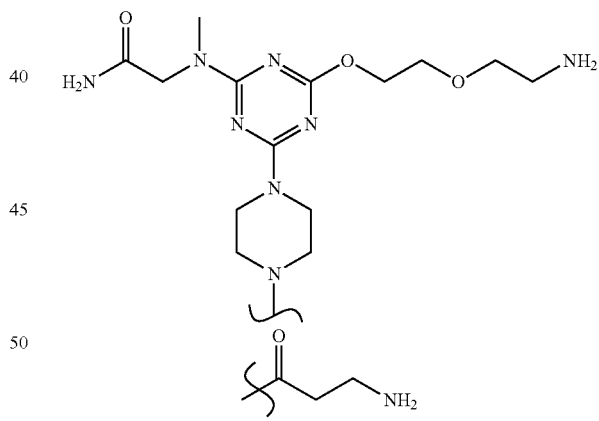

In certain embodiments, each R' is —N(CH$_3$)$_2$. In some embodiments, about 50-90% of the R$_1$ groups are dimethylamino (i.e. —N(CH$_3$)$_2$). In certain embodiments, about 66% of the R$_1$ groups are dimethylamino.

In some embodiments, the targeting sequence is selected from SEQ. ID NOS: 4-12, 14-103, 105-108, 110-113, 115-118, wherein X is selected from uracil (U) or thymine (1').

In some embodiments, each R' is —N(CH$_3$)$_2$ and the targeting sequence is selected from SEQ. ID NOS: 4-12, 14-103, 105-108, 110-113, 115-118, wherein X is selected from uracil (U) or thymine (T).

In some embodiments of the disclosure, R$_1$ may be selected from the group consisting of:

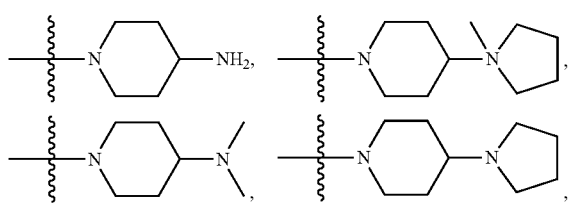
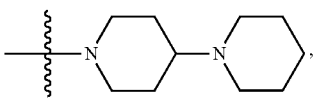
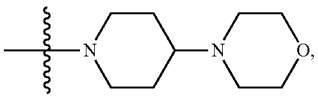
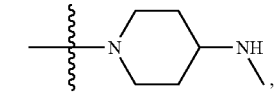
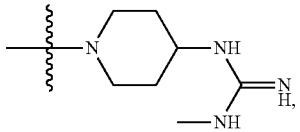
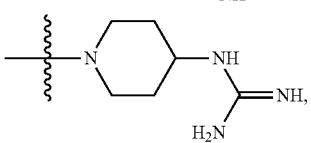
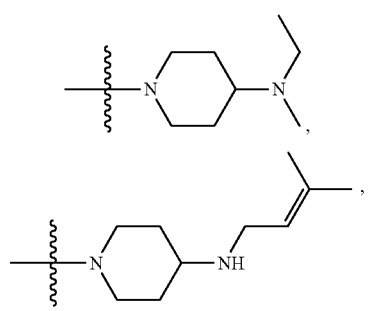
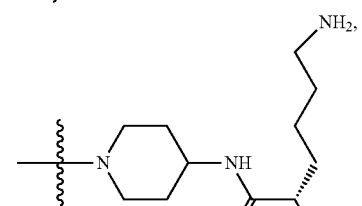
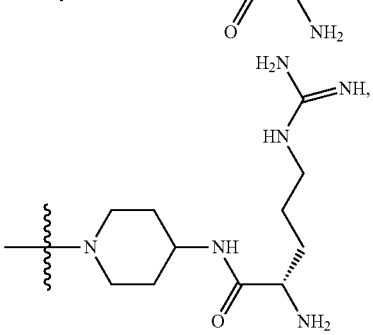
-continued
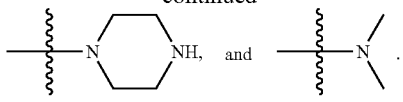
In some embodiments, at least one $R^1$ is:
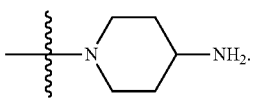
In certain embodiments, n is 2, $R^2$ and L taken together are of the formula:
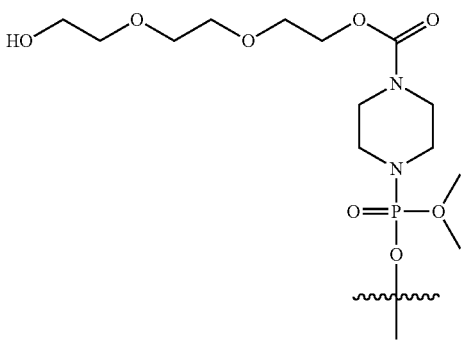
and Y is O at each occurrence.
In other embodiments, the antisense oligomer is a compound of formula (IV):
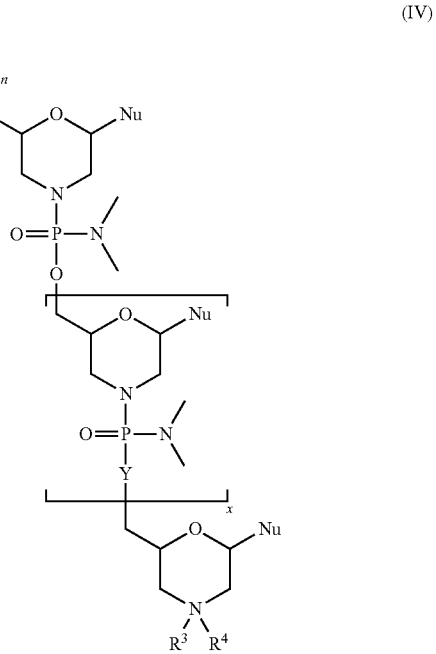
(IV)
or a pharmaceutically acceptable salt thereof, wherein:
each Nu is a nucleobase which taken together forms a targeting sequence;

x is an integer from 8 to 38;

each L is independently selected from the group consisting of —P(O)$_2$OH—, —P(O)$_2$R$^1$—, —P(O)$_2$(N(CH$_3$)$_3$—N(CH$_3$)CH$_2$C(O)NH$_2$, a piperazinyl group, a carbonyl group, H(O(CH$_2$)$_s$O)$_w$—, —(OCH$_2$CH$_2$O)$_w$—, and —[(C(O)CHR'NH)$_m$]R", wherein w is an integer selected from 3-20, S is an integer selected from 1 to 8, R' is a side chain of a naturally occurring amino acid or a one- or two-carbon homolog thereof, R" is selected from Hydrogen or acyl, m is an integer from 1 to 60;

n is an integer from 0 to 3;

R$^2$ is selected from the group consisting of hydrogen, OH, a nucleotide, —(CH$_2$)$_m$C(O)NR$^f$R$^g$ wherein R$^f$ and R$^g$ are independently selected from H, acyl, C$_1$-C$_6$ alkyl, and —[(C(O)CHR'NH)$_m$]R", —[(C(O)CHR'NH)$_m$]R", H(O(CH$_2$)$_s$O)$_w$—, H(OCH$_2$CH$_2$O)$_w$—, trityl, —C(=O)OR$^f$, and acyl, wherein R$^f$ is C$_1$-C$_{30}$ alkyl comprising one or more oxygen or hydroxyl moieties or combinations thereof, or R$^2$ is absent;

R$^3$ is selected from the group consisting of hydrogen, a C$_1$-C$_6$ alkyl, a nucleotide, —[(C(O)CHR'NH)$_m$]R", —C(=NH)NH$_2$, and acyl; and R$^4$ is selected from the group consisting of an electron pair, hydrogen, a C$_1$-C$_6$ alkyl, and acyl, wherein the targeting sequence is complementary to a region within intron 1 (SEQ ID. NO: 1), intron 2 (SEQ ID. NO: 2), or exon 2 (SEQ ID. NO: 3) of a pre-mRNA of the human acid alpha-glucosidase (GAA) gene.

In some embodiments, n is 2; R$^2$ and L taken together are of the formula:

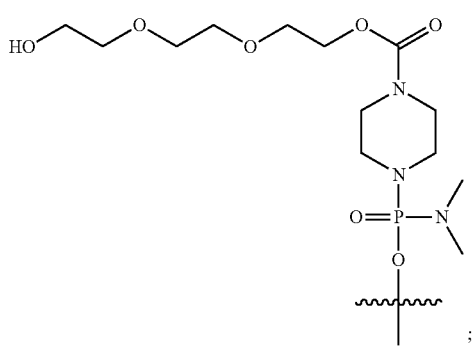

R$^3$ is hydrogen; and R$^4$ is an electron pair.

In some embodiments, the antisense oligomer is a compound of formula (V):

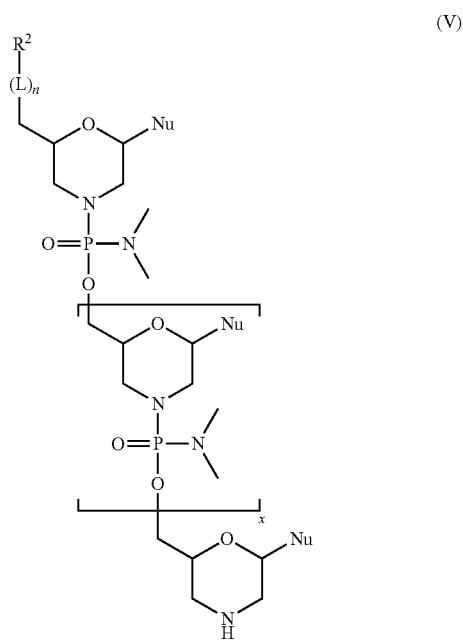

(V)

or a pharmaceutically acceptable salt thereof, wherein:

each Nu is a nucleobase which taken together forms a targeting sequence;

x is an integer from 8 to 38; each L is independently selected from the group consisting of —P(O)$_2$OH—, —P(O)$_2$R$^1$—, —P(O)$_2$(N(CH$_3$)$_3$—N(CH$_3$)CH$_2$C(O)NH$_2$, a piperazinyl group, a carbonyl group, H(O(CH$_2$)$_s$O)$_w$—, —(OCH$_2$CH$_2$O)$_w$, and —[(C(O)CHR'NH)$_m$]R", wherein w is an integer selected from 3-20, S is an integer selected from 1 to 8, R' is a side chain of a naturally occurring amino acid or a one- or two-carbon homolog thereof, R" is selected from Hydrogen or acyl, and m is an integer from 1 to 60;

n is an integer from 0 to 3; and

R$^2$ is selected from the group consisting of hydrogen, OH, a nucleotide, —(CH$_2$)$_m$C(O)NR$^f$R$^g$ wherein R$^f$ and R$^g$ are independently selected from H, acyl, C$_1$-C$_6$ alkyl, and —[(C(O)CHR'NH)$_m$]R", —[(C(O)CHR'NH)$_m$]R", H(O(CH$_2$)$_s$O)$_w$—, H(OCH$_2$CH$_2$O)$_w$—, trityl, —C(=O)OR$^f$, and acyl, wherein R$^f$ is C$_1$-C$_{30}$ alkyl comprising one or more oxygen or hydroxyl moieties or combinations thereof, or R$^2$ is absent, wherein the targeting sequence is complementary to a region within intron 1 (SEQ ID. NO: 1), intron 2 (SEQ ID. NO: 2), or exon 2 (SEQ ID. NO: 3) of a pre-mRNA of the human acid alpha-glucosidase (GAA) gene.

In some embodiments, n is 2; and
R² and L taken together are of the formula:

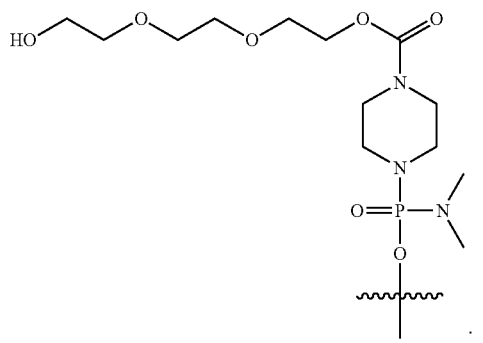

In certain embodiments, the antisense oligomer of the disclosure is a compound of formula (VI):

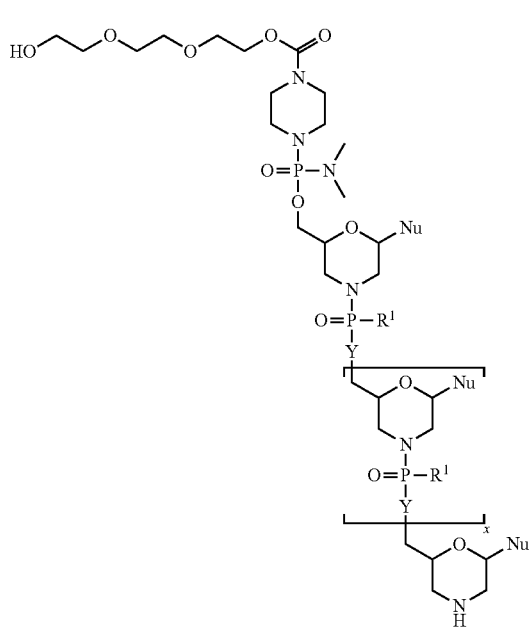

(VI)

or a pharmaceutically acceptable salt thereof, wherein:
each Nu is a nucleobase which taken together form a targeting sequence;
x is an integer from 15 to 25;
each Y is O;
each R' is independently selected from the group consisting of:

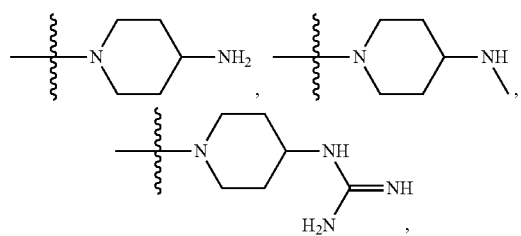

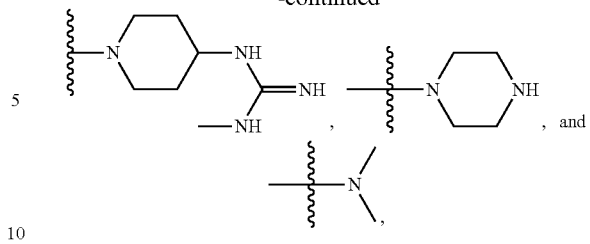

wherein at least one $R^1$ is —N(CH$_3$)$_2$, and
wherein the targeting sequence is selected from SEQ ID NOS: 4-12, 14-103, 105-108, 110-113, and 115-118, wherein X is selected from uracil (U) or thymine (T). In some embodiments, each $R^1$ is —N(CH$_3$)$_2$.

In some embodiments, each Nu of the antisense oligomers of the disclosure, including compounds of formula (I), (IV), (V), and (VI), is independently selected from the group consisting of adenine, guanine, thymine, uracil, cytosine, hypoxanthine, 2,6-diaminopurine, 5-methyl cytosine, C$_5$-propynyl-modified pyrimidines, and 9-(aminoethoxy) phenoxazine. In some embodiments, the targeting sequence of the antisense oligomers of the disclosure, including compounds of formula (I), (IV), (V), and (VI), is selected from SEQ. ID NOS: 4-12, 14-103, 105-108, 110-113, and 115-118, wherein X is selected from uracil (U) or thymine (T).

In certain embodiments, the antisense oligomer is a compound of formula (VII):

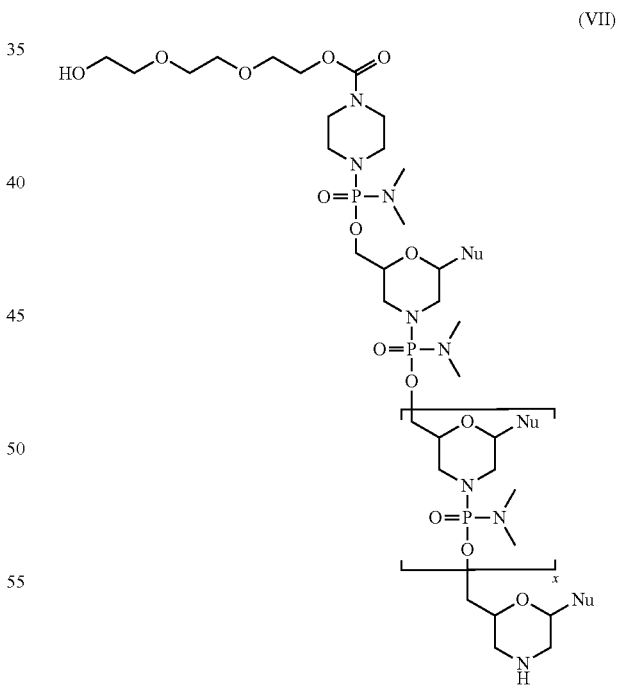

(VII)

or a pharmaceutically acceptable salt thereof, wherein:
each Nu is a nucleobase which taken together form a targeting sequence; and
x is an integer from 8 to 38;
wherein the targeting sequence is selected from SEQ ID NOS: 4-12, 14-103, 105-108, 110-113, and 115-118, wherein X is selected from uracil (U) or thymine (1).

Additional antisense oligomers/chemistries that can be used in accordance with the present disclosure include those described in the following patents and patent publications, the contents of which are incorporated herein by reference: PCT Publication Nos. WO/2007/002390; WO/2010/120820; and WO/2010/148249; U.S. Pat. No. 7,838,657; and U.S. Application No. 2011/0269820.

C. The Preparation of PMO-X with Basic Nitrogen Internucleoside Linkers

Morpholino subunits, the modified intersubunit linkages, and oligomers comprising the same can be prepared as described, for example, in U.S. Pat. Nos. 5,185,444, and 7,943,762, which are incorporated by reference in their entireties. The morpholino subunits can be prepared according to the following general Reaction Scheme I.

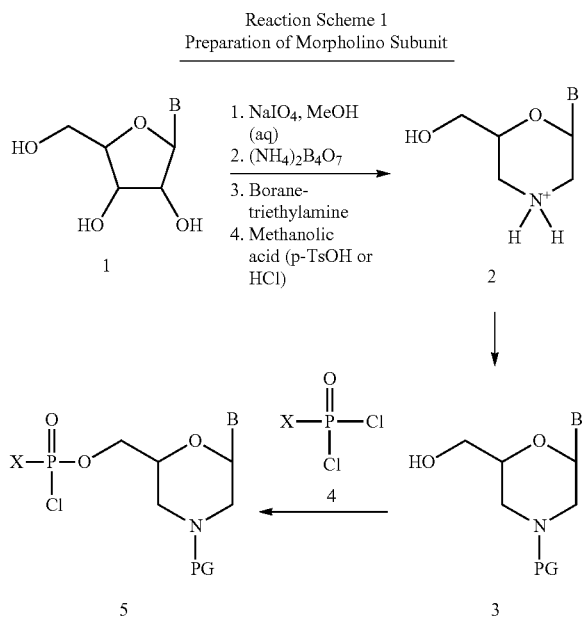

Referring to Reaction Scheme 1, wherein B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitably protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271,040, which is hereby incorporated by reference in its entirety.

Reaction of 3 with the activated phosphorous compound 4, results in morpholino subunits having the desired linkage moiety 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762.

Figure 2:
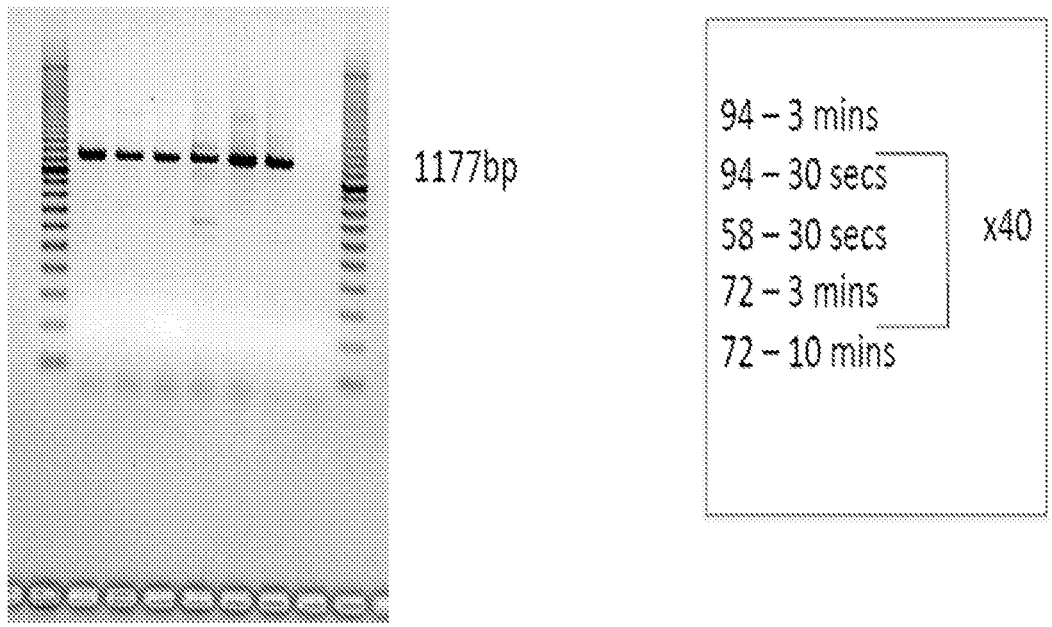
FIG. 2 shows the ~1177 base PCR amplification product from the wild-type GAA gene containing exon 2, using primers directed to exon1(forward) and exon3(reverse) (see Example 2).

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$. An exemplary method is demonstrated in FIGS. 1 and 2. Once supported, the protecting group (e.g., trityl) is removed and the free amine is reacted with an activated phosphorous moiety of a second compound of structure 5. This sequence is repeated until the desired length of oligo is obtained. The protecting group in the terminal 5' end may either be removed or left on if a 5% modification is desired. The oligo can be removed from the solid support using any number of methods, for example treatment with DTT followed by ammonium hydroxide as depicted in FIGS. 3 and 4.

The preparation of modified morpholino subunits and morpholino oligomers are described in more detail in the Examples. The morpholino oligomers containing any number of modified linkages may be prepared using methods described herein, methods known in the art and/or described by reference herein. Also described in the examples are global modifications of morpholino oligomers prepared as previously described (see e.g., PCT publication WO2008036127).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts.

For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

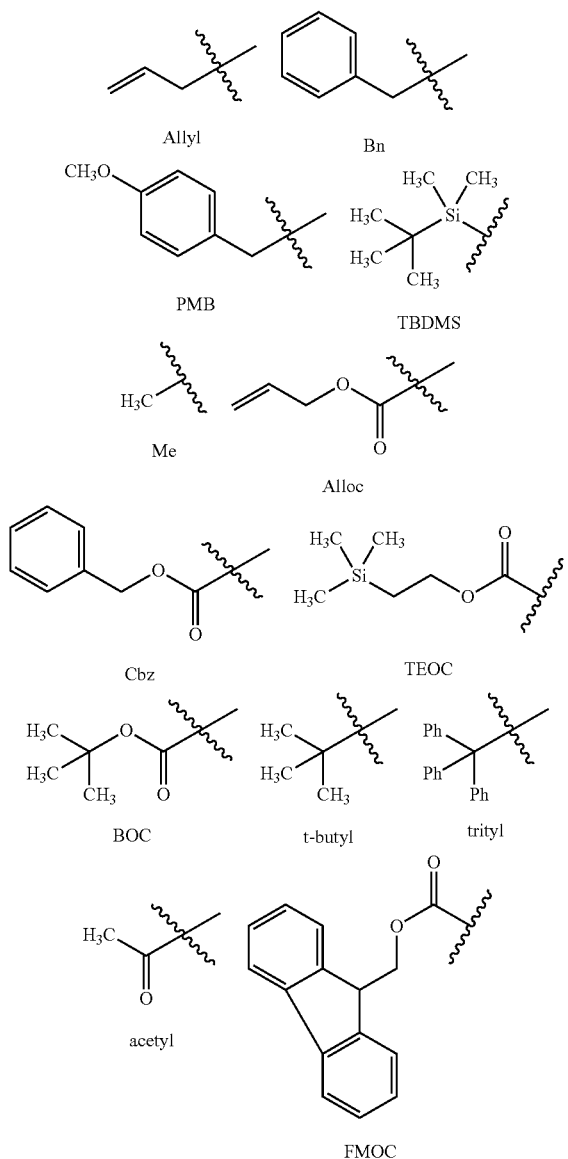

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO, PMO+, PPMO, and PMO-X containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detritylation step is omitted.

IV. Formulations

The compounds of the disclosure may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the disclosure encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the disclosure, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomers of the disclosure are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the disclosure: i.e., salts that retain the desired biological activity of the parent compound and do not impart undesired toxicological effects thereto. For oligomers, examples of pharmaceutically acceptable salts and their uses are further described in U.S. Pat. No. 6,287,860, which is incorporated herein in its entirety.

The present disclosure also includes pharmaceutical compositions and formulations which include the antisense compounds of the disclosure. The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, gel capsules, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present disclosure include, but are not limited to, solutions, emulsions, foams and liposome-containing formulations. The pharmaceutical compositions and formulations of the present disclosure may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present disclosure. Emulsions and their uses are well known in the art and are further described in U.S. Pat. No. 6,287,860, which is incorporated herein in its entirety.

Formulations of the present disclosure include liposomal formulations. As used in the present disclosure, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present disclosure may also include surfactants. The use of surfactants in drug products, formulations and in emulsions is well known in the art. Surfactants and their uses are further described in U.S. Pat. No. 6,287,860, which is incorporated herein in its entirety.

In some embodiments, the present disclosure employs various penetration enhancers to effect the efficient delivery of nucleic acids, particularly oligomers. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860, which is incorporated herein in its entirety. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860, which is incorporated herein in its entirety. Oral formulations for oligomers and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the disclosure provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxyco-formycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the disclosure, such chemotherapeutic agents may be used individually (e.g., 5-FU and oligomer), sequentially (e.g., 5-FU and oligomer for a period of time followed by MTX and oligomer), or in combination with one or more other such chemotherapeutic agents (e.g., 5-FU, MTX and oligomer, or 5-FU, radiotherapy and oligomer). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the disclosure. Combinations of antisense compounds and other non-antisense drugs are also within the scope of this disclosure. Two or more combined compounds may be used together or sequentially.

In another related embodiment, compositions of the disclosure may contain one or more antisense compounds, particularly oligomers, targeted to a first nucleic acid and one or more additional antisense compounds targeted to a second nucleic acid target. Alternatively, compositions of the disclosure may contain two or more antisense compounds targeted to different regions of the same nucleic acid target. Numerous examples of antisense compounds are known in the art. Two or more combined compounds may be used together or sequentially.

V. Methods of Use

Certain embodiments relate to methods of increasing expression of exon 2-containing GAA mRNA and/or protein using the antisense oligomers of the present disclosure for therapeutic purposes (e.g., treating subjects with GSD-II). Accordingly, in some embodiments, the present disclosure provides methods of treating an individual afflicted with or at risk for developing GSD-II, comprising administering an effective amount of an antisense oligomer of the disclosure to the subject. In some embodiments, the antisense oligomer comprising a nucleotide sequence of sufficient length and complementarity to specifically hybridize to a region within the pre-mRNA of the acid alpha-glucosidase (GAA) gene, wherein binding of the antisense oligomer to the region increases the level of exon 2-containing GAA mRNA in a cell and/or tissue of the subject. Exemplary antisense targeting sequences are shown in Table 2.

Also included are antisense oligomers for use in the preparation of a medicament for the treatment of glycogen storage disease type II (GSD-II; Pompe disease), comprising a nucleotide sequence of sufficient length and complementarity to specifically hybridize to a region within the pre-mRNA of the acid alpha-glucosidase (GM) gene, wherein binding of the antisense oligomer to the region increases the level of exon 2-containing GAA mRNA.

In some embodiments of the method of treating GSD-II or the medicament for the treatment of GSD-II, the antisense oligomer compound comprises:

a non-natural chemical backbone selected from a phosphoramidate or phosphorodiamidate morpholino oligomer (PMO), a peptide nucleic acid (PNA), a locked nucleic acid (LNA), a phosphorothioate oligomer, a tricyclo-DNA oligomer, a tricyclo-phosphorothioate oligomer, a 2'O-Me-modified oligomer, or any combination of the foregoing; and a targeting sequence complementary to a region within intron 1 (SEQ ID. NO: 1), intron 2 (SEQ ID. NO: 2), or exon 2 (SEQ ID. NO: 3) of a pre-mRNA of the human acid alpha-glucosidase (GAA) gene.

As noted above, "GSD-II" refers to glycogen storage disease type II (GSD-II or Pompe disease), a human autosomal recessive disease that is often characterized by under expression of GAA protein in affected individuals. Included are subjects having infantile GSD-II and those having late onset forms of the disease.

In certain embodiments, a subject has reduced expression and/or activity of GAA protein in one or more tissues (for example, relative to a healthy subject or an earlier point in time), including heart, skeletal muscle, liver, and nervous system tissues. In some embodiments, the subject has increased accumulation of glycogen in one or more tissues (for example, relative to a healthy subject or an earlier point in time), including heart, skeletal muscle, liver, and nervous system tissues. In specific embodiments, the subject has at least one IVS1-13T>G mutation (also referred to as c.336-13T>G), possibly in combination with other mutation(s) that leads to reduced expression of functional GAA protein. A summary of molecular genetic testing used in GSD-II is shown in Table 3 below.

TABLE 3

| Gene Symbol | Test Method | Mutations Detected | Mutation Detection Frequency by Test Method | Test Availability |
|---|---|---|---|---|
| GAA | Sequence analysis | p.Arg854* | ~50%-60% | Clinical |
|  |  | p.Asp645Glu | ~40%-80% |  |
|  |  | IVS1-13T > G | ~50%-85% |  |

TABLE 3-continued

| Gene Symbol | Test Method | Mutations Detected | Mutation Detection Frequency by Test Method | Test Availability |
|---|---|---|---|---|
| | | Other sequence variants in the gene | 83%-93% | |
| | Sequence analysis of select exons | Sequence variants in the select exons | 83%-93% | |
| | Targeted mutation analysis | Sequence variants in targeted sites | 100% of for variants among the targeted mutations | |
| | Deletion/duplication analysis | Exonic and whole-gene deletions/duplications | 5%-13% | |

Certain embodiments relate to methods of increasing expression of exon 2-containing GAA mRNA or protein in a cell, tissue, and/or subject, as described herein. In some instances, exon-2 containing GAA mRNA or protein is increased by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject, a control composition without the antisense oligomer, the absence of treatment, and/or an earlier time-point. Also included are methods of maintaining the expression of containing GAA mRNA or protein relative to the levels of a healthy control.

Some embodiments relate to methods of increasing expression of functional/active GAA protein a cell, tissue, and/or subject, as described herein. In certain instances, the level of functional/active GAA protein is increased by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject, a control composition without the antisense oligomer, the absence of treatment, and/or an earlier time-point. Also included are methods of maintaining the expression of functional/active GAA protein relative to the levels of a healthy control.

Particular embodiments relate to methods of reducing the accumulation of glycogen in one or more cells, tissues, and/or subjects, as described herein. In certain instances, the accumulation of glycogen is reduced by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject, a control composition without the antisense oligomer, the absence of treatment, and/or an earlier time-point. Also included are methods of maintaining normal or otherwise healthy glycogen levels in a cell, tissue, and/or subject (e.g., asymptomatic levels or levels associated with reduced symptoms of GSD-II).

Also included are methods of reducing one or more symptoms of GSD-II in a subject in need thereof. Particular examples include symptoms of infantile GSD-II such as cardiomegaly, hypotonia, cardiomyopathy, left ventricular outflow obstruction, respiratory distress, motor delay/muscle weakness, and feeding difficulties/failure to thrive. Additional examples include symptoms of late onset GSD-II such as muscle weakness (e.g., skeletal muscle weakness including progressive muscle weakness), impaired cough, recurrent chest infections, hypotonia, delayed motor milestones, difficulty swallowing or chewing, and reduced vital capacity or respiratory insufficiency.

The antisense oligomers of the disclosure can be administered to subjects to treat (prophylactically or therapeutically) GSD-II. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. Vascular or extravascular circulation, the blood or lymph system, and the cerebrospinal fluid are some non-limiting sites where the RNA may be introduced. Direct CNS delivery may be employed, for instance, intracerebral ventribular or intrathecal administration may be used as routes of administration.

In particular embodiments, the antisense oligomer(s) are administered to the subject by intramuscular injection (IM), i.e., they are administered or delivered intramuscularly. Non-limiting examples of intramuscular injection sites include the deltoid muscle of the arm, the vastus lateralis muscle of the leg, and the ventrogluteal muscles of the hips, and dorsogluteal muscles of the buttocks. In specific embodiments, a PMO, PMO-X, or PPMO is administered by IM.

In certain embodiments, the subject in need thereof as glycogen accumulation in central nervous system tissues. Examples include instances where central nervous system pathology contributes to respiratory deficits in GSD-II (see, e.g., DeRuisseau et al., PNAS USA. 106:9419-24, 2009). Accordingly, the antisense oligomers described herein can be delivered to the nervous system of a subject by any art-recognized method, e.g., where the subject has GSD-II with involvement of the CNS. For example, peripheral blood injection of the antisense oligomers of the disclosure can be used to deliver said reagents to peripheral neurons via diffusive and/or active means. Alternatively, the antisense oligomers can be modified to promote crossing of the blood-brain-barrier (BBB) to achieve delivery of said reagents to neuronal cells of the central nervous system (CNS). Specific recent advancements in antisense oligomer technology and delivery strategies have broadened the scope of antisense oligomer usage for neuronal disorders (see, e.g., Forte, A., et al. 2005. Curr. Drug Targets 6:21-29; Jaeger, L. B., and W. A. Banks. 2005. Methods Mol. Med. 106:237-251; Vinogradov, S. V., et al. 2004. Bioconjug. Chem. 5:50-60; the foregoing are incorporated herein in their entirety by reference). For example, the antisense oligomers of the disclosure can be generated as peptide nucleic acid (PNA) compounds. PNA reagents have each been identified to cross the BBB (Jaeger, L. B., and W. A. Banks. 2005. Methods Mol. Med. 106:237-251). Treatment of a subject with, e.g., a vasoactive agent, has also been described to promote transport across the BBB (Id). Tethering of the antisense oligomers of the disclosure to agents that are actively transported across the BBB may also be used as a delivery mechanism. Administration of antisense agents together with contrast agents such as iohexol (e.g., separately, concurrently, in the same formulation) can also facilitate delivery across the BBB, as described in PCT Publication No. WO/2013/086207, incorporated by reference in its entirety.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, the contents of which are incorporated in their entirety by reference herein.

The antisense oligomers described herein may also be delivered via an implantable device. Design of such a device is an art-recognized process, with, e.g., synthetic implant design described in, e.g., U.S. Pat. No. 6,969,400, the contents of which are incorporated in their entirety by reference herein.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions The compounds (e.g., antisense oligomers) of the present disclosure may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers of the disclosure. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, the antisense oligomer is administered to a mammalian subject, e.g., human or domestic animal, exhibiting the symptoms of a lysosomal storage disorder, in a suitable pharmaceutical carrier. In one aspect of the method, the subject is a human subject, e.g., a patient diagnosed as having GSD-II (Pompe disease). In one preferred embodiment, the antisense oligomer is contained in a pharmaceutically acceptable carrier, and is delivered orally. In another preferred embodiment, the oligomer is contained in a pharmaceutically acceptable carrier, and is delivered intravenously (i.v.).

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligomers of the disclosure may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate for the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer of the disclosure may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

In some embodiments, the antisense oligomer is actively taken up by mammalian cells. In further embodiments, the antisense oligomer may be conjugated to a transport moiety (e.g., transport peptide or CPP) as described herein to facilitate such uptake.

VI. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 µg to 100 g per kg of body weight, once or more daily, to once every 20 years.

While the present disclosure has been described with specificity in accordance with certain of its embodiments, the following examples serve only to illustrate the disclosure and are not intended to limit the same. Each of the references, patents, patent applications, GenBank accession numbers, and the like recited in the present application are incorporated herein by reference in its entirety.

VII. Examples

Example 1

Design of Antisense Targeting Sequences

Antisense oligomer targeting sequences were designed for therapeutic splice-switching applications related to the IVS1-13T>G mutation in the human GAA gene. Here, it is expected that splice-switching oligomers will suppress intronic and exonic splice silencer elements (ISS and ESS elements, respectively) and thereby promote exon 2 retention in the mature GAA mRNA. Restoration of normal or near-normal GAA expression would then allow functional enzyme to be synthesized, thereby providing a clinical benefit to GSD-II patients.

Certain antisense targeting sequences were thus designed to mask splice silencer elements, either within exon 2 of the GAA gene or within its flanking introns. Non-limiting examples of potential silencer element targets include hnRNPA1 motifs (TAGGGA), Tra2-β motifs, and 9G8 motifs. In silico secondary structure analysis (mFold) of introns 1 and 2 (IVS1 and IVS2, respectively) mRNAs was also employed to identify long distance interactions that could provide suitable antisense target sequences. The antisense targeting sequences resulting from this analysis are shown in Table 2 (see also SEQ ID NOS:4-12, 14-103, 105-108, 110-113, and 115-118).

Exemplary oligomers comprising a targeting sequence as set forth in Table 2 are prepared in this example as 2'-O-methyl modified antisense oligomers having a phosphorothioate backbone. These antisense oligomers are complexed with a cationic delivery agent (Lipofectamine 2000, Lipofectin or similar) and transfected into GSD-II patient-derived fibroblasts and/or lymphocytes carrying the IVS1-13T>G mutation, as described in Example 2 below.

In further experiments, other exemplary oligomers comprising a targeting sequence as set forth in Table 2 are prepared as PMOs. These antisense oligomers are introduced into the patient-derived fibroblasts and/or lymphocytes using a nucleofection protocol as also described in Example 2 below.

Example 2

Antisense Oligomers Induce Exon 2 Inclusion in GSD-II Patient-Derived Fibroblasts Experiments are performed to test the ability of antisense oligomers to induce exon 2 inclusion in fibroblasts and/or lymphocytes derived from individuals with GSD-II. In one set of experiments, 2'-O-methyl modified antisense oligomers are prepared according to standard protocols and transfected into GSD-II patient-derived fibroblasts and/or lymphocytes carrying the IVS1-13G>T mutation. In another set of experiments, PMOs are prepared according to standard protocols and introduced into these same cells by nucleofection. Levels of exon 2-containing mRNAs are then measured by RT-PCR.

GSD-II cells. Patient-derived fibroblasts or lymphocytes from individuals with GSD-II (Coriell cell lines GM00443, GM11661, GM14463 and/or GM14484) are cultured according to standard protocols in Eagle's MEM with 10% FBS. Cells are passaged about 3-5 days before the experiments and are approximately 80% confluent at transfection or nucleofection, GM00443 fibroblasts are from a 30 year old male. Adult form; onset in third decade; normal size and amount of mRNA for GAA, GAA protein detected by antibody, but only 9 to 26% of normal acid-alpha-1,4 glucosidase activity; passage 3 at CCR; donor subject is heterozygous with one allele carrying a T>G transversion at position −13 of the acceptor site of intron 1 of the GAA gene, resulting in alternatively spliced transcripts with deletion of the first coding exon [exon 2 (IVS1-13T>G)].

GM11661 fibroblasts are from a 38 year old male. Abnormal liver function tests; occasional charley-horse in legs during physical activity; morning headaches; intolerance to greasy foods; abdominal cyst; deficient fibroblast and WBC acid-alpha-1,4 glucosidase activity; donor subject is a compound heterozygote: allele one carries a T>G transversion at position −13 of the acceptor site of intron 1 of the GAA gene (IVS1-13T>G); the resulting alternatively spliced transcript has an in frame deletion of exon 2 which contains the initiation codon; allele two carries a deletion of exon 18.

GM14463 lymphocytes are from a 26 year old female. Clinically affected; adult onset; severe generalized muscle weakness and wasting; severe respiratory insufficiency; muscle biopsy showed acid maltase deficiency; donor subject is a compound heterozygote: one allele has a T>G transversion at position −13 of the acceptor site of intron 1 of the GAA gene (IVS1-13T>G) resulting in alternatively spliced transcripts with deletion of the first coding exon, exon 2; the second allele has a 1 bp deletion at nucleotide 366 in exon 2 (c.366delT) resulting in a frameshift and protein truncation[Gln124SerfsX18).

GM14484 lymphocytes are from a 61 year old male. Clinically affected; adult onset); donor subject is a compound heterozygote: one allele has a T>G transversion at position −13 of the acceptor site of intron 1 of the GAA gene (IVS1-13T>G) resulting in alternatively spliced transcripts with deletion of the first coding exon, exon 2; the second allele has a C>T transition at nucleotide 172 in exon 2 (c.172C>T) resulting in a stop at codon 58 [Gln58Ter (Q58X)].

Upon arrival, GSD-II patient cells are expanded and aliquots frozen for long-term storage. Cells are then propagated and RT-PCR is performed on total RNA extracted from the cells to confirm exon 2 is missing from the mature GAA-coding transcript.

Transfection Protocol. Briefly, 2'-O-methyl modified antisense oligomers are mixed with a cationic liposome preparation such as Lipofectamine 2000 and added to cultured cells over the concentration range 0, 2.5, 5, 10, 25, 50, 100 and 200 nM. Five hours after transfection, the media is replaced and the cells incubated in 5% $CO_2$ at 37° C. for 24 to 72 hours. A sham transfection and untreated cells are included as negative controls. Total RNA is extracted from the cell preparations and used as the template in RT-PCR assays for monitor the changes in GAA expression, in particular looking at the increased inclusion/retention of exon 2 in the mature GAA transcript. The transfected 2'-O-methyl modified antisense oligomers are shown in Table E1 below. For this example, each X for SEQ ID NOS: 24 and 25 was uracil (U).

TABLE E1

| No. on Gel | Name | Sequence | SEQ ID NO |
|---|---|---|---|
| 1 | GAA-IVS2(-4-20) | CCCGCCCCUGCCCUGCC | 10 |
| 2 | GAA-IVS2(-14-30) | UGGCCGCCGCCCCCGCCC | 11 |
| 3 | GAA-IVS2(-33-52) | UGUCCACGCGCACCCUCUGC | 12 |
| 4 | GAA-IVS2(-213-237) | UGACCCACCUUUUCAUAAAGAUGAA | 21 |
| 5 | GAA-IVS2(-234-258) | CUCUGGCAGCCCUACUCUACCUGAC | 22 |
| 6 | | GGCCCXGGXCXGCXGGCXCCCXGCX | 24 |
| 7 | | GCXCCCXGCAGCCCCXGCXXXGCAG | 25 |
| 8 | GAA-IVS1(-39-20) | GCUCAGCAGGGAGGCGGGAG | 4 |
| 9 | GAA-IVS1(-74-55) | GGCUCUCAAAGCAGCUCUGA | 5 |
| 10 | GAA-IVS1(-99-75) | GACAUCAACCGCGGCUGGCACUGCA | 6 |
| 11 | GAA-IVS1(-139-115) | GGGUAAGGUGGCCAGGGUGGGUGUU | 7 |
| 12 | GAA-IVS1(-158-140) | GCCCUGCUGUCUAGACUGG | 8 |
| 13 | GAA-IVS1(-179-160) | GAGAGGGCCAGAAGGAAGGG | 9 |
| 14 | GAA-IVS2(-53-72) | GUGAGGUGCGUGGGUGUCGA | 90 |
| 15 | GAA-IVS2(-73-92) | GCAACAUGCACCCCACCCUU | 14 |
| 16 | GAA-IVS2(-93-112) | AGGGCCCAGCACACAGUGGU | 15 |
| 17 | GAA-IVS2(-113-132) | UCACACCUCCGCUCCCAGCA | 16 |
| 18 | GAA-IVS2(-133-150) | GGCGCUGCCAUUGUCUGC | 17 |
| 19 | GAA-IVS2(-153-172) | GUGUCCCACUGCUCCCCGA | 18 |
| 20 | GAA-IVS2(-173-192) | CUGGAGUACCUGUCACCGUG | 19 |
| 21 | GAA-IVS2(-193-212) | UGAGCCCCGAGCCCUGCCUU | 20 |

TABLE E1-continued

| No. on Gel | Name | Sequence | SEQ ID NO |
|---|---|---|---|
| 22 | GAA-IVS2(-338-364) | CUAGUAUAAAUACAUCCCAAAUUUUGC | 23 |

For any of the sequences in Table E1, the uracil bases (U) can be substituted with thymine bases (T) and vice versa, and each X is independently selected from thymine (T) or uracil (U).

Nucleofection Protocol. Antisense PMOs are prepared as 1-2 mM stock solutions in nuclease-free water (not treated with DEPC) from which appropriate dilutions are made for nucleofection. GSD-II cells are trypsinized, counted, centrifuged at 90 g for 10 minutes, and $1\text{-}5\times10^5$ cells per well are resuspended in nucleofection Solution P2 (Lonza). Antisense PMO solution and cells are then added to each well of a Nucleocuvette 16-well strip, and pulsed with program EN-100. Cells are incubated at room temperature for 10 minutes and transferred to a 12-well plate in duplicate. Total RNA is isolated from treated cells after 48 hours using the GE Illustra 96 Spin kit following the manufacturer's recommended protocol. Recovered RNA is stored at −80° C. prior to analysis.

GAA RT-PCR. For PCR detection of exon 2-containing mRNAs, primer sequences are chosen from exon 1(forward) to exon 3(reverse). RT-PCR across exons 1-3 will generate a full length amplicon of around 1177 bases (see FIG. 2 for the full-length amplicon from normal human cells). The size difference between the intact amplicon (1177 bases) and the ~600 base transcript that is missing exon 2 (exon 2 is ~578 bases) means there will be substantial preferential amplification of the shorter product. This will set a high benchmark in assaying the efficacy of antisense oligomers to induce splicing of the full-length transcript or exon2-containing transcript.

Reverse transcriptase PCR is performed to amplify the GM allele using the SuperScript III One-Step RT-PCR system (Invitrogen). 400 ng total RNA isolated from nucleofected cells is reverse transcribed and amplified with the gene-specific primers.

The amplification solution provided in the One-Step kit is supplemented with Cy5-labeled dCTP (GE) to enable band visualization by fluorescence. Digested samples are run on a pre-cast 10% acrylamide/TBE gel (Invitrogen) and visualized on a Typhoon Trio (GE) using the 633 nm excitation laser and 670 nm BP 30 emission filter with the focal plane at the platen surface. Gels are analyzed with ImageQuant (GE) to determine the intensities of the bands. Intensities from all bands containing exon 2 are added together to represent the full exon 2 transcript levels in the inclusion analysis.

Alternatively, PCR amplification products are analyzed on a Caliper bioanalyzer or Agilent 2200 Tape Station for determination of % exon inclusion.

Figure 3A:
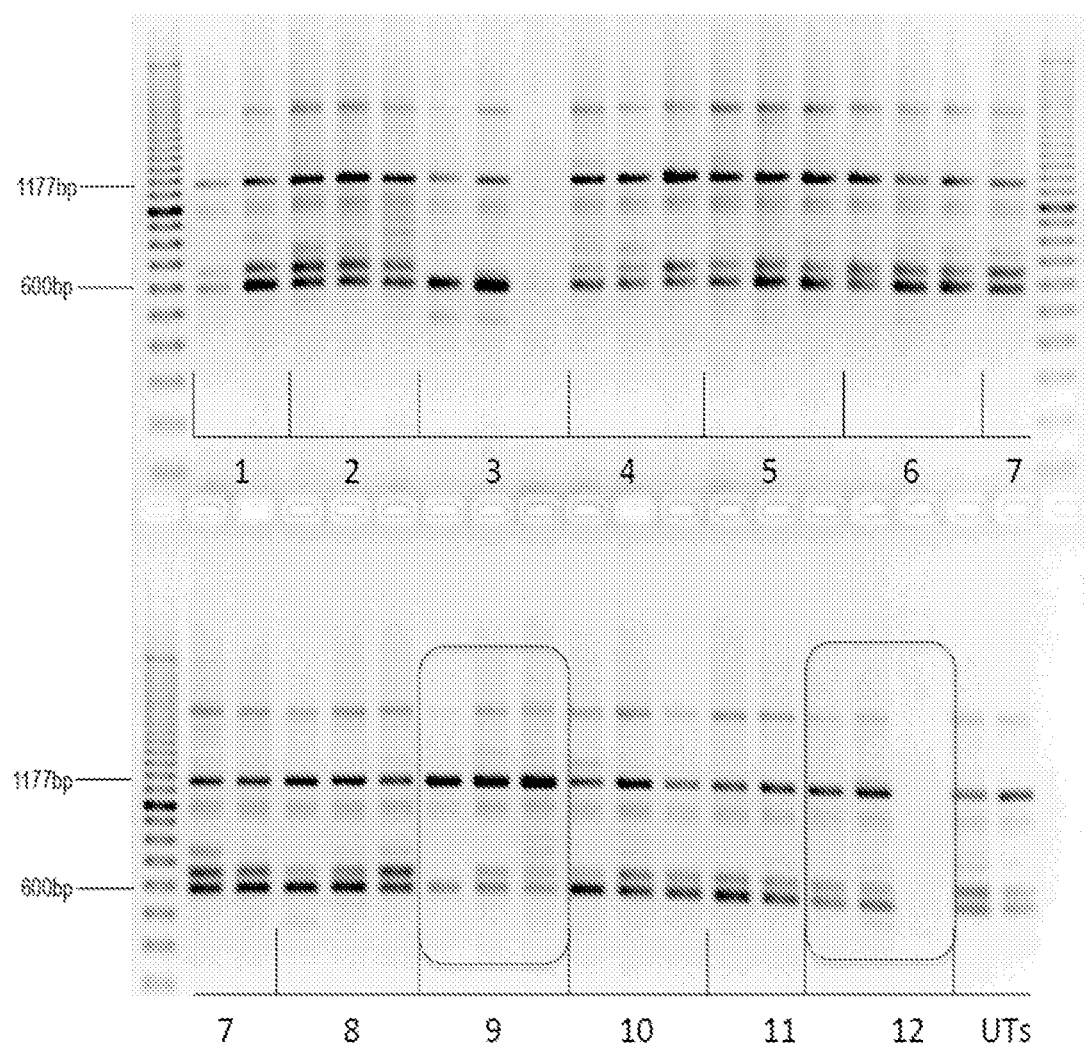
FIGS. 3A-3C show the results for the 2'-O-methyl modified antisense oligomers from Table E1 of Example 2.
Figure 3B:
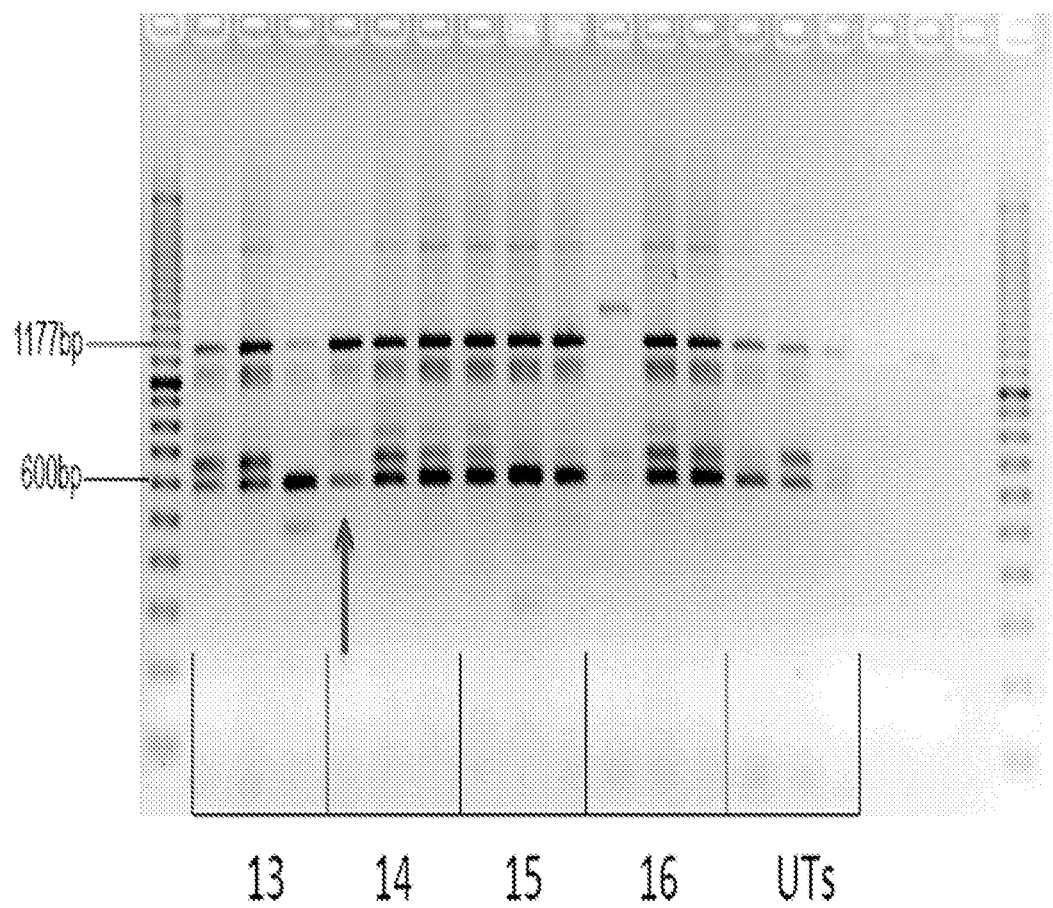
Figure 3C:
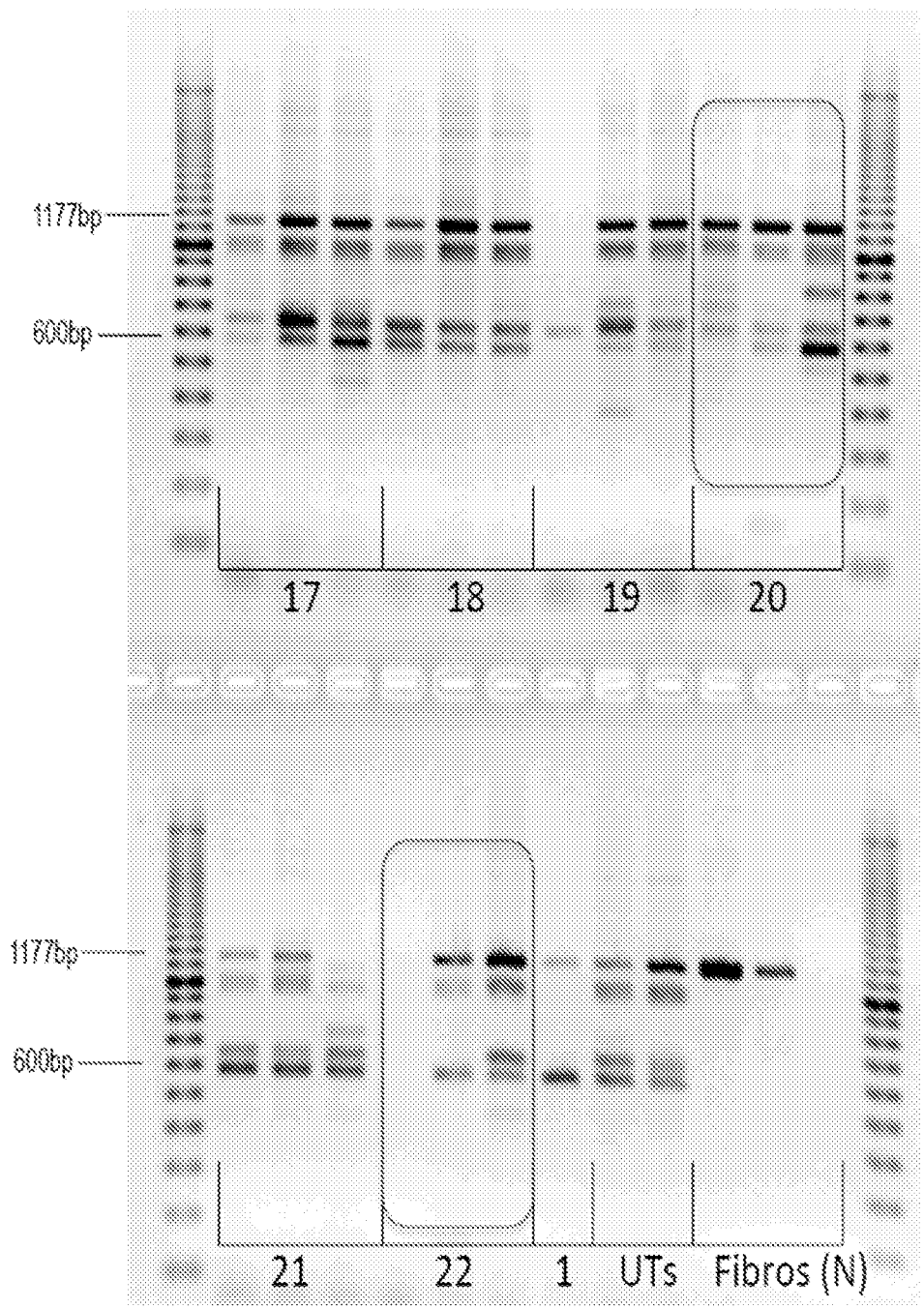

The results for the 2'-O-methyl modified antisense oligomers of Table E1 are shown in FIGS. 3A-3C. FIG. 3A shows that oligomers 9 (GAA-IVS1 (−74-55)) and 12 GAA-IVS1 (−158-140)) induced exon 2-inclusion in human cells carrying the IVS1-13G>T mutation, as evidenced by reduced amplification of the ~600 base amplicon (relative to the full-length ~1177 base amplicon). FIG. 3B shows that oligomer 14 (GAA-IVS2 (−53-72)) induced exon-2 inclusion, and FIG. 3C shows that oligomers 20 (GAA-IVS2 (−173-192)) and 22 (GAA-IVS2 (−338-364)) likewise induced a degree of exon-2 inclusion Example 3

Antisense Oligomers Induce Elevated Levels of Enzymatically Active Acid Alpha-Glucosidase in GSD-II Patient-Derived Fibroblasts GSD-II patient cells treated with the antisense oligomers of the disclosure (as described above) are shown to have elevated levels of functional/active GAA due to increased expression of exon 2-containing GAA mRNA. Treated cells are prepared and protein is extracted using standard protocols. Protein concentration is determined and defined quantities of extracted protein are measured for GAA enzyme activity. Antisense oligomers that induce higher levels of GAA are preferred embodiments of the disclosure.

Example 4

Figure 4A:
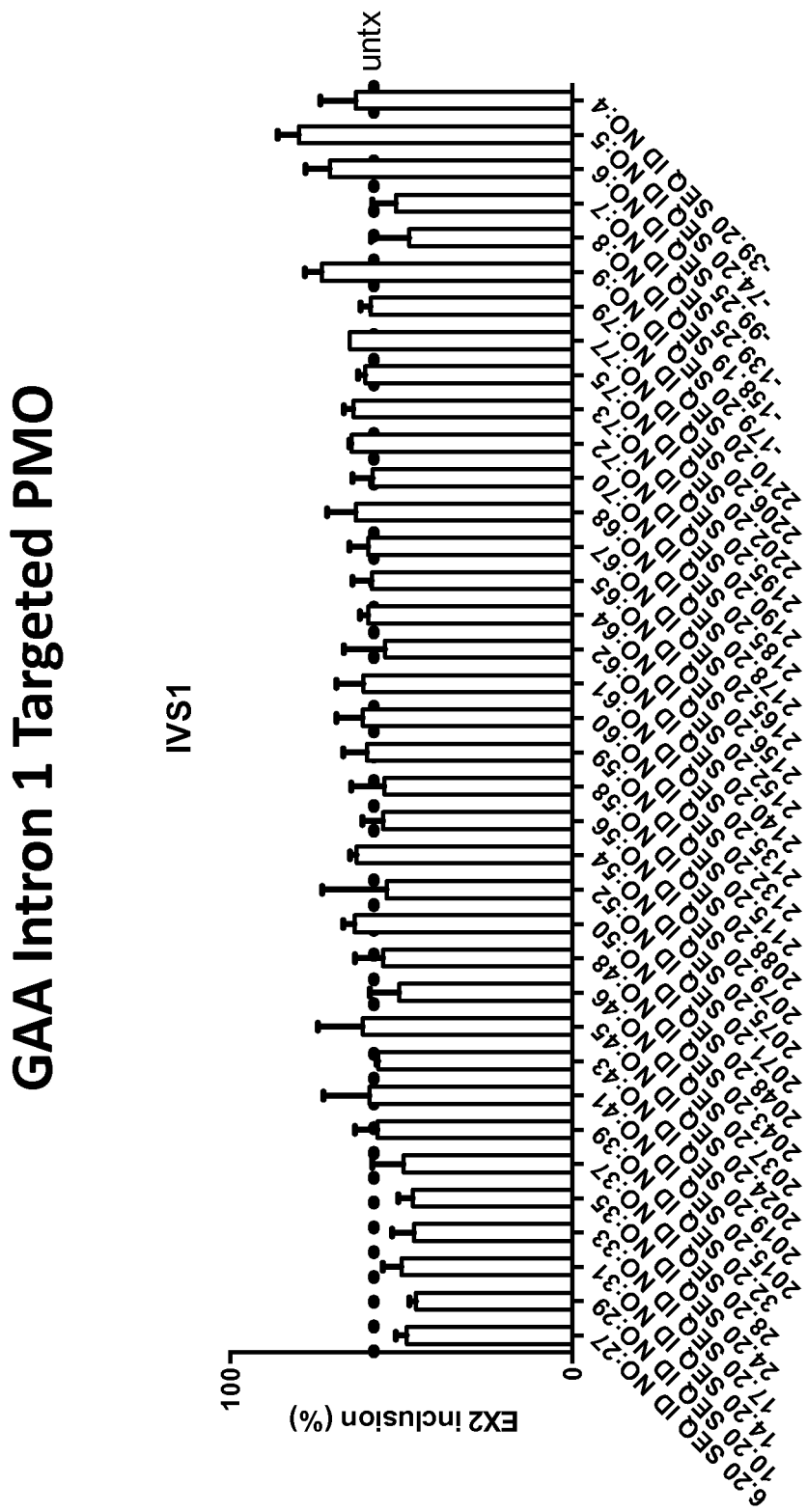
FIGS. 4A-4C show the RT-PCR results for the PMO antisense oligomers of Table 4A.

Antisense PMO-Induced Dose-Dependent Exon 2 Inclusion in GSD-II Patient-Derived Fibroblasts GM00443 fibroblasts were treated using the above-described nucleofection procedure and antisense sequences made as PMOs based on the initial GAA exon 2 inclusion results described above in Example 2. 20 uM PMOs, according to formula (VII) above with targeting sequences identified in Table 4A below, were nucleofected as previously described, and cells incubated at 37° C. with 5% $CO_2$ for 24 hours before total RNA isolation. RT-PCR amplification of RNA with primers FWD124 (SEQ ID NO: 121), FWD645 (SEQ ID NO: 122) and REV780 (SEQ ID NO: 123) of Table 4B was analyzed using a Caliper LabChip to determine percent exon 2 inclusion, the results of which are shown in FIGS. 4A (intron 1 targeted PMOs), 4B (exon 2 targeted PMOs), and 4C (intron 2 targeted PMOs).

TABLE 4A

Nucleofected PMO targeting sequences

| Name | Sequence (5'-3') | SEQ ID NO |
|---|---|---|
| GAA Intron 1 Antisense Sequences: FIG. 4A | | |
| GAA-IVS1(-39-20) | GCUCAGCAGGGAGGCGGGAG | 124 |
| GAA-IVS1(-74-55) | GGCUCUCAAAGCAGCUCUGA | 125 |
| GAA-IVS1(-99-75) | GACAUCAACCGCGGCUGGCACUGCA | 126 |
| GAA-IVS1(-139-115) | GGGUAAGGUGGCCAGGGUGGGUGUU | 127 |
| GAA-IVS1(-158-140) | GCCCUGCUGUCUAGACUGG | 128 |
| GAA-IVS1(-179-160) | GAGAGGGCCAGAAGGAAGGG | 9 |
| GAA-IVS1.6.20 | GCGGGGCAGACGTCAGGTGT | 129 |
| GAA-IVS1.10.20 | CAGCGCGGGGCAGACGTCAG | 130 |
| GAA-IVS1.14.20 | CCGGCAGCGCGGGGCAGACG | 31 |
| GAA-IVS1.17.20 | CCGCCGGCAGCGCGGGGCAG | 33 |
| GAA-IVS1.24.20 | GATGTTACCGCCGGCAGCGC | 131 |
| GAA-IVS1.28.20 | CTGGGATGTTACCGCCGGCA | 132 |
| GAA-IVS1.32.20 | GCTTCTGGGATGTTACCGCC | 133 |
| GAA-IVS1.2015.20 | TGGCAACTCGTATGTCCTTA | 134 |

TABLE 4A-continued

Nucleofected PMO targeting sequences

| Name | Sequence (5'-3') | SEQ ID NO |
|---|---|---|
| GAA-IVS1.2019.20 | ATTCTGGCAACTCGTATGTC | 135 |
| GAA-IVS1.2024.20 | AAGTGATTCTGGCAACTCGT | 136 |
| GAA-IVS1.2037.20 | TGGGTGTCAGCGGAAGTGAT | 137 |
| GAA-IVS1.2043.20 | GTCCACTGGGTGTCAGCGGA | 138 |
| GAA-IVS1.2048.20 | GCTTGGTCCACTGGGTGTCA | 139 |
| GAA-IVS1.2071.20 | CCCCACTTCTGCATAAAGGT | 140 |
| GAA-IVS1.2075.20 | GGAGCCCCACTTCTGCATAA | 141 |
| GAA-IVS1.2079.20 | GCTGGGAGCCCCACTTCTGC | 142 |
| GAA-IVS1.2088.20 | CCACGCCTGGCTGGGAGCCC | 143 |
| GAA-IVS1.2115.20 | TCCGAAGTGCTGGGATTTCA | 144 |
| GAA-IVS1.2132.20 | TCCACCCCCCTTGGCCTTCC | 145 |
| GAA-IVS1.2135.20 | TGATCCACCCCCTTGGCCT | 146 |
| GAA-IVS1.2140.20 | TCAAGTGATCCACCCCCCTT | 147 |
| GAA-IVS1.2152.20 | GAACTCCTGAGCTCAAGTGA | 148 |
| GAA-IVS1.2156.20 | TCTCGAACTCCTGAGCTCAA | 149 |
| GAA-IVS1.2165.20 | CCAGGCTGGTCTCGAACTCC | 150 |
| GAA-IVS1.2178.20 | TTTGCCATGTTACCCAGGCT | 151 |
| GAA-IVS1.2185.20 | ACGGGATTTTGCCATGTTAC | 152 |
| GAA-IVS1.2190.20 | TAGAGACGGGATTTTGCCAT | 153 |
| GAA-IVS1.2195.20 | TTTTGTAGAGACGGGATTTT | 154 |
| GAA-IVS1.2202.20 | TCTGTATTTTGTAGAGACG | 155 |
| GAA-IVS1.2206.20 | ATTTTCTGTATTTTTGTAGA | 156 |
| GAA-IVS1.2210.20 | GCTAATTTTCTGTATTTTTG | 157 |

Figure 4B:
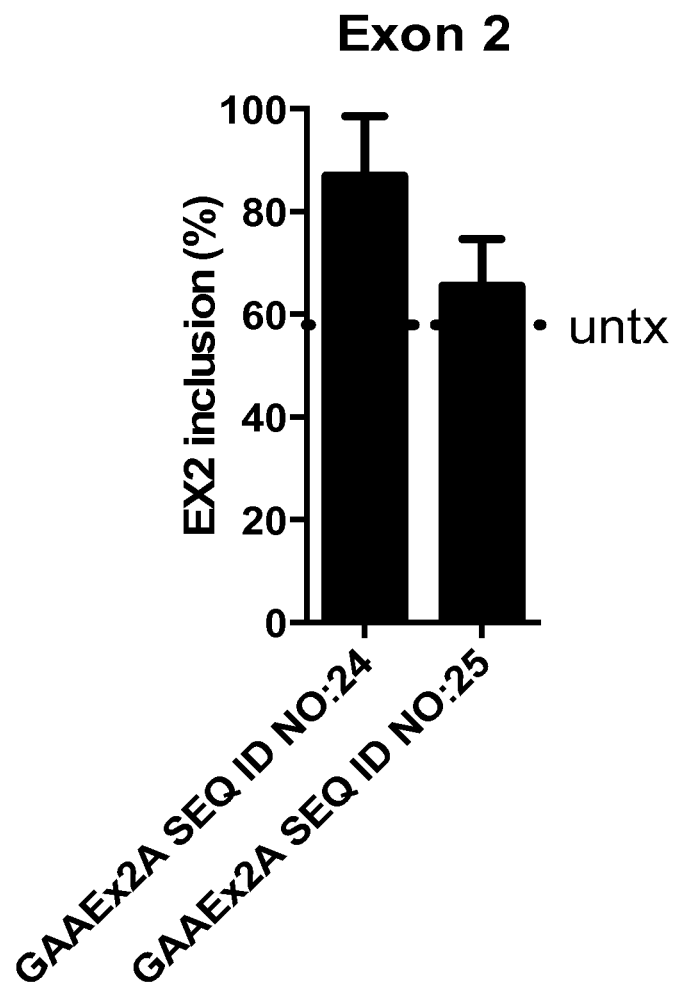

GAA Exon 2 Antisense Sequences: FIG. 4B

| Name | Sequence (5'-3') | SEQ ID NO |
|---|---|---|
| GAAEx2A(+202+226) | GGCCCUGGUCUGCUGGCUCCCUGCU | 158 |
| GAAEx2A(+367+391) | GCUCCCUGCAGCCCCUGCUUUGCAG | 159 |

Figure 4C:
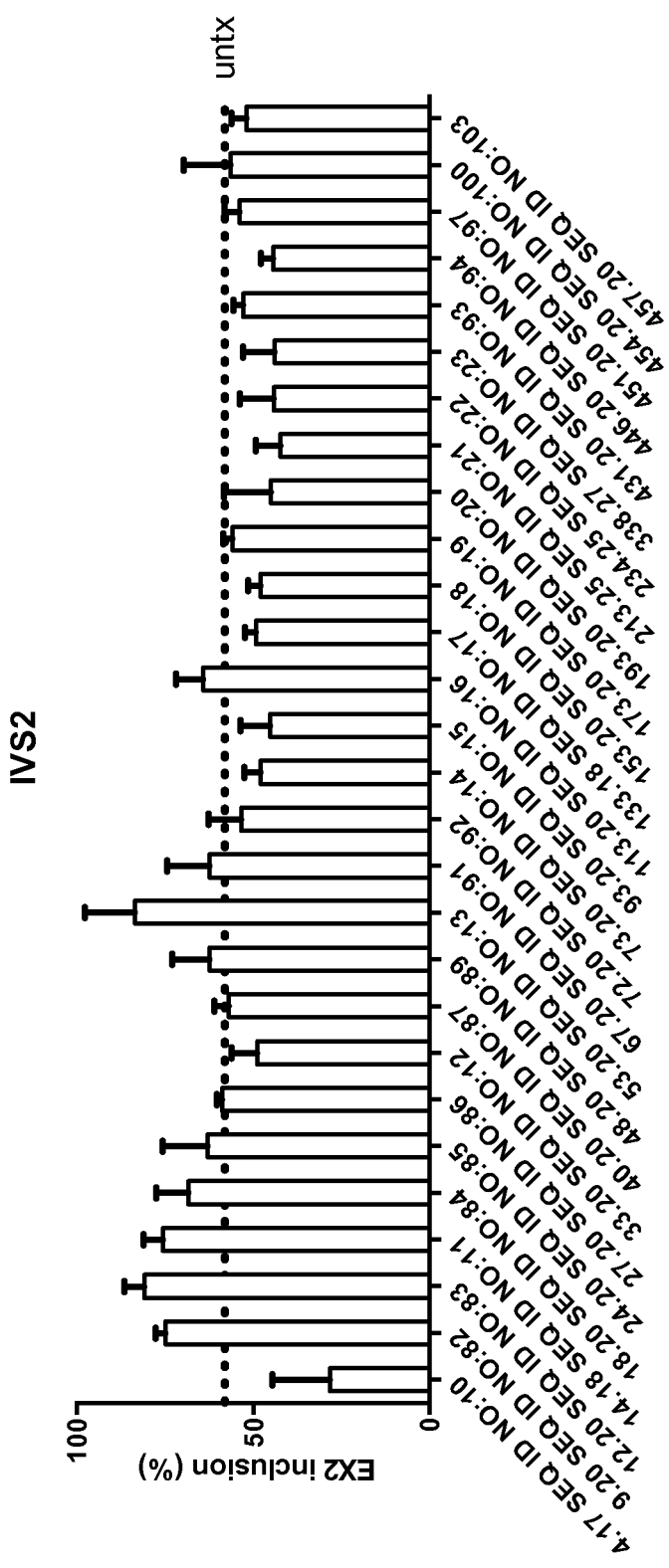

GAA Intron 2 Antisense Sequences: FIG. 4C

| Name | Sequence (5'-3') | SEQ ID NO |
|---|---|---|
| GAA-IVS2(-4-20) | CCCGCCCCUGCCCUGCC | 160 |
| GAA-IVS2(-14-30) | UGGCCGCCGCCCCGCCC | 161 |
| GAA-IVS2(-33-52) | UGUCCACGCGCACCCUCUGC | 162 |
| GAA-IVS2(-53-72) | GUGAGGUGCGUGGGUGUCGA | 163 |
| GAA-IVS2(-73-92) | GCAACAUGCACCCCACCCUU | 164 |
| GAA-IVS2(-93-112) | AGGGCCCAGCACACAGUGGU | 165 |
| GAA-IVS2(-113-132) | UCACACCUCCGCUCCCAGCA | 166 |
| GAA-IVS2(-133-150) | GGCGCUGCCAUUGUCUGC | 167 |
| GAA-IVS2(-153-172) | GUGUCCCCACUGCUCCCCGA | 168 |
| GAA-IVS2(-173-192) | CUGGAGUACCUGUCACCGUG | 169 |
| GAA-IVS2(-193-212) | UGAGCCCCGAGCCCUGCCUU | 170 |
| GAA-IVS2(-213-237) | UGACCCACCUUUUCAUAAAGAUGAA | 171 |
| GAA-IVS2(-234-258) | CUCUGGCAGCCCUACUCUACCUGAC | 172 |
| GAA-IVS2(-338-364) | CUAGUAUAAAUACAUCCCAAAUUUUGC | 173 |
| GAA-IVS2.6.20 | CCGCCCCGCCCCUGCCCUG | 174 |
| GAA-IVS2.9.20 | CCGCCGCCCCGCCCCUGCC | 175 |
| GAA-IVS2.12.20 | TGGCCGCCGCCCCGCCCCT | 176 |
| GAA-IVS2.18.20 | CTGCCCTGGCCGCCGCCCCC | 177 |
| GAA-IVS2.24.20 | CACCCTCTGCCCTGGCCGCC | 178 |
| GAA-IVS2.27.20 | GCGCACCCTCTGCCCTGGCC | 179 |
| GAA-IVS2.40.20 | TGTCGATGTCCACGCGCACC | 180 |
| GAA-IVS2.48.20 | TGCGTGGGTGTCGATGTCCA | 181 |
| GAA-IVS2.67.20 | GCACCCCACCCTTGTGAGGT | 182 |
| GAA-IVS2.72.20 | AACATGCACCCCACCCTTGT | 183 |
| GAA-IVS2.431.20 | AGGAGGAGGACGCCTCCCCC | 184 |
| GAA-IVS2.446.20 | CTCATCTGCAGAGCCAGGAG | 185 |
| GAA-IVS2.451.20 | GCTCCCTCATCTGCAGAGCC | 186 |
| GAA-IVS2.454.20 | TCGGCTCCCTCATCTGCAGA | 187 |
| GAA-IVS2.457.20 | GCCTCGGCTCCCTCATCTGC | 188 |

TABLE 4B

RT-PCR primer sequences for RNA amplification

| Name | Sequence (5'-3') | SEQ ID NO |
|---|---|---|
| FWD124 | CGTTGTTCAGCGAGGGA | 121 |
| FWD645 | CTCCTCTGAAATGGGCTACAC | 122 |
| REV780 | ACCTCGTAGCGCCTGTTA | 123 |

Thus, the disclosure also includes a method of detecting exon 2 inclusion in a human acid alpha-glucosidase (GAA) gene mRNA, the method comprising:

amplifying the GAA mRNA with at least one polymerase chain reaction primer comprising a base sequence selected from the group consisting of SEQ ID NOS: 121, 122, or 123.

The invention claimed is:

1. An antisense oligomer compound of at least 20 nucleotides or nucleotide analogs, wherein the oligomer comprises:

a phosphoramidate morpholino oligomer or phosphorodiamidate morpholino oligomer (PMO), a peptide nucleic acid (PNA), a locked nucleic acid (LNA), a phosphorothioate oligomer, a tricyclo-DNA oligomer, a tricyclo-phosphorothioate oligomer, a 2'O-Me-phosphorothioate oligomer, or any combination of the foregoing; and a targeting sequence, wherein the targeting sequence is complementary to a target region within intron 1 (SEQ ID. NO: 1) of a pre-mRNA of the human acid alpha-glucosidase (GAA) gene, and wherein the targeting sequence is selected from SEQ ID NOS: 4-6, 9, 45, 50, 54, 59-61, 68, 72, 73, and 77, wherein X is selected from uracil (U) or thymine (T).

2. A compound of formula (I):

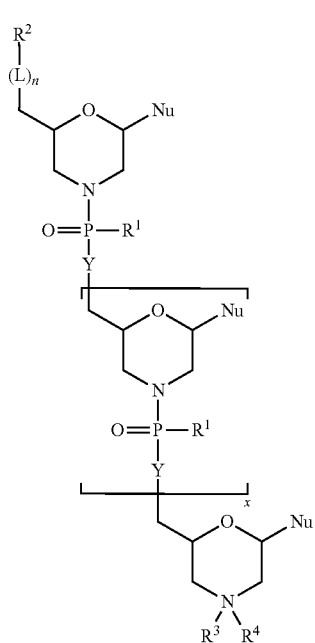

(I)

or a pharmaceutically acceptable salt thereof, wherein:

each Nu is a nucleobase which taken together forms a targeting sequence;

x is an integer from 18 to 38;

each Y is independently selected from O or $-NR^a$, wherein $R^a$ is selected from the group consisting of hydrogen, $-T^1-NR^cR^dR^e$, and a cell penetrating peptide, wherein:

$R^c$ is selected from the group consisting of hydrogen, $C_1$-$C_6$ alkyl, aralkyl, and $-C(=NH)NH_2$, $R^d$ is selected from the group consisting of hydrogen, aralkyl, and $C_1$-$C_6$ alkyl, or $R^c$ and $R^d$ taken together with the nitrogen atom to which they are attached form a 5-7 membered ring when $R^c$ and $R^d$ are each independently $C_1$-$C_6$ alkyl or aralkyl, where the ring is optionally substituted with a substituent selected from the group consisting of $C_1$-$C_6$ alkyl, phenyl, halogen, and aralkyl, and $R^e$ is selected from the group consisting of an electron pair, hydrogen, $C_1$-$C_6$ alkyl, and aralkyl;

each L is independently selected from the group consisting of:

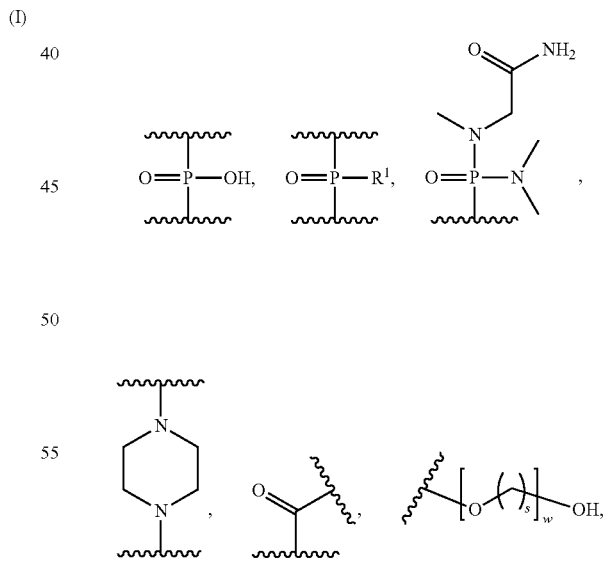

and a cell penetrating peptide, wherein w is an integer selected from 3-20, and S is an integer selected from 1 to 8;

n is an integer from 0 to 3;

each $R^1$ is independently selected from the group consisting of $-N(CH_3)_2$, $-NR^5R^6$, $-OR^7$, a moiety of formula (II):

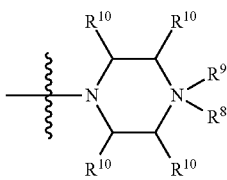

(II)

wherein:
R[8] is selected from the group consisting of hydrogen, methyl, —C(=NH)NH$_2$, —Z-T[2]-NHC(=NH)NH$_2$, and a cell penetrating peptide, where Z is carbonyl or a direct bond,
R[9] is selected from the group consisting of an electron pair, hydrogen, C$_1$-C$_6$ alkyl, and aralkyl;
each R[10] is independently selected from hydrogen or methyl; and R[13] is selected from the group consisting of an electron pair, hydrogen, C$_1$-C$_6$ alkyl, and aralkyl;
R[2] is selected from the group consisting of hydrogen, OH, a nucleotide, a cell-penetrating peptide, a moiety of formula:

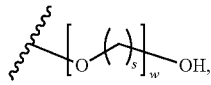

trityl, —C(=O)OR[f], and acyl, wherein R[f] is C$_1$-C$_{30}$ alkyl optionally substituted by one or more oxygen or hydroxyl moieties, or R[2] is absent;
R[3] is selected from the group consisting of hydrogen, a C$_1$-C$_6$ alkyl, a nucleotide, a cell penetrating peptide, —C(=NH)NH$_2$, trityl, —C(=O)OR[g], acyl, and a moiety of formula:

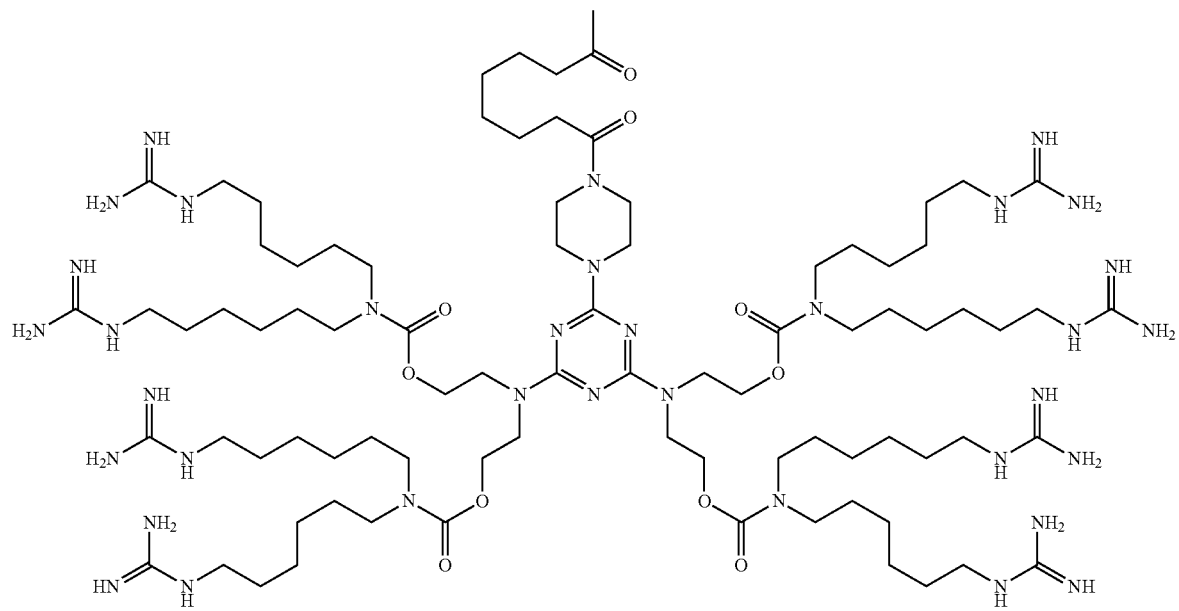 [SMILES: CC(=O)CCCCCCC(=O)N1CCN(c2nc(N(CCOC(=O)N(CCCCCCNC(=N)N)CCCCCCNC(=N)N)CCOC(=O)N(CCCCCCNC(=N)N)CCCCCCNC(=N)N)nc(N(CCOC(=O)N(CCCCCCNC(=N)N)CCCCCCNC(=N)N)CCOC(=O)N(CCCCCCNC(=N)N)CCCCCCNC(=N)N)n2)CC1]

a moiety of formula (III):

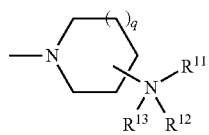

(III)

wherein:
q is an integer from 0 to 2,
R[11] is selected from the group consisting of hydrogen, C$_1$-C$_6$ alkyl, aralkyl, and —C(=NH)NH$_2$,
R[12] is selected from the group consisting of hydrogen, aralkyl, and C$_1$-C$_6$ alkyl, or
R[11] and R[12] taken together with the nitrogen atom to which they are attached form a 5-7 membered ring where the ring is optionally substituted with a substituent selected from the group consisting of C$_1$-C$_6$ alkyl, phenyl, halogen, and aralkyl, and wherein
R[g] is C$_1$-C$_{30}$ alkyl optionally substituted by one or more oxygen or hydroxyl moieties;
R[4] is selected from the group consisting of an electron pair, hydrogen, a C$_1$-C$_6$ alkyl, and acyl
R[5] is independently selected from hydrogen or methyl;
R[6] and R[7] is independently selected from hydrogen or -T[3]-NR[c]R[d]R[e]; and
each of T[1], T[2], and T[3] is independently an optional linker of up to 18 atoms in length comprising alkyl, alkoxy, or alkylamino groups, or combinations thereof, wherein the targeting sequence is complementary to a target region within intron 1 (SEQ ID. NO: 1) of a pre-mRNA of the human acid alpha-glucosidase (GAA) gene, and wherein the targeting sequence is selected from SEQ ID NOS: 4-6, 9, 45, 50, 54, 59-61, 68, 72, 73, and 77, wherein X is selected from uracil (U) or thymine (T).

3. The compound of claim 2, wherein each R[1] is —N(CH$_3$)$_2$.

4. The compound of claim 2, wherein at least one $R^1$ is selected from the group consisting of

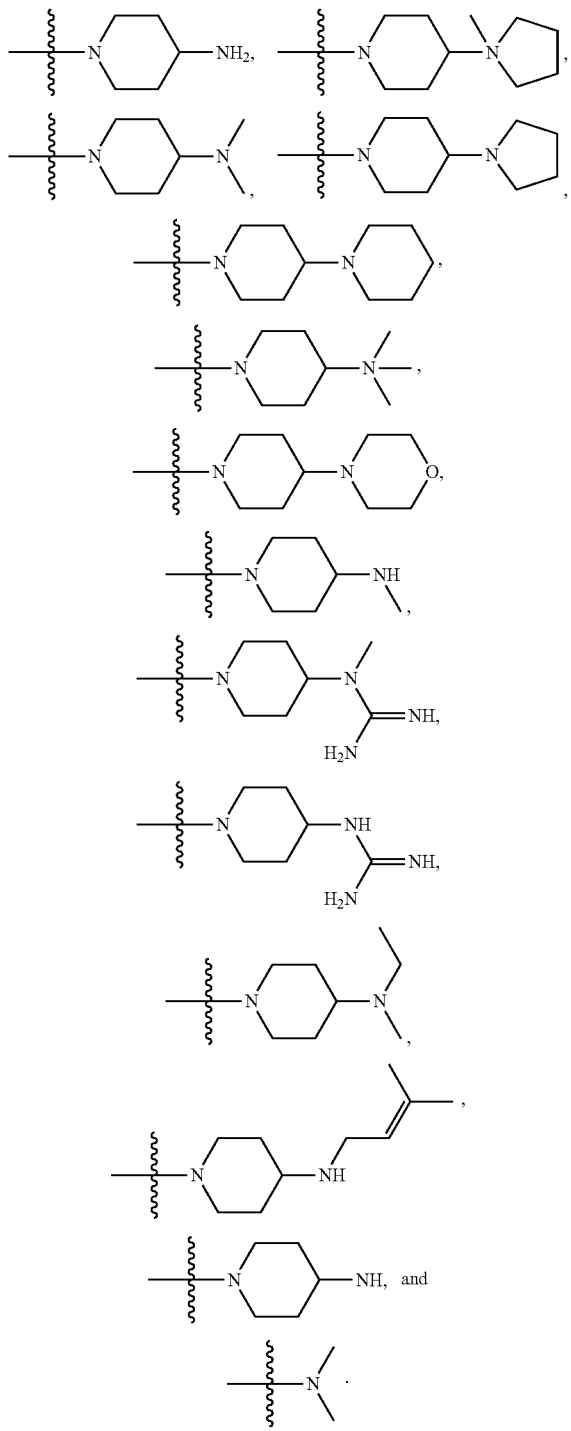

5. The compound of claim 2, wherein 50-90% of the $R^1$ groups are —$N(CH_3)_2$.

6. The compound of claim 2, wherein 66% of the $R^1$ groups are —$N(CH_3)_2$.

7. The compound of claim 2, wherein:
n is 2;

$R^2$ and L taken together are of the formula:

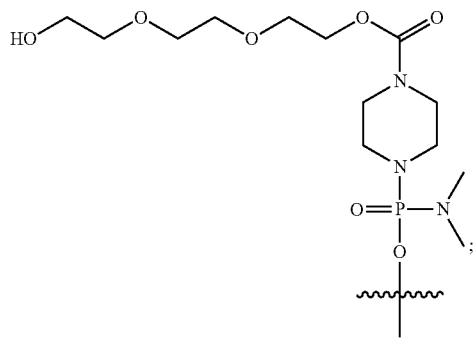

and
Y is O at each occurrence.

8. A compound of formula (IV):

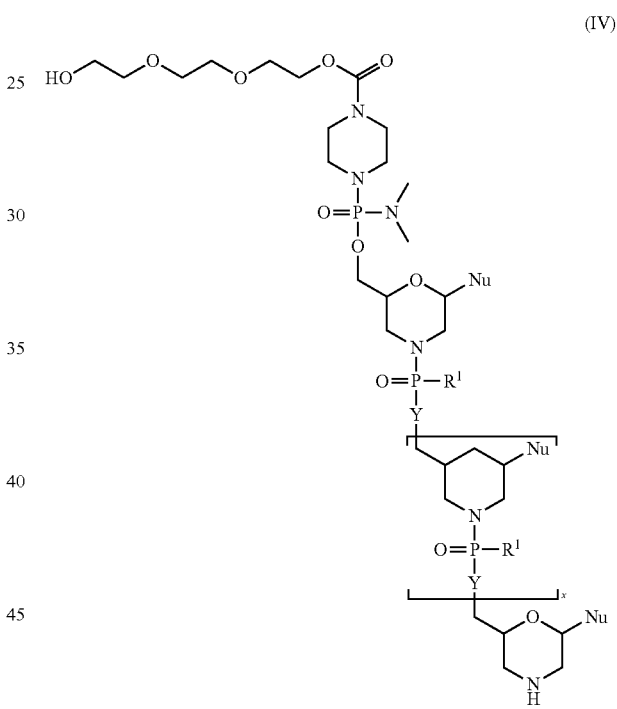

or a pharmaceutically acceptable salt thereof, wherein:
each Nu is a nucleobase which taken together form a targeting sequence;
x is an integer from 18 to 25;
each Y is O;
each $R^1$ is independently selected from the group consisting of:

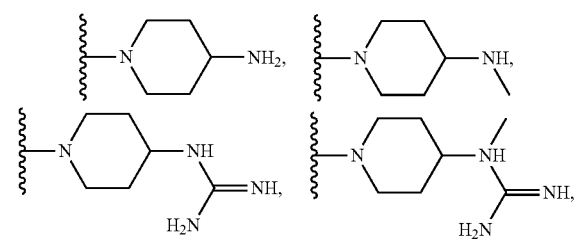

-continued
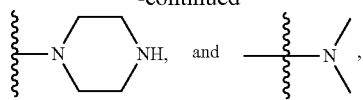
wherein at least one $R^1$ is —$N(CH_3)_2$, and
wherein the targeting sequence is selected from SEQ ID NOS: 4-6, 9, 45, 50, 54, 59-61, 68, 72, 73, and 77,
wherein X is selected from uracil (U) or thymine (T).
* * * * *

SEQUENCE LISTING

<160> NUMBER OF SEQ ID NOS: 188

<210> SEQ ID NO 1
<211> LENGTH: 2664
<212> TYPE: DNA
<213> ORGANISM: Homo sapiens
<220> FEATURE:
<221> NAME/KEY: misc_feature
<222> LOCATION: (2652)..(2652)
<223> OTHER INFORMATION: n is t or G

<400> SEQUENCE: 1

| | | | | | |
|---|---|---|---|---|---|
| gtgagacacc | tgacgtctgc | cccgcgctgc | cggcggtaac | atcccagaag | cgggtttgaa | 60 |
| cgtgcctagc | cgtgccccca | gcctcttccc | ctgagcggag | cttgagcccc | agacctctag | 120 |
| tcctcccggt | ctttatctga | gttcagctta | gagatgaacg | gggagccgcc | ctcctgtgct | 180 |
| gggcttgggg | ctggaggctg | catcttcccg | tttctagggt | ttcctttccc | cttttgatcg | 240 |
| acgcagtgct | cagtcctggc | cgggacccga | gccacctctc | ctgctcctgc | aggacgcaca | 300 |
| tggctgggtc | tgaatccctg | gggtgaggag | caccgtggcc | tgagagggg | ccctgggcc | 360 |
| agctctgaaa | tctgaatgtc | tcaatcacaa | agaccccctt | aggccaggcc | aggggtgact | 420 |
| gtctctggtc | tttgtccctg | gttgctggca | catagcaccc | gaaacccttg | gaaaccgagt | 480 |
| gatgagagag | ccttttgctc | atgaggtgac | tgatgaccgg | ggacaccagg | tggcttcagg | 540 |
| atggaagcag | atggccagaa | agaccaaggc | ctgatgacgg | gttgggatgg | aaaaggggtg | 600 |
| aggggctgga | gattgagtga | atcaccagtg | gcttagtcaa | ccatgcctgc | acaatggaac | 660 |
| cccgtaagaa | accacaggga | tcagagggct | tcccgccggg | ttgtggaaca | caccaaggca | 720 |
| ctggagggtg | gtgcgagcag | agagcacagc | atcactgccc | ccacctcaca | ccaggcccta | 780 |
| cgcatctctt | ccatacggct | gtctgagttt | tatcctttgt | aataaaccag | caactgtaag | 840 |
| aaacgcactt | tcctgagttc | tgtgaccctg | aagagggagt | cctgggaacc | tctgaattta | 900 |
| taactagttg | atcgaaagta | caagtgacaa | cctgggattt | gccattggcc | tctgaagtga | 960 |
| aggcagtgtt | gtgggactga | gcccttaacc | tgtggagtct | gtgctgactc | caggtagtgt | 1020 |
| caagattgaa | ttgaattgta | ggacacccag | ccgtgtccag | aaagttgcag | aattgatggg | 1080 |
| tgtgagaaaa | accctacaca | tttaatgtca | gaagtgtggg | taaaatgttt | caccctccag | 1140 |
| cccagagagc | cctaatttac | cagtggccca | cggtggaaca | ccacgtccgg | ccgggggcag | 1200 |
| agcgttccca | gccaagcctt | ctgtaacatg | acatgacagg | tcagactccc | tcgggccctg | 1260 |
| agttcacttc | ttcctggtat | gtgaccagct | cccagtacca | gagaaggttg | cacagtcctc | 1320 |
| tgctccaagg | agcttcactg | gccagggct | gctttctgaa | atccttgcct | gcctctgctc | 1380 |
| caaggcccgt | tcctcagaga | cgcagacccc | tctgatggct | gactttggtt | tgaggacctc | 1440 |
| tctgcatccc | tcccccatgg | ccttgctcct | aggacacctt | cttcctcctt | tccctggggt | 1500 |
| cagacttgcc | taggtgcggt | ggctctccca | gccttcccca | cgccctcccc | atggtgtatt | 1560 |
| acacacacca | aagggactcc | cctattgaaa | tccatgcata | ttgaatcgca | tgtgggttcc | 1620 |
| ggctgctcct | gggaggagcc | aggctaatag | aatgtttgcc | ataaaatatt | aatgtacaga | 1680 |
| gaagcgaaac | aaaggtcgtt | ggtacttgtt | aaccttacca | gcagaataat | gaaagcgaac | 1740 |
| ccccatatct | catctgcacg | cgacatcctt | gttgtgtctg | tacccgaggc | tccaggtgca | 1800 |
| gccactgtta | cagagactgt | gtttcttccc | catgtacctc | ggggccggg | aggggttctg | 1860 |
| atctgcaaag | tcgccagagg | ttaagtcctt | tctctcttgt | ggctttgcca | ccctggagt | 1920 |
| gtcaccctca | gctgcggtgc | ccaggattcc | ccactgtggt | atgtccgtgc | accagtcaat | 1980 |

| | |
|---|---|
| aggaaaggga gcaaggaaag gtactgggtc cccctaagga catacgagtt gccagaatca | 2040 |
| cttccgctga cacccagtgg accaagccgc acctttatgc agaagtgggg ctcccagcca | 2100 |
| ggcgtggtca ctcctgaaat cccagcactt cggaaggcca agggggtgg atcacttgag | 2160 |
| ctcaggagtt cgagaccagc ctgggtaaca tggcaaaatc ccgtctctac aaaaatacag | 2220 |
| aaaattagct gggtgcggtg gtgtgtgcct acagtcccag ctactcagga ggctgaagtg | 2280 |
| ggaggattgc ttgagtctgg gaggtggagg ttgcagtgag ccaggatctc accacagcac | 2340 |
| tctggcccag cgacagctg tttggcctgt ttcaagtgtc tacctgcctt gctggtcttc | 2400 |
| ctggggacat tctaagcgtg tttgatttgt aacattttag cagactgtgc aagtgctctg | 2460 |
| cactcccctg ctggagcttt tctcgccctt ccttctggcc ctctcccag tctagacagc | 2520 |
| agggcaacac ccaccctggc caccttaccc cacctgcctg ggtgctgcag tgccagccgc | 2580 |
| ggttgatgtc tcagagctgc tttgagagcc ccgtgagtgc cgcccctccc gcctccctgc | 2640 |
| tgagcccgct tncttctccc gcag | 2664 |

<210> SEQ ID NO 2
<211> LENGTH: 578
<212> TYPE: DNA
<213> ORGANISM: Homo sapiens

<400> SEQUENCE: 2

| | |
|---|---|
| gcctgtagga gctgtccagg ccatctccaa ccatgggagt gaggcacccg ccctgctccc | 60 |
| accggctcct ggccgtctgc gccctcgtgt ccttggcaac cgctgcactc ctggggcaca | 120 |
| tcctactcca tgatttcctg ctggttcccc gagagctgag tggctcctcc ccagtcctgg | 180 |
| aggagactca cccagctcac cagcagggag ccagcagacc agggcccgg gatgcccagg | 240 |
| cacaccccgg ccgtcccaga gcagtgccca cacagtgcga cgtcccccc aacagccgct | 300 |
| tcgattgcgc ccctgacaag gccatcaccc aggaacagtg cgaggcccgc ggctgttgct | 360 |
| acatccctgc aaagcagggg ctgcagggag cccagatggg gcagccctgg tgcttcttcc | 420 |
| cacccagcta ccccagctac aagctggaga acctgagctc ctctgaaatg ggctacacgg | 480 |
| ccaccctgac ccgtaccacc cccaccttct tccccaagga catcctgacc ctgcggctgg | 540 |
| acgtgatgat ggagactgag aaccgcctcc acttcacg | 578 |

<210> SEQ ID NO 3
<211> LENGTH: 616
<212> TYPE: DNA
<213> ORGANISM: Homo sapiens

<400> SEQUENCE: 3

| | |
|---|---|
| gtgggcaggg caggggcggg ggcggcggcc agggcagagg gtgcgcgtgg acatcgacac | 60 |
| ccacgcacct cacaagggtg gggtgcatgt tgcaccactg tgtgctgggc ccttgctggg | 120 |
| agcggaggtg tgagcagaca atggcagcgc ccctcgggga gcagtgggga caccacggtg | 180 |
| acaggtactc cagaaggcag ggctcggggc tcattcatct ttatgaaaag gtgggtcagg | 240 |
| tagagtaggg ctgccagagg ttgcgaatga aaacaggatg cccagtaaac ccgaattgca | 300 |
| gatacccag gcatgacttt gttttttgt gtaaggatgc aaaatttggg atgtatttat | 360 |
| actagaaaag ctgcttgttg tttatctgaa attcagagtt atcaggtgtt ctgtatttta | 420 |
| cctccatcct gggggaggcg tcctcctcct ggctctgcag atgagggagc cgaggctcag | 480 |
| agaggctgaa tgtgctgccc atggtcccac atccatgtgt ggctgcacca ggacctgacc | 540 |

```
tgtccttggc gtgcgggttg ttctctggag agtaaggtgg ctgtggggaa catcaataaa    600
cccccatctc ttctag                                                    616
```

<210> SEQ ID NO 4
<211> LENGTH: 20
<212> TYPE: DNA
<213> ORGANISM: Artificial Sequence
<220> FEATURE:
<223> OTHER INFORMATION: Antisense oligomer-GAA-IVS1(-39-20)
<220> FEATURE:
<221> NAME/KEY: misc_feature
<222> LOCATION: (1)..(20)
<223> OTHER INFORMATION: n is t or u

<400> SEQUENCE: 4

```
gcncagcagg gaggcgggag                                                 20
```

<210> SEQ ID NO 5
<211> LENGTH: 20
<212> TYPE: DNA
<213> ORGANISM: Artificial Sequence
<220> FEATURE:
<223> OTHER INFORMATION: Antisense oligomer-GAA-IVS1(-74-55)
<220> FEATURE:
<221> NAME/KEY: misc_feature
<222> LOCATION: (1)..(20)
<223> OTHER INFORMATION: n is t or u

<400> SEQUENCE: 5

```
ggcncncaaa gcagcncnga                                                 20
```

<210> SEQ ID NO 6
<211> LENGTH: 25
<212> TYPE: DNA
<213> ORGANISM: Artificial Sequence
<220> FEATURE:
<223> OTHER INFORMATION: Antisense oligomer-GAA-IVS1(-99-75)
<220> FEATURE:
<221> NAME/KEY: misc_feature
<222> LOCATION: (1)..(25)
<223> OTHER INFORMATION: n is t or u

<400> SEQUENCE: 6

```
gacancaacc gcggcnggca cngca                                           25
```

<210> SEQ ID NO 7
<211> LENGTH: 25
<212> TYPE: DNA
<213> ORGANISM: Artificial Sequence
<220> FEATURE:
<223> OTHER INFORMATION: Antisense oligomer-GAA-IVS1(-139-115)
<220> FEATURE:
<221> NAME/KEY: misc_feature
<222> LOCATION: (1)..(25)
<223> OTHER INFORMATION: n is t or u

<400> SEQUENCE: 7

```
gggnaaggng gccagggngg gngnn                                           25
```

<210> SEQ ID NO 8
<211> LENGTH: 19
<212> TYPE: DNA
<213> ORGANISM: Artificial Sequence
<220> FEATURE:
<223> OTHER INFORMATION: Antisense oligomer-GAA-IVS1(-158-140)
<220> FEATURE:
<221> NAME/KEY: misc_feature
<222> LOCATION: (1)..(19)
<223> OTHER INFORMATION: n is t or u

```
<400> SEQUENCE: 8
gcccngcngn cnagacngg                                                19

<210> SEQ ID NO 9
<211> LENGTH: 20
<212> TYPE: DNA
<213> ORGANISM: Artificial Sequence
<220> FEATURE:
<223> OTHER INFORMATION: Antisense oligomer-GAA-IVS1(-179-160)

<400> SEQUENCE: 9
gagagggcca gaaggaaggg                                               20

<210> SEQ ID NO 10
<211> LENGTH: 17
<212> TYPE: DNA
<213> ORGANISM: Artificial Sequence
<220> FEATURE:
<223> OTHER INFORMATION: Antisense oligomer-GAA-IVS2(-4-20)
<220> FEATURE:
<221> NAME/KEY: misc_feature
<222> LOCATION: (1)..(17)
<223> OTHER INFORMATION: n is t or u

<400> SEQUENCE: 10
cccgccccng cccngcc                                                  17

<210> SEQ ID NO 11
<211> LENGTH: 18
<212> TYPE: DNA
<213> ORGANISM: Artificial Sequence
<220> FEATURE:
<223> OTHER INFORMATION: Antisense oligomer-GAA-IVS2(-14-30)
<220> FEATURE:
<221> NAME/KEY: misc_feature
<222> LOCATION: (1)..(18)
<223> OTHER INFORMATION: n is t or u

<400> SEQUENCE: 11
nggccgccgc ccccgccc                                                 18

<210> SEQ ID NO 12
<211> LENGTH: 20
<212> TYPE: DNA
<213> ORGANISM: Artificial Sequence
<220> FEATURE:
<223> OTHER INFORMATION: Antisense oligomer-GAA-IVS2(-33-52)
<220> FEATURE:
<221> NAME/KEY: misc_feature
<222> LOCATION: (1)..(20)
<223> OTHER INFORMATION: n is t or u

<400> SEQUENCE: 12
ngnccacgcg cacccncngc                                               20

<210> SEQ ID NO 13

<400> SEQUENCE: 13

000

<210> SEQ ID NO 14
<211> LENGTH: 20
<212> TYPE: DNA
<213> ORGANISM: Artificial Sequence
<220> FEATURE:
<223> OTHER INFORMATION: Antisense oligomer-GAA-IVS2(-73-92)
```

```
<220> FEATURE:
<221> NAME/KEY: misc_feature
<222> LOCATION: (1)..(20)
<223> OTHER INFORMATION: n is t or u

<400> SEQUENCE: 14
gcaacangca ccccacccnn                                           20

<210> SEQ ID NO 15
<211> LENGTH: 20
<212> TYPE: DNA
<213> ORGANISM: Artificial Sequence
<220> FEATURE:
<223> OTHER INFORMATION: Antisense oligomer-GAA-IVS2(-93-112)
<220> FEATURE:
<221> NAME/KEY: misc_feature
<222> LOCATION: (1)..(20)
<223> OTHER INFORMATION: n is t or u

<400> SEQUENCE: 15
agggcccagc acacagnggn                                           20

<210> SEQ ID NO 16
<211> LENGTH: 20
<212> TYPE: DNA
<213> ORGANISM: Artificial Sequence
<220> FEATURE:
<223> OTHER INFORMATION: Antisense oligomer-GAA-IVS2(-113-132)
<220> FEATURE:
<221> NAME/KEY: misc_feature
<222> LOCATION: (1)..(20)
<223> OTHER INFORMATION: n is t or u

<400> SEQUENCE: 16
ncacaccncc gcncccagca                                           20

<210> SEQ ID NO 17
<211> LENGTH: 18
<212> TYPE: DNA
<213> ORGANISM: Artificial Sequence
<220> FEATURE:
<223> OTHER INFORMATION: Antisense oligomer-GAA-IVS2(-133-150)
<220> FEATURE:
<221> NAME/KEY: misc_feature
<222> LOCATION: (1)..(18)
<223> OTHER INFORMATION: n is t or u

<400> SEQUENCE: 17
ggcgcngcca nngncngc                                             18

<210> SEQ ID NO 18
<211> LENGTH: 20
<212> TYPE: DNA
<213> ORGANISM: Artificial Sequence
<220> FEATURE:
<223> OTHER INFORMATION: Antisense oligomer-GAA-IVS2(-153-172)
<220> FEATURE:
<221> NAME/KEY: misc_feature
<222> LOCATION: (1)..(20)
<223> OTHER INFORMATION: n is t or u

<400> SEQUENCE: 18
gngnccccac ngcnccccga                                           20

<210> SEQ ID NO 19
<211> LENGTH: 20
<212> TYPE: DNA
<213> ORGANISM: Artificial Sequence
<220> FEATURE:
```

```
<223> OTHER INFORMATION: Antisense oligomer-GAA-IVS2(-173-192)
<220> FEATURE:
<221> NAME/KEY: misc_feature
<222> LOCATION: (1)..(20)
<223> OTHER INFORMATION: n is t or u

<400> SEQUENCE: 19
cnggagnacc ngncaccgng                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense oligomer-GAA-IVS2(-193-212)
<220> FEATURE:
<221> NAME/KEY: misc_feature
<222> LOCATION: (1)..(20)
<223> OTHER INFORMATION: n is t or u

<400> SEQUENCE: 20
ngagccccga gcccngccnn                                              20

<210> SEQ ID NO 21
<211> LENGTH: 25
<212> TYPE: DNA
<213> ORGANISM: Artificial Sequence
<220> FEATURE:
<223> OTHER INFORMATION: Antisense oligomer-GAA-IVS2(-213-237)
<220> FEATURE:
<221> NAME/KEY: misc_feature
<222> LOCATION: (1)..(25)
<223> OTHER INFORMATION: n is t or u

<400> SEQUENCE: 21
ngacccaccn nnncanaaag angaa                                        25

<210> SEQ ID NO 22
<211> LENGTH: 25
<212> TYPE: DNA
<213> ORGANISM: Artificial Sequence
<220> FEATURE:
<223> OTHER INFORMATION: Antisense oligomer-GAA-IVS2(-234-258)
<220> FEATURE:
<221> NAME/KEY: misc_feature
<222> LOCATION: (1)..(25)
<223> OTHER INFORMATION: n is t or u

<400> SEQUENCE: 22
cncnggcagc ccnacncnac cngac                                        25

<210> SEQ ID NO 23
<211> LENGTH: 27
<212> TYPE: DNA
<213> ORGANISM: Artificial Sequence
<220> FEATURE:
<223> OTHER INFORMATION: Antisense oligomer-GAA-IVS2(-338-364)
<220> FEATURE:
<221> NAME/KEY: misc_feature
<222> LOCATION: (1)..(27)
<223> OTHER INFORMATION: n is t or u

<400> SEQUENCE: 23
cnagnanaaa nacancccaa annnngc                                      27

<210> SEQ ID NO 24
<211> LENGTH: 25
<212> TYPE: DNA
<213> ORGANISM: Artificial Sequence
```

```
<220> FEATURE:
<223> OTHER INFORMATION: Antisense oligomer-GAAEx2A(+202+226)
<220> FEATURE:
<221> NAME/KEY: misc_feature
<222> LOCATION: (1)..(25)
<223> OTHER INFORMATION: n is t or u

<400> SEQUENCE: 24
ggcccnggnc ngcnggcncc cngcn                                           25

<210> SEQ ID NO 25
<211> LENGTH: 25
<212> TYPE: DNA
<213> ORGANISM: Artificial Sequence
<220> FEATURE:
<223> OTHER INFORMATION: Antisense oligomer-GAAEx2A(+367+391)
<220> FEATURE:
<221> NAME/KEY: misc_feature
<222> LOCATION: (1)..(25)
<223> OTHER INFORMATION: n is t or u

<400> SEQUENCE: 25 gcnccongca gccccngcnn ngcag                                           25

<210> SEQ ID NO 26
<211> LENGTH: 20
<212> TYPE: DNA
<213> ORGANISM: Artificial Sequence
<220> FEATURE:
<223> OTHER INFORMATION: Antisense oligomer-GAA-IVS1.4.20
<220> FEATURE:
<221> NAME/KEY: misc_feature
<222> LOCATION: (1)..(20)
<223> OTHER INFORMATION: n is t or u

<400> SEQUENCE: 26
ggggcagacg ncaggngncn                                                 20

<210> SEQ ID NO 27
<211> LENGTH: 20
<212> TYPE: DNA
<213> ORGANISM: Artificial Sequence
<220> FEATURE:
<223> OTHER INFORMATION: Antisense oligomer-GAA-IVS1.6.20
<220> FEATURE:
<221> NAME/KEY: misc_feature
<222> LOCATION: (1)..(20)
<223> OTHER INFORMATION: n is t or u

<400> SEQUENCE: 27
gcggggcaga cgncaggngn                                                 20

<210> SEQ ID NO 28
<211> LENGTH: 20
<212> TYPE: DNA
<213> ORGANISM: Artificial Sequence
<220> FEATURE:
<223> OTHER INFORMATION: Antisense oligomer-GAA-IVS1.8.20
<220> FEATURE:
<221> NAME/KEY: misc_feature
<222> LOCATION: (1)..(20)
<223> OTHER INFORMATION: n is t or u

<400> SEQUENCE: 28
gcgcggggca gacgncaggn                                                 20

<210> SEQ ID NO 29
<211> LENGTH: 20
<212> TYPE: DNA
```

```
<213> ORGANISM: Artificial Sequence
<220> FEATURE:
<223> OTHER INFORMATION: Antisense oligomer-GAA-IVS1.10.20
<220> FEATURE:
<221> NAME/KEY: misc_feature
<222> LOCATION: (1)..(20)
<223> OTHER INFORMATION: n is t or u

<400> SEQUENCE: 29
cagcgcgggg cagacgncag                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense oligomer-GAA-IVS1.12.20
<220> FEATURE:
<221> NAME/KEY: misc_feature
<222> LOCATION: (1)..(20)
<223> OTHER INFORMATION: n is t or u

<400> SEQUENCE: 30
ggcagcgcgg ggcagacgnc                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense oligomer-GAA-IVS1.14.20

<400> SEQUENCE: 31
ccggcagcgc ggggcagacg                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense oligomer-GAA-IVS1.15.20

<400> SEQUENCE: 32
gccggcagcg cggggcagac                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense oligomer-GAA-IVS1.17.20

<400> SEQUENCE: 33
ccgccggcag cgcggggcag                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense oligomer-GAA-IVS1.21.20
<220> FEATURE:
<221> NAME/KEY: misc_feature
<222> LOCATION: (1)..(20)
<223> OTHER INFORMATION: n is t or u

<400> SEQUENCE: 34
gnnaccgccg gcagcgcggg                                              20
```

```
<210> SEQ ID NO 35
<211> LENGTH: 20
<212> TYPE: DNA
<213> ORGANISM: Artificial Sequence
<220> FEATURE:
<223> OTHER INFORMATION: Antisense oligomer-GAA-IVS1.24.20
<220> FEATURE:
<221> NAME/KEY: misc_feature
<222> LOCATION: (1)..(20)
<223> OTHER INFORMATION: n is t or u

<400> SEQUENCE: 35
gangnnaccg ccggcagcgc                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense oligomer-GAA-IVS1.26.20
<220> FEATURE:
<221> NAME/KEY: misc_feature
<222> LOCATION: (1)..(20)
<223> OTHER INFORMATION: n is t or u

<400> SEQUENCE: 36
gggangnnac cgccggcagc                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense oligomer-GAA-IVS1.28.20
<220> FEATURE:
<221> NAME/KEY: misc_feature
<222> LOCATION: (1)..(20)
<223> OTHER INFORMATION: n is t or u

<400> SEQUENCE: 37
cngggangnn accgccggca                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense oligomer-GAA-IVS1.30.20
<220> FEATURE:
<221> NAME/KEY: misc_feature
<222> LOCATION: (1)..(20)
<223> OTHER INFORMATION: n is t or u

<400> SEQUENCE: 38
nncngggang nnaccgccgg                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense oligomer-GAA-IVS1.32.20
<220> FEATURE:
<221> NAME/KEY: misc_feature
<222> LOCATION: (1)..(20)
<223> OTHER INFORMATION: n is t or u

<400> SEQUENCE: 39
```
gcnncnggga ngnnaccgcc 20

<210> SEQ ID NO 40
<211> LENGTH: 20
<212> TYPE: DNA
<213> ORGANISM: Artificial Sequence
<220> FEATURE:
<223> OTHER INFORMATION: Antisense oligomer-GAA-IVS1.2013.20
<220> FEATURE:
<221> NAME/KEY: misc_feature
<222> LOCATION: (1)..(20)
<223> OTHER INFORMATION: n is t or u

<400> SEQUENCE: 40
gcaacncgna ngnccnnagg 20

<210> SEQ ID NO 41
<211> LENGTH: 20
<212> TYPE: DNA
<213> ORGANISM: Artificial Sequence
<220> FEATURE:
<223> OTHER INFORMATION: Antisense oligomer-GAA-IVS1.2015.20
<220> FEATURE:
<221> NAME/KEY: misc_feature
<222> LOCATION: (1)..(20)
<223> OTHER INFORMATION: n is t or u

<400> SEQUENCE: 41
nggcaacncg nangnccnna 20

<210> SEQ ID NO 42
<211> LENGTH: 20
<212> TYPE: DNA
<213> ORGANISM: Artificial Sequence
<220> FEATURE:
<223> OTHER INFORMATION: Antisense oligomer-GAA-IVS1.2017.20
<220> FEATURE:
<221> NAME/KEY: misc_feature
<222> LOCATION: (1)..(20)
<223> OTHER INFORMATION: n is t or u

<400> SEQUENCE: 42
ncnggcaacn cgnangnccn 20

<210> SEQ ID NO 43
<211> LENGTH: 20
<212> TYPE: DNA
<213> ORGANISM: Artificial Sequence
<220> FEATURE:
<223> OTHER INFORMATION: Antisense oligomer-GAA-IVS1.2019.20
<220> FEATURE:
<221> NAME/KEY: misc_feature
<222> LOCATION: (1)..(20)
<223> OTHER INFORMATION: n is t or u

<400> SEQUENCE: 43
anncnggcaa cncgnangnc 20

<210> SEQ ID NO 44
<211> LENGTH: 20
<212> TYPE: DNA
<213> ORGANISM: Artificial Sequence
<220> FEATURE:
<223> OTHER INFORMATION: Antisense oligomer-GAA-IVS1.2022.20
<220> FEATURE:
<221> NAME/KEY: misc_feature
<222> LOCATION: (1)..(20)
<223> OTHER INFORMATION: n is t or u

<400> SEQUENCE: 44 gngannncngg caacncgnan                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense oligomer-GAA-IVS1.2024.20
<220> FEATURE:
<221> NAME/KEY: misc_feature
<222> LOCATION: (1)..(20)
<223> OTHER INFORMATION: n is t or u

<400> SEQUENCE: 45
aagnganncn ggcaacncgn                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense oligomer-GAA-IVS1.2037.20
<220> FEATURE:
<221> NAME/KEY: misc_feature
<222> LOCATION: (1)..(20)
<223> OTHER INFORMATION: n is t or u

<400> SEQUENCE: 46
ngggngncag cggaagngan                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense oligomer-GAA-IVS1.2041.20
<220> FEATURE:
<221> NAME/KEY: misc_feature
<222> LOCATION: (1)..(20)
<223> OTHER INFORMATION: n is t or u

<400> SEQUENCE: 47
ccacngggng ncagcggaag                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense oligomer-GAA-IVS1.2043.20
<220> FEATURE:
<221> NAME/KEY: misc_feature
<222> LOCATION: (1)..(20)
<223> OTHER INFORMATION: n is t or u

<400> SEQUENCE: 48
gnccacnggg ngncagcgga                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense oligomer-GAA-IVS1.2045.20
<220> FEATURE:
<221> NAME/KEY: misc_feature
<222> LOCATION: (1)..(20)
<223> OTHER INFORMATION: n is t or u

```
<400> SEQUENCE: 49
nggnccacng ggngncagcg                                         20

<210> SEQ ID NO 50
<211> LENGTH: 20
<212> TYPE: DNA
<213> ORGANISM: Artificial Sequence
<220> FEATURE:
<223> OTHER INFORMATION: Antisense oligomer-GAA-IVS1.2048.20
<220> FEATURE:
<221> NAME/KEY: misc_feature
<222> LOCATION: (1)..(20)
<223> OTHER INFORMATION: n is t or u

<400> SEQUENCE: 50
gcnnggncca cnggngnca                                          20

<210> SEQ ID NO 51
<211> LENGTH: 20
<212> TYPE: DNA
<213> ORGANISM: Artificial Sequence
<220> FEATURE:
<223> OTHER INFORMATION: Antisense oligomer-GAA-IVS1.2069.20
<220> FEATURE:
<221> NAME/KEY: misc_feature
<222> LOCATION: (1)..(20)
<223> OTHER INFORMATION: n is t or u

<400> SEQUENCE: 51
ccacnncngc anaaaggngc                                         20

<210> SEQ ID NO 52
<211> LENGTH: 20
<212> TYPE: DNA
<213> ORGANISM: Artificial Sequence
<220> FEATURE:
<223> OTHER INFORMATION: Antisense oligomer-GAA-IVS1.2071.20
<220> FEATURE:
<221> NAME/KEY: misc_feature
<222> LOCATION: (1)..(20)
<223> OTHER INFORMATION: n is t or u

<400> SEQUENCE: 52
ccccacnncn gcanaaaggn                                         20

<210> SEQ ID NO 53
<211> LENGTH: 20
<212> TYPE: DNA
<213> ORGANISM: Artificial Sequence
<220> FEATURE:
<223> OTHER INFORMATION: Antisense oligomer-GAA-IVS1.2073.20
<220> FEATURE:
<221> NAME/KEY: misc_feature
<222> LOCATION: (1)..(20)
<223> OTHER INFORMATION: n is t or u

<400> SEQUENCE: 53
agccccacnn cngcanaaag                                         20

<210> SEQ ID NO 54
<211> LENGTH: 20
<212> TYPE: DNA
<213> ORGANISM: Artificial Sequence
<220> FEATURE:
<223> OTHER INFORMATION: Antisense oligomer-GAA-IVS1.2075.20
<220> FEATURE:
<221> NAME/KEY: misc_feature
<222> LOCATION: (1)..(20)
<223> OTHER INFORMATION: n is t or u
```

<400> SEQUENCE: 54
ggagccccac nncngcanaa                                                20

<210> SEQ ID NO 55
<211> LENGTH: 20
<212> TYPE: DNA
<213> ORGANISM: Artificial Sequence
<220> FEATURE:
<223> OTHER INFORMATION: Antisense oligomer-GAA-IVS1.2077.20
<220> FEATURE:
<221> NAME/KEY: misc_feature
<222> LOCATION: (1)..(20)
<223> OTHER INFORMATION: n is t or u

<400> SEQUENCE: 55
ngggagcccc acnncngcan                                                20

<210> SEQ ID NO 56
<211> LENGTH: 20
<212> TYPE: DNA
<213> ORGANISM: Artificial Sequence
<220> FEATURE:
<223> OTHER INFORMATION: Antisense oligomer-GAA-IVS1.2079.20
<220> FEATURE:
<221> NAME/KEY: misc_feature
<222> LOCATION: (1)..(20)
<223> OTHER INFORMATION: n is t or u

<400> SEQUENCE: 56
gcngggagcc ccacnncngc                                                20

<210> SEQ ID NO 57
<211> LENGTH: 20
<212> TYPE: DNA
<213> ORGANISM: Artificial Sequence
<220> FEATURE:
<223> OTHER INFORMATION: Antisense oligomer-GAA-IVS1.2081.20
<220> FEATURE:
<221> NAME/KEY: misc_feature
<222> LOCATION: (1)..(20)
<223> OTHER INFORMATION: n is t or u

<400> SEQUENCE: 57
nggcngggag ccccacnncn                                                20

<210> SEQ ID NO 58
<211> LENGTH: 20
<212> TYPE: DNA
<213> ORGANISM: Artificial Sequence
<220> FEATURE:
<223> OTHER INFORMATION: Antisense oligomer-GAA-IVS1.2088.20
<220> FEATURE:
<221> NAME/KEY: misc_feature
<222> LOCATION: (1)..(20)
<223> OTHER INFORMATION: n is t or u

<400> SEQUENCE: 58
ccacgccngg cnggagccc                                                 20

<210> SEQ ID NO 59
<211> LENGTH: 20
<212> TYPE: DNA
<213> ORGANISM: Artificial Sequence
<220> FEATURE:
<223> OTHER INFORMATION: Antisense oligomer-GAA-IVS1.2115.20
<220> FEATURE:
<221> NAME/KEY: misc_feature
<222> LOCATION: (1)..(20)

<223> OTHER INFORMATION: n is t or u

<400> SEQUENCE: 59
nccgaagngc ngggannnca                                        20

<210> SEQ ID NO 60
<211> LENGTH: 20
<212> TYPE: DNA
<213> ORGANISM: Artificial Sequence
<220> FEATURE:
<223> OTHER INFORMATION: Antisense oligomer-GAA-IVS1.2132.20
<220> FEATURE:
<221> NAME/KEY: misc_feature
<222> LOCATION: (1)..(20)
<223> OTHER INFORMATION: n is t or u

<400> SEQUENCE: 60
nccacccccc nnggccnncc                                        20

<210> SEQ ID NO 61
<211> LENGTH: 20
<212> TYPE: DNA
<213> ORGANISM: Artificial Sequence
<220> FEATURE:
<223> OTHER INFORMATION: Antisense oligomer-GAA-IVS1.2135.20
<220> FEATURE:
<221> NAME/KEY: misc_feature
<222> LOCATION: (1)..(20)
<223> OTHER INFORMATION: n is t or u

<400> SEQUENCE: 61
nganccaccc cccnnggccn                                        20

<210> SEQ ID NO 62
<211> LENGTH: 20
<212> TYPE: DNA
<213> ORGANISM: Artificial Sequence
<220> FEATURE:
<223> OTHER INFORMATION: Antisense oligomer-GAA-IVS1.2140.20
<220> FEATURE:
<221> NAME/KEY: misc_feature
<222> LOCATION: (1)..(20)
<223> OTHER INFORMATION: n is t or u

<400> SEQUENCE: 62
ncaagnganc caccccccnn                                        20

<210> SEQ ID NO 63
<211> LENGTH: 20
<212> TYPE: DNA
<213> ORGANISM: Artificial Sequence
<220> FEATURE:
<223> OTHER INFORMATION: Antisense oligomer-GAA-IVS1.2143.20
<220> FEATURE:
<221> NAME/KEY: misc_feature
<222> LOCATION: (1)..(20)
<223> OTHER INFORMATION: n is t or u

<400> SEQUENCE: 63
agcncaagng anccacccccc                                       20

<210> SEQ ID NO 64
<211> LENGTH: 20
<212> TYPE: DNA
<213> ORGANISM: Artificial Sequence
<220> FEATURE:
<223> OTHER INFORMATION: Antisense oligomer-GAA-IVS1.2152.20
<220> FEATURE:
<221> NAME/KEY: misc_feature
<222> LOCATION: (1)..(20)
<223> OTHER INFORMATION: n is t or u

<400> SEQUENCE: 64
gaacnccnga gcncaagnga                                                     20

<210> SEQ ID NO 65
<211> LENGTH: 20
<212> TYPE: DNA
<213> ORGANISM: Artificial Sequence
<220> FEATURE:
<223> OTHER INFORMATION: Antisense oligomer-GAA-IVS1.2156.20
<220> FEATURE:
<221> NAME/KEY: misc_feature
<222> LOCATION: (1)..(20)
<223> OTHER INFORMATION: n is t or u

<400> SEQUENCE: 65
ncncgaacnc cngagcncaa                                                     20

<210> SEQ ID NO 66
<211> LENGTH: 20
<212> TYPE: DNA
<213> ORGANISM: Artificial Sequence
<220> FEATURE:
<223> OTHER INFORMATION: Antisense oligomer-GAA-IVS1.2163.20
<220> FEATURE:
<221> NAME/KEY: misc_feature
<222> LOCATION: (1)..(20)
<223> OTHER INFORMATION: n is t or u

<400> SEQUENCE: 66
aggcnggncn cgaacnccng                                                     20

<210> SEQ ID NO 67
<211> LENGTH: 20
<212> TYPE: DNA
<213> ORGANISM: Artificial Sequence
<220> FEATURE:
<223> OTHER INFORMATION: Antisense oligomer-GAA-IVS1.2165.20
<220> FEATURE:
<221> NAME/KEY: misc_feature
<222> LOCATION: (1)..(20)
<223> OTHER INFORMATION: n is t or u

<400> SEQUENCE: 67
ccaggcnggn cncgaacncc                                                     20

<210> SEQ ID NO 68
<211> LENGTH: 20
<212> TYPE: DNA
<213> ORGANISM: Artificial Sequence
<220> FEATURE:
<223> OTHER INFORMATION: Antisense oligomer-GAA-IVS1.2178.20
<220> FEATURE:
<221> NAME/KEY: misc_feature
<222> LOCATION: (1)..(20)
<223> OTHER INFORMATION: n is t or u

<400> SEQUENCE: 68
nnngccangn nacccaggcn                                                     20

<210> SEQ ID NO 69
<211> LENGTH: 20
<212> TYPE: DNA
<213> ORGANISM: Artificial Sequence
<220> FEATURE:
<223> OTHER INFORMATION: Antisense oligomer-GAA-IVS1.2183.20
<220> FEATURE:

<221> NAME/KEY: misc_feature
<222> LOCATION: (1)..(20)
<223> OTHER INFORMATION: n is t or u

<400> SEQUENCE: 69
gggannnngc cangnnaccc                                        20

<210> SEQ ID NO 70
<211> LENGTH: 20
<212> TYPE: DNA
<213> ORGANISM: Artificial Sequence
<220> FEATURE:
<223> OTHER INFORMATION: Antisense oligomer-GAA-IVS1.2185.20
<220> FEATURE:
<221> NAME/KEY: misc_feature
<222> LOCATION: (1)..(20)
<223> OTHER INFORMATION: n is t or u

<400> SEQUENCE: 70
acgggannnn gccangnnac                                        20

<210> SEQ ID NO 71
<211> LENGTH: 20
<212> TYPE: DNA
<213> ORGANISM: Artificial Sequence
<220> FEATURE:
<223> OTHER INFORMATION: Antisense oligomer-GAA-IVS1.2188.20
<220> FEATURE:
<221> NAME/KEY: misc_feature
<222> LOCATION: (1)..(20)
<223> OTHER INFORMATION: n is t or u

<400> SEQUENCE: 71
gagacgggan nnngccangn                                        20

<210> SEQ ID NO 72
<211> LENGTH: 20
<212> TYPE: DNA
<213> ORGANISM: Artificial Sequence
<220> FEATURE:
<223> OTHER INFORMATION: Antisense oligomer-GAA-IVS1.2190.20
<220> FEATURE:
<221> NAME/KEY: misc_feature
<222> LOCATION: (1)..(20)
<223> OTHER INFORMATION: n is t or u

<400> SEQUENCE: 72
nagagacggg annnngccan                                        20

<210> SEQ ID NO 73
<211> LENGTH: 20
<212> TYPE: DNA
<213> ORGANISM: Artificial Sequence
<220> FEATURE:
<223> OTHER INFORMATION: Antisense oligomer-GAA-IVS1.2195.20
<220> FEATURE:
<221> NAME/KEY: misc_feature
<222> LOCATION: (1)..(20)
<223> OTHER INFORMATION: n is t or u

<400> SEQUENCE: 73
nnnngnagag acgggannnn                                        20

<210> SEQ ID NO 74
<211> LENGTH: 20
<212> TYPE: DNA
<213> ORGANISM: Artificial Sequence
<220> FEATURE:
<223> OTHER INFORMATION: Antisense oligomer-GAA-IVS1.2200.20

```
<220> FEATURE:
<221> NAME/KEY: misc_feature
<222> LOCATION: (1)..(20)
<223> OTHER INFORMATION: n is t or u

<400> SEQUENCE: 74
ngnannnnng nagagacggg                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense oligomer-GAA-IVS1.2202.20
<220> FEATURE:
<221> NAME/KEY: misc_feature
<222> LOCATION: (1)..(20)
<223> OTHER INFORMATION: n is t or u

<400> SEQUENCE: 75
ncngnannnn ngnagagacg                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense oligomer-GAA-IVS1.2204.20
<220> FEATURE:
<221> NAME/KEY: misc_feature
<222> LOCATION: (1)..(20)
<223> OTHER INFORMATION: n is t or u

<400> SEQUENCE: 76
nnncngnann nnngnagaga                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense oligomer-GAA-IVS1.2206.20
<220> FEATURE:
<221> NAME/KEY: misc_feature
<222> LOCATION: (1)..(20)
<223> OTHER INFORMATION: n is t or u

<400> SEQUENCE: 77
annnncngna nnnnngnaga                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense oligomer-GAA-IVS1.2208.20
<220> FEATURE:
<221> NAME/KEY: misc_feature
<222> LOCATION: (1)..(20)
<223> OTHER INFORMATION: n is t or u

<400> SEQUENCE: 78
naannnncng nannnnngna                                              20

<210> SEQ ID NO 79
<211> LENGTH: 20
<212> TYPE: DNA
<213> ORGANISM: Artificial Sequence
<220> FEATURE:
```

```
<223> OTHER INFORMATION: Antisense oligomer-GAA-IVS1.2210.20
<220> FEATURE:
<221> NAME/KEY: misc_feature
<222> LOCATION: (1)..(20)
<223> OTHER INFORMATION: n is t or u

<400> SEQUENCE: 79
gcnaannnnc ngnannnnng                                         20

<210> SEQ ID NO 80
<211> LENGTH: 20
<212> TYPE: DNA
<213> ORGANISM: Artificial Sequence
<220> FEATURE:
<223> OTHER INFORMATION: Antisense oligomer-GAA-IVS2.1.20
<220> FEATURE:
<221> NAME/KEY: misc_feature
<222> LOCATION: (1)..(20)
<223> OTHER INFORMATION: n is t or u

<400> SEQUENCE: 80
cccgccccng cccngcccac                                         20

<210> SEQ ID NO 81
<211> LENGTH: 20
<212> TYPE: DNA
<213> ORGANISM: Artificial Sequence
<220> FEATURE:
<223> OTHER INFORMATION: Antisense oligomer-GAA-IVS2.6.20
<220> FEATURE:
<221> NAME/KEY: misc_feature
<222> LOCATION: (1)..(20)
<223> OTHER INFORMATION: n is t or u

<400> SEQUENCE: 81 ccgccccgc cccngcccng                                          20

<210> SEQ ID NO 82
<211> LENGTH: 20
<212> TYPE: DNA
<213> ORGANISM: Artificial Sequence
<220> FEATURE:
<223> OTHER INFORMATION: Antisense oligomer-GAA-IVS2.9.20
<220> FEATURE:
<221> NAME/KEY: misc_feature
<222> LOCATION: (1)..(20)
<223> OTHER INFORMATION: n is t or u

<400> SEQUENCE: 82
ccgccgcccc cgccccngcc                                         20

<210> SEQ ID NO 83
<211> LENGTH: 20
<212> TYPE: DNA
<213> ORGANISM: Artificial Sequence
<220> FEATURE:
<223> OTHER INFORMATION: Antisense oligomer-GAA-IVS2.12.20
<220> FEATURE:
<221> NAME/KEY: misc_feature
<222> LOCATION: (1)..(20)
<223> OTHER INFORMATION: n is t or u

<400> SEQUENCE: 83
nggccgccgc ccccgccccn                                         20

<210> SEQ ID NO 84
<211> LENGTH: 20
<212> TYPE: DNA
<213> ORGANISM: Artificial Sequence
```

```
<220> FEATURE:
<223> OTHER INFORMATION: Antisense oligomer-GAA-IVS2.18.20
<220> FEATURE:
<221> NAME/KEY: misc_feature
<222> LOCATION: (1)..(20)
<223> OTHER INFORMATION: n is t or u

<400> SEQUENCE: 84
cngcccnggc cgccgccccc                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense oligomer-GAA-IVS2.24.20
<220> FEATURE:
<221> NAME/KEY: misc_feature
<222> LOCATION: (1)..(20)
<223> OTHER INFORMATION: n is t or u

<400> SEQUENCE: 85
cacccncngc ccnggccgcc                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense oligomer-GAA-IVS2.27.20
<220> FEATURE:
<221> NAME/KEY: misc_feature
<222> LOCATION: (1)..(20)
<223> OTHER INFORMATION: n is t or u

<400> SEQUENCE: 86
gcgcacccnc ngcccnggcc                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense oligomer-GAA-IVS2.40.20
<220> FEATURE:
<221> NAME/KEY: misc_feature
<222> LOCATION: (1)..(20)
<223> OTHER INFORMATION: n is t or u

<400> SEQUENCE: 87
ngncgangnc cacgcgcacc                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense oligomer-GAA-IVS2.45.20
<220> FEATURE:
<221> NAME/KEY: misc_feature
<222> LOCATION: (1)..(20)
<223> OTHER INFORMATION: n is t or u

<400> SEQUENCE: 88
gngggngncg angnccacgc                                              20

<210> SEQ ID NO 89
<211> LENGTH: 20
<212> TYPE: DNA
```

<213> ORGANISM: Artificial Sequence
<220> FEATURE:
<223> OTHER INFORMATION: Antisense oligomer-GAA-IVS2.48.20
<220> FEATURE:
<221> NAME/KEY: misc_feature
<222> LOCATION: (1)..(20)
<223> OTHER INFORMATION: n is t or u

<400> SEQUENCE: 89
ngcgngggng ncgangncca    20

<210> SEQ ID NO 90
<211> LENGTH: 20
<212> TYPE: DNA
<213> ORGANISM: Artificial Sequence
<220> FEATURE:
<223> OTHER INFORMATION: Antisense oligomer-GAA-IVS2.54.20
<220> FEATURE:
<221> NAME/KEY: misc_feature
<222> LOCATION: (1)..(20)
<223> OTHER INFORMATION: n is t or u

<400> SEQUENCE: 90
gngaggngcg ngggngncga    20

<210> SEQ ID NO 91
<211> LENGTH: 20
<212> TYPE: DNA
<213> ORGANISM: Artificial Sequence
<220> FEATURE:
<223> OTHER INFORMATION: Antisense oligomer-GAA-IVS2.67.20
<220> FEATURE:
<221> NAME/KEY: misc_feature
<222> LOCATION: (1)..(20)
<223> OTHER INFORMATION: n is t or u

<400> SEQUENCE: 91
gcaccccacc cnngngaggn    20

<210> SEQ ID NO 92
<211> LENGTH: 20
<212> TYPE: DNA
<213> ORGANISM: Artificial Sequence
<220> FEATURE:
<223> OTHER INFORMATION: Antisense oligomer-GAA-IVS2.72.20
<220> FEATURE:
<221> NAME/KEY: misc_feature
<222> LOCATION: (1)..(20)
<223> OTHER INFORMATION: n is t or u

<400> SEQUENCE: 92
aacangcacc ccacccnngn    20

<210> SEQ ID NO 93
<211> LENGTH: 20
<212> TYPE: DNA
<213> ORGANISM: Artificial Sequence
<220> FEATURE:
<223> OTHER INFORMATION: Antisense oligomer-GAA-IVS2.431.20
<220> FEATURE:
<221> NAME/KEY: misc_feature
<222> LOCATION: (1)..(20)
<223> OTHER INFORMATION: n is t or u

<400> SEQUENCE: 93
aggaggagga cgccnccccc    20

<210> SEQ ID NO 94
<211> LENGTH: 20

```
<212> TYPE: DNA
<213> ORGANISM: Artificial Sequence
<220> FEATURE:
<223> OTHER INFORMATION: Antisense oligomer-GAA-IVS2.446.20
<220> FEATURE:
<221> NAME/KEY: misc_feature
<222> LOCATION: (1)..(20)
<223> OTHER INFORMATION: n is t or u

<400> SEQUENCE: 94
cncancngca gagccaggag                                                      20

<210> SEQ ID NO 95
<211> LENGTH: 20
<212> TYPE: DNA
<213> ORGANISM: Artificial Sequence
<220> FEATURE:
<223> OTHER INFORMATION: Antisense oligomer-GAA-IVS2.448.20
<220> FEATURE:
<221> NAME/KEY: misc_feature
<222> LOCATION: (1)..(20)
<223> OTHER INFORMATION: n is t or u

<400> SEQUENCE: 95
cccncancng cagagccagg                                                      20

<210> SEQ ID NO 96
<211> LENGTH: 20
<212> TYPE: DNA
<213> ORGANISM: Artificial Sequence
<220> FEATURE:
<223> OTHER INFORMATION: Antisense oligomer-GAA-IVS2.450.20
<220> FEATURE:
<221> NAME/KEY: misc_feature
<222> LOCATION: (1)..(20)
<223> OTHER INFORMATION: n is t or u

<400> SEQUENCE: 96 cnccncanc ngcagagcca                                                       20

<210> SEQ ID NO 97
<211> LENGTH: 20
<212> TYPE: DNA
<213> ORGANISM: Artificial Sequence
<220> FEATURE:
<223> OTHER INFORMATION: Antisense oligomer-GAA-IVS2.451.20
<220> FEATURE:
<221> NAME/KEY: misc_feature
<222> LOCATION: (1)..(20)
<223> OTHER INFORMATION: n is t or u

<400> SEQUENCE: 97
gcncccncan cngcagagcc                                                      20

<210> SEQ ID NO 98
<211> LENGTH: 20
<212> TYPE: DNA
<213> ORGANISM: Artificial Sequence
<220> FEATURE:
<223> OTHER INFORMATION: Antisense oligomer-GAA-IVS2.452.20
<220> FEATURE:
<221> NAME/KEY: misc_feature
<222> LOCATION: (1)..(20)
<223> OTHER INFORMATION: n is t or u

<400> SEQUENCE: 98
ggcnccncna ncngcagagc                                                      20

<210> SEQ ID NO 99
```

```
<211> LENGTH: 20
<212> TYPE: DNA
<213> ORGANISM: Artificial Sequence
<220> FEATURE:
<223> OTHER INFORMATION: Antisense oligomer-GAA-IVS2.453.20
<220> FEATURE:
<221> NAME/KEY: misc_feature
<222> LOCATION: (1)..(20)
<223> OTHER INFORMATION: n is t or u

<400> SEQUENCE: 99
cggcncccnc ancngcagag                                                 20

<210> SEQ ID NO 100
<211> LENGTH: 20
<212> TYPE: DNA
<213> ORGANISM: Artificial Sequence
<220> FEATURE:
<223> OTHER INFORMATION: Antisense oligomer-GAA-IVS2.454.20
<220> FEATURE:
<221> NAME/KEY: misc_feature
<222> LOCATION: (1)..(20)
<223> OTHER INFORMATION: n is t or u

<400> SEQUENCE: 100
ncggcncccn cancngcaga                                                 20

<210> SEQ ID NO 101
<211> LENGTH: 20
<212> TYPE: DNA
<213> ORGANISM: Artificial Sequence
<220> FEATURE:
<223> OTHER INFORMATION: Antisense oligomer-GAA-IVS2.455.20
<220> FEATURE:
<221> NAME/KEY: misc_feature
<222> LOCATION: (1)..(20)
<223> OTHER INFORMATION: n is t or u

<400> SEQUENCE: 101
cncggcnccc ncancngcag                                                 20

<210> SEQ ID NO 102
<211> LENGTH: 20
<212> TYPE: DNA
<213> ORGANISM: Artificial Sequence
<220> FEATURE:
<223> OTHER INFORMATION: Antisense oligomer-GAA-IVS2.456.20
<220> FEATURE:
<221> NAME/KEY: misc_feature
<222> LOCATION: (1)..(20)
<223> OTHER INFORMATION: n is t or u

<400> SEQUENCE: 102
ccncggcncc cncancngca                                                 20

<210> SEQ ID NO 103
<211> LENGTH: 20
<212> TYPE: DNA
<213> ORGANISM: Artificial Sequence
<220> FEATURE:
<223> OTHER INFORMATION: Antisense oligomer-GAA-IVS2.457.20
<220> FEATURE:
<221> NAME/KEY: misc_feature
<222> LOCATION: (1)..(20)
<223> OTHER INFORMATION: n is t or u

<400> SEQUENCE: 103
gccncggcnc ccncancngc                                                 20
```

<210> SEQ ID NO 104

<400> SEQUENCE: 104

000

<210> SEQ ID NO 105
<211> LENGTH: 25
<212> TYPE: DNA
<213> ORGANISM: Artificial Sequence
<220> FEATURE:
<223> OTHER INFORMATION: Antisense oligomer-GAA-IVS1(-79-55)
<220> FEATURE:
<221> NAME/KEY: misc_feature
<222> LOCATION: (1)..(25)
<223> OTHER INFORMATION: n is t or u

<400> SEQUENCE: 105
ggcncncaaa gcagcncnga gacan                                              25

<210> SEQ ID NO 106
<211> LENGTH: 25
<212> TYPE: DNA
<213> ORGANISM: Artificial Sequence
<220> FEATURE:
<223> OTHER INFORMATION: Antisense oligomer-GAA-IVS1(-74-50)
<220> FEATURE:
<221> NAME/KEY: misc_feature
<222> LOCATION: (1)..(25)
<223> OTHER INFORMATION: n is t or u

<400> SEQUENCE: 106
cacggggcnc ncaaagcagc ncnga                                              25

<210> SEQ ID NO 107
<211> LENGTH: 20
<212> TYPE: DNA
<213> ORGANISM: Artificial Sequence
<220> FEATURE:
<223> OTHER INFORMATION: Antisense oligomer-GAA-IVS1(-79-60)
<220> FEATURE:
<221> NAME/KEY: misc_feature
<222> LOCATION: (1)..(20)
<223> OTHER INFORMATION: n is t or u

<400> SEQUENCE: 107
ncaaagcagc ncngagacan                                                    20

<210> SEQ ID NO 108
<211> LENGTH: 20
<212> TYPE: DNA
<213> ORGANISM: Artificial Sequence
<220> FEATURE:
<223> OTHER INFORMATION: Antisense oligomer-GAA-IVS1(-69-55)
<220> FEATURE:
<221> NAME/KEY: misc_feature
<222> LOCATION: (1)..(20)
<223> OTHER INFORMATION: n is t or u

<400> SEQUENCE: 108
cacggggcnc ncaaagcagc                                                    20

<210> SEQ ID NO 109

<400> SEQUENCE: 109

000

<210> SEQ ID NO 110

```
<211> LENGTH: 24
<212> TYPE: DNA
<213> ORGANISM: Artificial Sequence
<220> FEATURE:
<223> OTHER INFORMATION: Antisense oligomer-GAA-IVS1(-163-140)
<220> FEATURE:
<221> NAME/KEY: misc_feature
<222> LOCATION: (1)..(24)
<223> OTHER INFORMATION: n is t or u

<400> SEQUENCE: 110
gcccngcngn cnagacnggg gaga                                              24

<210> SEQ ID NO 111
<211> LENGTH: 24
<212> TYPE: DNA
<213> ORGANISM: Artificial Sequence
<220> FEATURE:
<223> OTHER INFORMATION: Antisense oligomer-GAA-IVS1(-158-135)
<220> FEATURE:
<221> NAME/KEY: misc_feature
<222> LOCATION: (1)..(24)
<223> OTHER INFORMATION: n is t or u

<400> SEQUENCE: 111
gngnngcccn gcngncngga cngg                                              24

<210> SEQ ID NO 112
<211> LENGTH: 19
<212> TYPE: DNA
<213> ORGANISM: Artificial Sequence
<220> FEATURE:
<223> OTHER INFORMATION: Antisense oligomer-GAA-IVS1(-163-145)
<220> FEATURE:
<221> NAME/KEY: misc_feature
<222> LOCATION: (1)..(19)
<223> OTHER INFORMATION: n is t or u

<400> SEQUENCE: 112
gcngncnaga cngggggaga                                                   19

<210> SEQ ID NO 113
<211> LENGTH: 19
<212> TYPE: DNA
<213> ORGANISM: Artificial Sequence
<220> FEATURE:
<223> OTHER INFORMATION: Antisense oligomer-GAA-IVS1(-153-135)
<220> FEATURE:
<221> NAME/KEY: misc_feature
<222> LOCATION: (1)..(19)
<223> OTHER INFORMATION: n is t or u

<400> SEQUENCE: 113
gngnngcccn gcngncnag                                                    19

<210> SEQ ID NO 114

<400> SEQUENCE: 114

000

<210> SEQ ID NO 115
<211> LENGTH: 25
<212> TYPE: DNA
<213> ORGANISM: Artificial Sequence
<220> FEATURE:
<223> OTHER INFORMATION: Antisense oligomer-GAA-IVS2(-168-192)
<220> FEATURE:
<221> NAME/KEY: misc_feature
<222> LOCATION: (1)..(25)
```

<223> OTHER INFORMATION: n is t or u

<400> SEQUENCE: 115
cnggagnacc ngncaccgng gngnc                                    25

<210> SEQ ID NO 116
<211> LENGTH: 25
<212> TYPE: DNA
<213> ORGANISM: Artificial Sequence
<220> FEATURE:
<223> OTHER INFORMATION: Antisense oligomer-GAA-IVS2(-173-197)
<220> FEATURE:
<221> NAME/KEY: misc_feature
<222> LOCATION: (1)..(25)
<223> OTHER INFORMATION: n is t or u

<400> SEQUENCE: 116
gccnncngga gnaccngnca ccgng                                    25

<210> SEQ ID NO 117
<211> LENGTH: 20
<212> TYPE: DNA
<213> ORGANISM: Artificial Sequence
<220> FEATURE:
<223> OTHER INFORMATION: Antisense oligomer-GAA-IVS2(-168-187)
<220> FEATURE:
<221> NAME/KEY: misc_feature
<222> LOCATION: (1)..(20)
<223> OTHER INFORMATION: n is t or u

<400> SEQUENCE: 117
gnaccngnca ccgnggngnc                                          20

<210> SEQ ID NO 118
<211> LENGTH: 20
<212> TYPE: DNA
<213> ORGANISM: Artificial Sequence
<220> FEATURE:
<223> OTHER INFORMATION: Antisense oligomer-GAA-IVS2(-178-197)
<220> FEATURE:
<221> NAME/KEY: misc_feature
<222> LOCATION: (1)..(20)
<223> OTHER INFORMATION: n is t or u

<400> SEQUENCE: 118
gccnncngga gnaccngnca                                          20

<210> SEQ ID NO 119

<400> SEQUENCE: 119

000

<210> SEQ ID NO 120

<400> SEQUENCE: 120

000

<210> SEQ ID NO 121
<211> LENGTH: 17
<212> TYPE: DNA
<213> ORGANISM: Artificial Sequence
<220> FEATURE:
<223> OTHER INFORMATION: Primer-FWD124

<400> SEQUENCE: 121
cgttgttcag cgaggga                                             17

<210> SEQ ID NO 122
<211> LENGTH: 21
<212> TYPE: DNA
<213> ORGANISM: Artificial Sequence
<220> FEATURE:
<223> OTHER INFORMATION: Primer-FWD645

<400> SEQUENCE: 122
ctcctctgaa atgggctaca c                                              21

<210> SEQ ID NO 123
<211> LENGTH: 18
<212> TYPE: DNA
<213> ORGANISM: Artificial Sequence
<220> FEATURE:
<223> OTHER INFORMATION: Primer-REV780

<400> SEQUENCE: 123
acctcgtagc gcctgtta                                                  18

<210> SEQ ID NO 124
<211> LENGTH: 20
<212> TYPE: DNA
<213> ORGANISM: Artificial Sequence
<220> FEATURE:
<223> OTHER INFORMATION: Antisense oligomer-GAA-IVS1(-39-20)

<400> SEQUENCE: 124
gcucagcagg gaggcgggag                                                20

<210> SEQ ID NO 125
<211> LENGTH: 20
<212> TYPE: DNA
<213> ORGANISM: Artificial Sequence
<220> FEATURE:
<223> OTHER INFORMATION: Antisense oligomer-GAA-IVS1(-74-55)

<400> SEQUENCE: 125
ggcucucaaa gcagcucuga                                                20

<210> SEQ ID NO 126
<211> LENGTH: 25
<212> TYPE: DNA
<213> ORGANISM: Artificial Sequence
<220> FEATURE:
<223> OTHER INFORMATION: Antisense oligomer-GAA-IVS1(-99-75)

<400> SEQUENCE: 126
gacaucaacc gcggcuggca cugca                                          25

<210> SEQ ID NO 127
<211> LENGTH: 25
<212> TYPE: DNA
<213> ORGANISM: Artificial Sequence
<220> FEATURE:
<223> OTHER INFORMATION: Antisense oligomer-GAA-IVS1(-139-115)

<400> SEQUENCE: 127
ggguaaggug gccagggugg guguu                                          25

<210> SEQ ID NO 128
<211> LENGTH: 19
<212> TYPE: DNA
<213> ORGANISM: Artificial Sequence
<220> FEATURE:

<223> OTHER INFORMATION: Antisense oligomer-GAA-IVS1(-158-140)

<400> SEQUENCE: 128
gcccugcugu cuagacugg                                                    19

<210> SEQ ID NO 129
<211> LENGTH: 20
<212> TYPE: DNA
<213> ORGANISM: Artificial Sequence
<220> FEATURE:
<223> OTHER INFORMATION: Antisense oligomer-GAA-IVS1.6.20

<400> SEQUENCE: 129
gcggggcaga cgtcaggtgt                                                   20

<210> SEQ ID NO 130
<211> LENGTH: 20
<212> TYPE: DNA
<213> ORGANISM: Artificial Sequence
<220> FEATURE:
<223> OTHER INFORMATION: Antisense oligomer-GAA-IVS1.10.20

<400> SEQUENCE: 130
cagcgcgggg cagacgtcag                                                   20

<210> SEQ ID NO 131
<211> LENGTH: 20
<212> TYPE: DNA
<213> ORGANISM: Artificial Sequence
<220> FEATURE:
<223> OTHER INFORMATION: Antisense oligomer-GAA-IVS1.24.20

<400> SEQUENCE: 131
gatgttaccg ccggcagcgc                                                   20

<210> SEQ ID NO 132
<211> LENGTH: 20
<212> TYPE: DNA
<213> ORGANISM: Artificial Sequence
<220> FEATURE:
<223> OTHER INFORMATION: Antisense oligomer-GAA-IVS1.28.20

<400> SEQUENCE: 132
ctgggatgtt accgccggca                                                   20

<210> SEQ ID NO 133
<211> LENGTH: 20
<212> TYPE: DNA
<213> ORGANISM: Artificial Sequence
<220> FEATURE:
<223> OTHER INFORMATION: Antisense oligomer-GAA-IVS1.32.20

<400> SEQUENCE: 133
gcttctggga tgttaccgcc                                                   20

<210> SEQ ID NO 134
<211> LENGTH: 20
<212> TYPE: DNA
<213> ORGANISM: Artificial Sequence
<220> FEATURE:
<223> OTHER INFORMATION: Antisense oligomer-GAA-IVS1.2015.20

<400> SEQUENCE: 134
tggcaactcg tatgtcctta                                                   20

```
<210> SEQ ID NO 135
<211> LENGTH: 20
<212> TYPE: DNA
<213> ORGANISM: Artificial Sequence
<220> FEATURE:
<223> OTHER INFORMATION: Antisense oligomer-GAA-IVS1.2019.20

<400> SEQUENCE: 135
attctggcaa ctcgtatgtc                                                 20

<210> SEQ ID NO 136
<211> LENGTH: 20
<212> TYPE: DNA
<213> ORGANISM: Artificial Sequence
<220> FEATURE:
<223> OTHER INFORMATION: Antisense oligomer-GAA-IVS1.2024.20

<400> SEQUENCE: 136
aagtgattct ggcaactcgt                                                 20

<210> SEQ ID NO 137
<211> LENGTH: 20
<212> TYPE: DNA
<213> ORGANISM: Artificial Sequence
<220> FEATURE:
<223> OTHER INFORMATION: Antisense oligomer-GAA-IVS1.2037.20

<400> SEQUENCE: 137
tgggtgtcag cggaagtgat                                                 20

<210> SEQ ID NO 138
<211> LENGTH: 20
<212> TYPE: DNA
<213> ORGANISM: Artificial Sequence
<220> FEATURE:
<223> OTHER INFORMATION: Antisense oligomer-GAA-IVS1.2043.20

<400> SEQUENCE: 138
gtccactggg tgtcagcgga                                                 20

<210> SEQ ID NO 139
<211> LENGTH: 20
<212> TYPE: DNA
<213> ORGANISM: Artificial Sequence
<220> FEATURE:
<223> OTHER INFORMATION: Antisense oligomer-GAA-IVS1.2048.20

<400> SEQUENCE: 139
gcttggtcca ctgggtgtca                                                 20

<210> SEQ ID NO 140
<211> LENGTH: 20
<212> TYPE: DNA
<213> ORGANISM: Artificial Sequence
<220> FEATURE:
<223> OTHER INFORMATION: Antisense oligomer-GAA-IVS1.2071.20

<400> SEQUENCE: 140
ccccacttct gcataaaggt                                                 20

<210> SEQ ID NO 141
<211> LENGTH: 20
<212> TYPE: DNA
<213> ORGANISM: Artificial Sequence
<220> FEATURE:
<223> OTHER INFORMATION: Antisense oligomer-GAA-IVS1.2075.20
```

<400> SEQUENCE: 141
ggagccccac ttctgcataa					20

<210> SEQ ID NO 142
<211> LENGTH: 20
<212> TYPE: DNA
<213> ORGANISM: Artificial Sequence
<220> FEATURE:
<223> OTHER INFORMATION: Antisense oligomer-GAA-IVS1.2079.20

<400> SEQUENCE: 142
gctgggagcc ccacttctgc					20

<210> SEQ ID NO 143
<211> LENGTH: 20
<212> TYPE: DNA
<213> ORGANISM: Artificial Sequence
<220> FEATURE:
<223> OTHER INFORMATION: Antisense oligomer-GAA-IVS1.2088.20

<400> SEQUENCE: 143
ccacgcctgg ctgggagccc					20

<210> SEQ ID NO 144
<211> LENGTH: 20
<212> TYPE: DNA
<213> ORGANISM: Artificial Sequence
<220> FEATURE:
<223> OTHER INFORMATION: Antisense oligomer-GAA-IVS1.2115.20

<400> SEQUENCE: 144
tccgaagtgc tgggatttca					20

<210> SEQ ID NO 145
<211> LENGTH: 20
<212> TYPE: DNA
<213> ORGANISM: Artificial Sequence
<220> FEATURE:
<223> OTHER INFORMATION: Antisense oligomer-GAA-IVS1.2132.20

<400> SEQUENCE: 145
tccacccccc ttggccttcc					20

<210> SEQ ID NO 146
<211> LENGTH: 20
<212> TYPE: DNA
<213> ORGANISM: Artificial Sequence
<220> FEATURE:
<223> OTHER INFORMATION: Antisense oligomer-GAA-IVS1.2135.20

<400> SEQUENCE: 146
tgatccaccc cccttggcct					20

<210> SEQ ID NO 147
<211> LENGTH: 20
<212> TYPE: DNA
<213> ORGANISM: Artificial Sequence
<220> FEATURE:
<223> OTHER INFORMATION: Antisense oligomer-GAA-IVS1.2140.20

<400> SEQUENCE: 147
tcaagtgatc cacccccctt					20

<210> SEQ ID NO 148
<211> LENGTH: 20

-continued

```
<212> TYPE: DNA
<213> ORGANISM: Artificial Sequence
<220> FEATURE:
<223> OTHER INFORMATION: Antisense oligomer-GAA-IVS1.2152.20

<400> SEQUENCE: 148
gaactcctga gctcaagtga                                              20

<210> SEQ ID NO 149
<211> LENGTH: 20
<212> TYPE: DNA
<213> ORGANISM: Artificial Sequence
<220> FEATURE:
<223> OTHER INFORMATION: Antisense oligomer-GAA-IVS1.2156.20

<400> SEQUENCE: 149
tctcgaactc ctgagctcaa                                              20

<210> SEQ ID NO 150
<211> LENGTH: 20
<212> TYPE: DNA
<213> ORGANISM: Artificial Sequence
<220> FEATURE:
<223> OTHER INFORMATION: Antisense oligomer-GAA-IVS1.2165.20

<400> SEQUENCE: 150
ccaggctggt ctcgaactcc                                              20

<210> SEQ ID NO 151
<211> LENGTH: 20
<212> TYPE: DNA
<213> ORGANISM: Artificial Sequence
<220> FEATURE:
<223> OTHER INFORMATION: Antisense oligomer-GAA-IVS1.2178.20

<400> SEQUENCE: 151
tttgccatgt tacccaggct                                              20

<210> SEQ ID NO 152
<211> LENGTH: 20
<212> TYPE: DNA
<213> ORGANISM: Artificial Sequence
<220> FEATURE:
<223> OTHER INFORMATION: Antisense oligomer-GAA-IVS1.2185.20

<400> SEQUENCE: 152
acgggatttt gccatgttac                                              20

<210> SEQ ID NO 153
<211> LENGTH: 20
<212> TYPE: DNA
<213> ORGANISM: Artificial Sequence
<220> FEATURE:
<223> OTHER INFORMATION: Antisense oligomer-GAA-IVS1.2190.20

<400> SEQUENCE: 153
tagagacggg attttgccat                                              20

<210> SEQ ID NO 154
<211> LENGTH: 20
<212> TYPE: DNA
<213> ORGANISM: Artificial Sequence
<220> FEATURE:
<223> OTHER INFORMATION: Antisense oligomer-GAA-IVS1.2195.20

<400> SEQUENCE: 154
```
ttttgtagag acgggatttt                                                20

<210> SEQ ID NO 155
<211> LENGTH: 20
<212> TYPE: DNA
<213> ORGANISM: Artificial Sequence
<220> FEATURE:
<223> OTHER INFORMATION: Antisense oligomer-GAA-IVS1.2202.20

<400> SEQUENCE: 155
tctgtatttt tgtagagacg                                                20

<210> SEQ ID NO 156
<211> LENGTH: 20
<212> TYPE: DNA
<213> ORGANISM: Artificial Sequence
<220> FEATURE:
<223> OTHER INFORMATION: Antisense oligomer-GAA-IVS1.2206.20

<400> SEQUENCE: 156
attttctgta ttttgtaga                                                 20

<210> SEQ ID NO 157
<211> LENGTH: 20
<212> TYPE: DNA
<213> ORGANISM: Artificial Sequence
<220> FEATURE:
<223> OTHER INFORMATION: Antisense oligomer-GAA-IVS1.2210.20

<400> SEQUENCE: 157
gctaattttc tgtattttg                                                 20

<210> SEQ ID NO 158
<211> LENGTH: 25
<212> TYPE: DNA
<213> ORGANISM: Artificial Sequence
<220> FEATURE:
<223> OTHER INFORMATION: Antisense oligomer-GAAEx2A(+202+226)

<400> SEQUENCE: 158
ggcccugguc ugcuggcucc cugcu                                          25

<210> SEQ ID NO 159
<211> LENGTH: 25
<212> TYPE: DNA
<213> ORGANISM: Artificial Sequence
<220> FEATURE:
<223> OTHER INFORMATION: Antisense oligomer-GAAEx2A(+367+391)

<400> SEQUENCE: 159
gcucccugca gccccugcuu ugcag                                          25

<210> SEQ ID NO 160
<211> LENGTH: 17
<212> TYPE: DNA
<213> ORGANISM: Artificial Sequence
<220> FEATURE:
<223> OTHER INFORMATION: Antisense oligomer-GAA-IVS2(-4-20)

<400> SEQUENCE: 160
cccgccccug cccugcc                                                   17

<210> SEQ ID NO 161
<211> LENGTH: 18
<212> TYPE: DNA
<213> ORGANISM: Artificial Sequence

```
<220> FEATURE:
<223> OTHER INFORMATION: Antisense oligomer-GAA-IVS2(-14-30)

<400> SEQUENCE: 161
uggccgccgc ccccgccc                                                        18

<210> SEQ ID NO 162
<211> LENGTH: 20
<212> TYPE: DNA
<213> ORGANISM: Artificial Sequence
<220> FEATURE:
<223> OTHER INFORMATION: Antisense oligomer-GAA-IVS2(-33-52)

<400> SEQUENCE: 162
uguccacgcg cacccucugc                                                      20

<210> SEQ ID NO 163
<211> LENGTH: 20
<212> TYPE: DNA
<213> ORGANISM: Artificial Sequence
<220> FEATURE:
<223> OTHER INFORMATION: Antisense oligomer-GAA-IVS2(-53-72)

<400> SEQUENCE: 163
gugaggugcg ugggugucga                                                      20

<210> SEQ ID NO 164
<211> LENGTH: 20
<212> TYPE: DNA
<213> ORGANISM: Artificial Sequence
<220> FEATURE:
<223> OTHER INFORMATION: Antisense oligomer-GAA-IVS2(-73-92)

<400> SEQUENCE: 164
gcaacaugca ccccacccuu                                                      20

<210> SEQ ID NO 165
<211> LENGTH: 20
<212> TYPE: DNA
<213> ORGANISM: Artificial Sequence
<220> FEATURE:
<223> OTHER INFORMATION: Antisense oligomer-GAA-IVS2(-93-112)

<400> SEQUENCE: 165
agggcccagc acacaguggu                                                      20

<210> SEQ ID NO 166
<211> LENGTH: 20
<212> TYPE: DNA
<213> ORGANISM: Artificial Sequence
<220> FEATURE:
<223> OTHER INFORMATION: Antisense oligomer-GAA-IVS2(-113-132)

<400> SEQUENCE: 166
ucacaccucc gcucccagca                                                      20

<210> SEQ ID NO 167
<211> LENGTH: 18
<212> TYPE: DNA
<213> ORGANISM: Artificial Sequence
<220> FEATURE:
<223> OTHER INFORMATION: Antisense oligomer-GAA-IVS2(-133-150)

<400> SEQUENCE: 167
ggcgcugcca uugucugc                                                        18
```

```
<210> SEQ ID NO 168
<211> LENGTH: 20
<212> TYPE: DNA
<213> ORGANISM: Artificial Sequence
<220> FEATURE:
<223> OTHER INFORMATION: Antisense oligomer-GAA-IVS2(-153-172)

<400> SEQUENCE: 168 gugucccac ugcucccga                                                    20

<210> SEQ ID NO 169
<211> LENGTH: 20
<212> TYPE: DNA
<213> ORGANISM: Artificial Sequence
<220> FEATURE:
<223> OTHER INFORMATION: Antisense oligomer-GAA-IVS2(-173-192)

<400> SEQUENCE: 169
cuggaguacc ugucaccgug                                                  20

<210> SEQ ID NO 170
<211> LENGTH: 20
<212> TYPE: DNA
<213> ORGANISM: Artificial Sequence
<220> FEATURE:
<223> OTHER INFORMATION: Antisense oligomer-GAA-IVS2(-193-212)

<400> SEQUENCE: 170 ugagcccga gcccugccuu                                                   20

<210> SEQ ID NO 171
<211> LENGTH: 25
<212> TYPE: DNA
<213> ORGANISM: Artificial Sequence
<220> FEATURE:
<223> OTHER INFORMATION: Antisense oligomer-GAA-IVS2(-213-237)

<400> SEQUENCE: 171
ugacccaccu uuucauaaag augaa                                            25

<210> SEQ ID NO 172
<211> LENGTH: 25
<212> TYPE: DNA
<213> ORGANISM: Artificial Sequence
<220> FEATURE:
<223> OTHER INFORMATION: Antisense oligomer-GAA-IVS2(-234-258)

<400> SEQUENCE: 172
cucuggcagc ccuacucuac cugac                                            25

<210> SEQ ID NO 173
<211> LENGTH: 27
<212> TYPE: DNA
<213> ORGANISM: Artificial Sequence
<220> FEATURE:
<223> OTHER INFORMATION: Antisense oligomer-GAA-IVS2(-338-364)

<400> SEQUENCE: 173
cuaguauaaa uacaucccaa auuuugc                                          27

<210> SEQ ID NO 174
<211> LENGTH: 20
<212> TYPE: DNA
<213> ORGANISM: Artificial Sequence
<220> FEATURE:
<223> OTHER INFORMATION: Antisense oligomer-GAA-IVS2.6.20
```

<400> SEQUENCE: 174 ccgccccgc ccctgccctg                                              20

<210> SEQ ID NO 175
<211> LENGTH: 20
<212> TYPE: DNA
<213> ORGANISM: Artificial Sequence
<220> FEATURE:
<223> OTHER INFORMATION: Antisense oligomer-GAA-IVS2.9.20

<400> SEQUENCE: 175
ccgccgcccc cgcccctgcc                                             20

<210> SEQ ID NO 176
<211> LENGTH: 20
<212> TYPE: DNA
<213> ORGANISM: Artificial Sequence
<220> FEATURE:
<223> OTHER INFORMATION: Antisense oligomer-GAA-IVS2.12.20

<400> SEQUENCE: 176
tggccgccgc ccccgccccct                                            20

<210> SEQ ID NO 177
<211> LENGTH: 20
<212> TYPE: DNA
<213> ORGANISM: Artificial Sequence
<220> FEATURE:
<223> OTHER INFORMATION: Antisense oligomer-GAA-IVS2.18.20

<400> SEQUENCE: 177
ctgccctggc cgccgccccc                                             20

<210> SEQ ID NO 178
<211> LENGTH: 20
<212> TYPE: DNA
<213> ORGANISM: Artificial Sequence
<220> FEATURE:
<223> OTHER INFORMATION: Antisense oligomer-GAA-IVS2.24.20

<400> SEQUENCE: 178
caccctctgc cctggccgcc                                             20

<210> SEQ ID NO 179
<211> LENGTH: 20
<212> TYPE: DNA
<213> ORGANISM: Artificial Sequence
<220> FEATURE:
<223> OTHER INFORMATION: Antisense oligomer-GAA-IVS2.27.20

<400> SEQUENCE: 179
gcgcaccctc tgccctggcc                                             20

<210> SEQ ID NO 180
<211> LENGTH: 20
<212> TYPE: DNA
<213> ORGANISM: Artificial Sequence
<220> FEATURE:
<223> OTHER INFORMATION: Antisense oligomer-GAA-IVS2.40.20

<400> SEQUENCE: 180
tgtcgatgtc cacgcgcacc                                             20

<210> SEQ ID NO 181

```
<211> LENGTH: 20
<212> TYPE: DNA
<213> ORGANISM: Artificial Sequence
<220> FEATURE:
<223> OTHER INFORMATION: Antisense oligomer-GAA-IVS2.48.20

<400> SEQUENCE: 181
tgcgtgggtg tcgatgtcca                                              20

<210> SEQ ID NO 182
<211> LENGTH: 20
<212> TYPE: DNA
<213> ORGANISM: Artificial Sequence
<220> FEATURE:
<223> OTHER INFORMATION: Antisense oligomer-GAA-IVS2.67.20

<400> SEQUENCE: 182
gcaccccacc cttgtgaggt                                              20

<210> SEQ ID NO 183
<211> LENGTH: 20
<212> TYPE: DNA
<213> ORGANISM: Artificial Sequence
<220> FEATURE:
<223> OTHER INFORMATION: Antisense oligomer-GAA-IVS2.72.20

<400> SEQUENCE: 183
aacatgcacc ccaccttgt                                               20

<210> SEQ ID NO 184
<211> LENGTH: 20
<212> TYPE: DNA
<213> ORGANISM: Artificial Sequence
<220> FEATURE:
<223> OTHER INFORMATION: Antisense oligomer-GAA-IVS2.431.20

<400> SEQUENCE: 184
aggaggagga cgcctccccc                                              20

<210> SEQ ID NO 185
<211> LENGTH: 20
<212> TYPE: DNA
<213> ORGANISM: Artificial Sequence
<220> FEATURE:
<223> OTHER INFORMATION: Antisense oligomer-GAA-IVS2.446.20

<400> SEQUENCE: 185
ctcatctgca gagccaggag                                              20

<210> SEQ ID NO 186
<211> LENGTH: 20
<212> TYPE: DNA
<213> ORGANISM: Artificial Sequence
<220> FEATURE:
<223> OTHER INFORMATION: Antisense oligomer-GAA-IVS2.451.20

<400> SEQUENCE: 186
gctccctcat ctgcagagcc                                              20

<210> SEQ ID NO 187
<211> LENGTH: 20
<212> TYPE: DNA
<213> ORGANISM: Artificial Sequence
<220> FEATURE:
<223> OTHER INFORMATION: Antisense oligomer-GAA-IVS2.454.20

<400> SEQUENCE: 187
```

```
tcggctccct catctgcaga                                          20

<210> SEQ ID NO 188
<211> LENGTH: 20
<212> TYPE: DNA
<213> ORGANISM: Artificial Sequence
<220> FEATURE:
<223> OTHER INFORMATION: Antisense oligomer-GAA-IVS2.457.20

<400> SEQUENCE: 188
gcctcggctc cctcatctgc                                          20
```